United States Patent
Lee et al.

(12)
(10) Patent No.: US 6,215,040 B1
(45) Date of Patent: Apr. 10, 2001

(54) IL-5 TRANSGENIC MOUSE

(75) Inventors: James J. Lee; Nancy A. Lee, both of Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/155,884

(22) PCT Filed: Apr. 9, 1997

(86) PCT No.: PCT/US97/05932

§ 371 Date: Oct. 7, 1998

§ 102(e) Date: Oct. 7, 1998

(87) PCT Pub. No.: WO97/38086

PCT Pub. Date: Oct. 16, 1997

(51) Int. Cl.[7] .......................... C12N 15/00; C12N 15/09; C12N 15/63
(52) U.S. Cl. ..................... 800/18; 800/3; 800/9; 800/13; 800/14; 435/320.1
(58) Field of Search .................. 800/3, 13, 18, 800/9, 14; 435/320.1

(56) References Cited

U.S. PATENT DOCUMENTS 6,025,539  2/2000  Lee et al. .

OTHER PUBLICATIONS

Wall, RJ Transgenic livestock: Progress and prospects for the future. Theriogenology 45: 57–68, 1996.*

Anderson, G.P., "Eosinophilia in genetically altered mice", *Eur. Respiratory Review,* 5, 231–347, (1995).

Blyth, D.I., et al., "Lung Inflammation and Epithelial Changes in a Murine Model of Atopic Asthma", *Am. J. Respir Cell Mol. Biol.,* 14, 425–438, (1996).

Bourke, P.F., et al., "Localization of the Inducible Enhancer in the Mouse Interleukin–5 Gene That is Responsible to T–Cell Receptor Stimulation", *Blood,* 85, 2069–2077, (Apr. 1995).

Brusselle, G., et al., "Allergen–Induced Airway Inflammation and Bronchial Responsiveness in Wild–Type and Interleukin–4–Deficient Mice", *Am. J. Respir. Cell Mol. Biol.,* 12, 254–259, (1995).

Corry, D.B., et al., "Interleukin 4, but Not Interleukin 5 or Eosinophils, Is Required in a Murine Model of Acute Airway Hyperreactivity", *J. Exp. Med.,* 183, 109–117, (Jan. 1996).

Dent, L.A., et al., "Eosinophilia in Transgenic Mice Expressing Interleukin 5", *J. Experimental Medicine, vol.* 172, 1425–1431, (Nov. 1990).

Foster, P.S., et al., "Interleukin 5 Deficiency Abolishes Eosinophilia, Airways Hyperreactivity, and Lung Damage in a Mouse Asthma Model", *J. Exp. Med.,* 183, 195–201, (Jan. 1996).

Fugger, L., et al., "Expression of HLA–DR4 and Human CD4 Transgenes in Mice Determines the Variable Region Beta–chain T–cell Repertoire and Mediates an HLA–DR–Restricted Immune Response", *Proc. Natl. Acad. Sci. USA,*91, 6151–6155, (Jun. 1994).

Georgopoulos, K., et al., "A T Cell–Specific Enhancer is Located in a DNase I–Hypersensitive Area at the 3' End of the CD3–delta Gene", *EMBO J.,* 7, 2401–2407, (1988).

Hackett, B.P., et al., "Cell–Specific Expression of a Clara Cell Secretory Protein–Human Growth Hormone Gene in the Bronchiolar Epithelium of Transgenic Mice", *Proc. Natl. Acad. Sci. USA,* 89, 9079–9083, (Oct. 1992).

Hamelmann, E., et al., "Requirement for CD8+ T Cells in the Development of Airway Hyperresponsiveness in a Murine Model of Airway Sensitization", *J. Exp. Med.,* 183, 1719–1729, (Apr., 1996).

Houdebine, L., "Production of pharmaceutical proteins from transgenic animals", *J. of Biotechnology,* 34, 269–287, (1994).

Iwamoto, T., et al., "Evaluation of Airway Hyperreactivity in Interleukin–5 Transgenic Mice", *Intl. Arch. Allegery Immunol.,* 108 (Suppl. 1), 28–30, (Sep., 1995).

Lee, N.A., et al., "Expression of IL-5 in thymocytes/T cells leads to the development of a massive eosinophilia, extramedullary eosinophilopoiesis, and unique histopathologies", *The Journal of Immunology,* 158, 1332–1344, (1997).

Lefort, J., et al., "Effect of Antigen Provocation of IL–5 Transgenic Mice on Eosinophil Mobilization and Bronchial Hyperresponsiveness", *J. Allergy Clin. Immunol,* 97, 788–799, (Mar. 1996).

Nakajima, H., et al., "CD4+ T–Lymphocytes and Interleuukin–5 Mediate Antigen–Induced Eosinophil Infiltration into the Mouse Trachea", *American Review of Respiratory Disease,* 146, 374–377, (Aug. 1992).

Oshiba, A., et al., "Pretreatment with Allergen Prevents Immediate Hypersensitivity and Airway Hyperresponsiveness", *Am. J. Respir. Crit. Care Med.,* 153, 102–109, (Jan., 1996).

Rankin, J.A., et al., "Phenotypic and Physiologic Characterization of Transgenic Mice Expressing Interleukin 4 in the Lung: Lymphocytic and Eosinophilic Inflammation Without Airway Hyperreactivity", *Proc. Natl. Acad. Sci. USA,* 93, 7821–7825, (Jul. 1996).

(List continued on next page.)

*Primary Examiner*—Karen M. Hauda
*Assistant Examiner*—Anne-Marie Baker
(74) *Attorney, Agent, or Firm*—Schwegman, Lundberg, Woessner & Kluth

(57) ABSTRACT

A transgenic mouse is provided, the cells of which contain and express IL-5 in a cell type- or tissue-specific manner and in an amount which results in an IL-5-associated pathology. Also provided are expression cassettes comprising an IL-5 gene, operably linked to a cell type- or tissue-specific transcriptional control sequence and methods of using transgenic mice comprising the expression cassettes

7 Claims, 42 Drawing Sheets

OTHER PUBLICATIONS

Tohyama, K., et al., "Establishment of an Interleukin–5–Dependent Subclone from an Interleukin–3–Dependent Murine Hemopoietic Progenitor Cell Line, LyD9, and its Malignant Transformation by Autocrine Secretion of Interleukin–5", *EMBO J.*, 1823–1830, (1990).

Tominaga, A., et al., "Transgenic Mice Expressing a B Cell Growth and Differentiation Factor Gene (Interleukin 5) Develop Eosinophilia and Autoantibody Production", *J. Experimental Medicine,* 173, 429–437, (Feb., 1991).

van den Elsen, P., et al., "Exon/Intron Organization fo the Genes Coding for the Delta Chains of the Human and Murine T–Cell Receptor/T3 Complex", *Proc. Natl. Acad. Sci. USA,* 83, 2944–2948, (May, 1986).

* cited by examiner

| age (months) | mouse | Percentage spleen cell types ||||| Eosinophil lineage cells/femur (X 10⁻⁶) ||||
|---|---|---|---|---|---|---|---|---|---|---|
| | | total cells/spleen (X 10⁻⁷) | erythroblast | mononuclear | eosinophil | neutrophil | Class I | Class II | Class III | Class IV |
| 1 | +/+ | 17.50 (3.64)³ | 21.17 (6.81) | 72.83(8.04) | 0.33(0.29) | 5.67(1.04) | 0.01(0.01) | <0.01 | 0.02 (0.02) | 0.03 (0.03) |
| | NJ.1638 | 97.40 (7.20)⁴ | 28.88(2.14) | 19.38(2.36) | 48.25(2.75) | 3.50(1.47) | 0.85 (0.46) | 1.40 (0.44) | 12.27 (2.71) | 33.23 (5.65) |
| 4 | +/+ | 18.63(4.05)³ | 19.99(13.99) | 76.14(15.90) | 0.62(0.80) | 3.25(2.60) | 0.03 (0.03) | 0.01 (0.01) | 0.02 (0.02) | 0.13 (0.17) |
| | NJ.1638 | 311.40 (120.49)⁴ | 16.98(7.49) | 27.38(10.78) | 51.31(8.09) | 4.26(4.69) | 2.25 (1.29) | 8.56 (5.02) | 56.18 (24.17) | 92.69(28.51) |
| 10 | +/+ | 20.33 (2.32)³ | 14.50(7.37) | 80.17(8.52) | 0.33(0.29) | 4.83(1.53) | 0.01 (0.01) | <0.01 | 0.01 (0.01) | 0.05 (0.04) |
| | NJ.1638 | 387.67(118.00)³ | 8.00(3.46) | 40.50(7.40) | 47.50(7.50) | 4.00(3.00) | 4.30 (2.78) | 7.12(4.41) | 60.72(37.50) | 122.13 (46.95) |

FIG. 5A

| age (months) | mouse | Percentage spleen cell types ||||| Eosinophil lineage cells/femur (X $10^{-6}$) ||||
|---|---|---|---|---|---|---|---|---|---|---|
| | | total cells/spleen (X $10^{-7}$) | erythroblast | mononuclear | eosinophil | neutrophil | Class I | Class II | Class III | Class IV |
| 1 | +/+ | 17.50 (3.64)[3] | 21.17 (6.81) | 72.83(8.04) | 0.33(0.29) | 5.67(1.04) | 0.01(0.01) | <0.01 | 0.02 (0.02) | 0.03 (0.03) |
| | NJ.1638 | 97.40 (7.20)[4] | 28.88(2.14) | 19.38(2.36) | 48.25(2.75) | 3.50(1.47) | 0.85 (0.46) | 1.40 (0.44) | 12.27 (2.71) | 33.23 (5.65) |
| 4 | +/+ | 18.63(4.05)[3] | 19.99(13.99) | 76.14(15.90) | 0.62(0.80) | 3.25(2.60) | 0.03 (0.03) | 0.01 (0.01) | 0.02 (0.02) | 0.13 (0.17) |
| | NJ.1638 | 311.40 (120.49)[4] | 16.98(7.49) | 27.38(10.78) | 51.31(8.09) | 4.26(4.69) | 2.25 (1.29) | 8.56 (5.02) | 56.18 (24.17) | 92.69(28.51) |
| 10 | +/+ | 20.33 (2.32)[3] | 14.50(7.37) | 80.17(8.52) | 0.33(0.29) | 4.83(1.53) | 0.01 (0.01) | <0.01 | 0.01 (0.01) | 0.05 (0.04) |
| | NJ.1638 | 387.67(118.00)[3] | 8.00(3.46) | 40.50(7.40) | 47.50(7.50) | 4.00(3.00) | 4.30 (2.78) | 7.12(4.41) | 60.72(37.50) | 122.13 (46.95) |

FIG. 5C

|   1    |   2    |   3    |   4    |
|--------|--------|--------|--------|
| +/+ Tg | +/+ Tg | +/+ Tg | +/+ Tg |

Kb 2.37 —

1.35 —

18S

IL-5 TRANSGENIC MOUSE

BACKGROUND OF THE INVENTION

The etiology of many respiratory diseases has remained unclear in spite of direct attempts to determine factors that lead to pulmonary damage and loss of function. The underlying respiratory inflammation leading to variable airflow limitation and airway hyperresponsiveness to various stimuli in some respiratory diseases can be exacerbated by allergens, respiratory tract infections, or environmental agents. Localized cytokine/chemokine gene expression (King et al., *Am J. Respir. Cell & Mol. Biol.*, 14, 319 (1996)), secretion of low molecular weight inflammatory mediators (Henderson, *Ann. Allergy*, 72, 272 (1994)), and the recruitment of specific leukocyte cell types (Bentley et al., *J. Inv. Allerzol. Clin. Immunol.*, 4, 222 (1994)) have all been shown to contribute to respiratory inflammation. For example, asthma is a multifactorial syndrome characterized by breathlessness, pulmonary constriction, airway hyperreactivity and mucous accumulation. It is often, but not always associated with allergies (extrinsic) or environmental stimuli, e.g., tobacco smoke.

Many pathophysiological manifestations of asthma are associated with airway infiltration by eosinophils and lymphocytes. This infiltration is mediated by cytokines and chemokines. Leukocyte influx, in turn, has been associated with the development of lung dysfunction, even in nominal cases of asthma. Indeed, the extent of infiltration generally correlates with the severity of disease. Antigen-induced mouse models of pulmonary allergic disease have proved particularly informative in the genetic dissection of inflammatory pathways in the lung. Typically, these models involve sensitization with a specific antigen (e.g., ovalbumin) followed by airborne administration of the same antigen. Sensitized mice treated with aerosolized allergen develop leukocytic infiltrates of the airway lumen dominated by CD4+ lymphocytes and eosinophils. These mice also develop many of the changes pathognomonic of asthma, including airway hyperresponsiveness (AHR) and goblet cell hyperplasia with excessive mucus production.

The cellular signals leading to airway inflammation, eosinophil infiltration, and AHR remain obscure. Lymphocytes, eosinophils, and mast cells have been implicated in the AHR of antigen-challenged mouse models of asthma. SCID mice, which lack both T and B lymphocytes, fail to develop either an airway eosinophilia or bronchial hyperreactivity after ovalbumin sensitization (Corry et al., *J. Exp. Med.*, 183, 109 (1996)). The depletion of CD4+ lymphocytes, either by treatment with anti-CD4 antibodies or MHC Class II gene knock-out, eliminated both eosinophil airway infiltration and AHR in antigen-challenged mice (Garett et al., *Am. J. Respir. Cell & Mol. Biol.*, 10, 587 (1994)). In contrast, depletion of CD8+ T lymphocytes with anti-CD8 antibodies had no effect on lung eosinophil infiltration but eliminated AHR (Nakajima et al., *Am. J. Respir. Cell & Mol. Biol.*, 10, 587 (1994); Hammelmann et al., *J. Exp. Med.*, 183, 1719 (1996)). Moreover, studies with mast cell deficient mice (W/W$^v$) indicated that mast cells were not specifically required for either eosinophil airway infiltration or AHR (Bruselle et al., *Am. J. Respir. Cell & Mol. Biol.*, 12, 254 (1995)).

Collectively, the antigen sensitization and challenge mouse models implicate T-lymphocytes as a component of the inflammatory response. Furthermore, IL-4 or IL-5 cytokine gene knock-out studies using aerosolized antigen challenge suggest that IL-4 and IL-5 are each important components of proinflammatory cascades that ultimately result in eosinophil airway infiltration and pathophysiological changes characteristic of asthma (Bruselle et al., supra; Foster et al., *J. Exp. Med.*, 183, 195 (1996)).

To define the role of IL-5 in vivo, Dent et al. (*J. Exp. Med.*, 172, 1425 (1990)) prepared transgenic mice in which transcription of a genomic copy of the IL-5 gene was under the transcriptional regulatory influence of the dominant control region (DCR) of the gene encoding human CD2 (a T cell surface antigen). Although Dent et al. showed that serum IL-5 levels were elevated in transgenic mice (Tg5C2), because the CD2 enhancer element is only weakly active in mature peripheral T cells, the elevation in serum IL-5 levels was primarily due to thymocyte expression and not peripheral T cell expression. In contrast, serum IL-5 levels are elevated in parasite infested (*Mesocestroides corti*) or antigen challenged mice as a result of IL-5 expression by peripheral T cells. Moreover, despite the increase in serum IL-5 levels, the Tg5C2 mice showed no symptomatic effects of IL-5 overexpression other than a mild splenomegaly and an eosinophilia accompanying a 7-fold increase in white blood cell (WBC) count.

Tominaga et al. (*J. Exp. Med.*, 173, 429 (1991)) disclose that transgenic mice in which a IL-5 cDNA was linked to the mouse metallothionein promoter (Tg-6 mice) demonstrated a peripheral eosinophilia with a 3-fold increase in total WBCs. Serum IL-5 levels in Tg-6 mice were 16,000 pg/ml. The predominant sites of IL-5 expression in these mice were the kidney and liver. These organ sites are not normally associated with the production of IL-5 and thus fail to mimic the necessary microenvironmental cues that occur in peripheral sites. Thus, the lack of significant physiological effects in these mice may be the result of ectopically produced IL-5.

Thus, a need exists for an animal model that constitutively expresses IL-5 in a tissue and/or cell-type specific fashion. Moreover, a need exists for an animal model that constitutively expresses IL-5 in thymocytes and peripheral T cells, or in lung tissue, so as to result in IL-5 induced pathologies.

SUMMARY OF THE INVENTION

The invention provides a transgenic mouse whose cells incorporate a preselected chimeric DNA sequence which is integrated into the genome of the mouse and comprises a thymocyte and/or T cell specific transcription control sequence operatively linked to a DNA segment which encodes interleukin-5. The DNA segment which encodes interleukin-5 lacks endogenous interleukin-5 control sequences which are 5' to the interteukin-5 coding sequence. The DNA segment is preferably expressed as interleukin-5 so as to result in eosinophil-associated pathologies in the transgenic mouse. Preferably, the interleukin-5 encoded by the DNA segment is expressed in the serum of the transgenic mouse in an amount that is at least about fifty times, more preferably at least about seventy-five times, and even more preferably at least about one hundred times, greater than the amount of interieukin-5 in the serum of a corresponding nontransgenic mouse.

Another embodiment of the invention is a transgenic mouse, the cells of which contain a preselected chimeric DNA sequence comprising a lung specific transcription control sequence operatively linked to a DNA segment which encodes interleukin-5. The preselected chimeric DNA sequence is integrated into the genome of the mouse and expressed as interleukin-5 in an amount which preferably results in eosinophil-associated pathologies. The interleukin-5 encoded by the DNA segment is preferably expressed in the transgenic mouse in an amount that is at least about fifty times, more preferably at least about one hundred times, and even more preferably at least about one thousand times, greater than the amount of interleukin-5 in a corresponding nontransgenic mouse. As described hereinbelow, a transgenic mouse that constitutively expressed IL-5 in lung epithelium resulted in a dramatic accumulation of peribronchial eosinophils and striking pathological changes including expansion of bronchus-associated lymphoid tissue (BALT), goblet cell hyperplasia, epithelial hypertrophy and focal collagen deposits. Surprisingly, these changes were not accompanied by a prominent eosinophil infiltration into the airway lumen. Thus, lung-specific expression of IL-5 alone (i.e., in the absence of antigen-induced pulmonary inflammation) can induce many of the pathologic changes associated with allergic respiratory disease. Moreover, these mice displayed AHR in response to methacholine challenge. Thus, AHR can occur without extensive infiltration of the airway lumen by eosinophils.

Also surprisingly, transgenic mice which expressed the IL-5 gene from a different lung specific transcriptional control sequence, e.g., the surfactant protein C (SPC) promoter, showed an increased cellularity in the parenchyma but not in the peribronchial lymph nodes. Moreover, many of the founder mice died before 4 months of age.

Further provided is a transgenic mouse, the cells of which contain a preselected chimeric DNA sequence comprising a skin, e.g., a basal keratinocyte, specific transcription control sequence operatively linked to a DNA segment which encodes interleukin-5. The preselected chimeric DNA sequence is integrated into the genome of the mouse and preferably is expressed as interleukin-5 in an amount which preferably results in eosinophil-associated pathologies. The interleukin-5 encoded by the DNA segment is preferably expressed in the transgenic mouse in an amount that is at least about two times, more preferably at least about fifty times, and even more preferably at least about one hundred times, greater than the amount of interleukin-5 in a corresponding nontransgenic mouse.

Also provided is an expression cassette comprising a DNA segment encoding interleukin-5, which segment lacks endogenous interleukin-5 control sequences that are 5' to the interleukin-5 coding sequence. The DNA segment is operably linked to a thymocyte and/or T cell specific transcription control sequence.

Another embodiment of the invention is an expression cassette comprising a DNA segment encoding interleukin-5 operably linked to a lung specific transcription control sequence.

Yet another embodiment of the invention is an expression cassette comprising a DNA segment encoding interleukin-5 operably linked to a basal keratinocyte specific transcription control sequence.

Also provided are methods of using the transgenic mice of the invention. One embodiment of the invention includes a method comprising expressing a chimeric DNA sequence, which is integrated into the genome of the transgenic mouse, in the cells of the transgenic mouse. The chimeric DNA sequence comprises a thymocyte and/or T cell specific transcription control sequence operatively linked to a DNA segment which encodes interleukin-5. The DNA segment lacks any endogenous interleukin-5 control sequences which are 5' to the interleukin-5 coding sequence. The DNA segment is expressed in the serum of the transgenic mouse in an amount of interleukin-5 that is at least about fifty times, preferably at least about seventy-five times, more preferably at least about one hundred times, greater than the amount of interleukin-5 in the serum of a corresponding nontransgenic mouse. Preferably, expression of the DNA segment is in an amount of interleukin-5 so as to result in eosinophil-associated pathologies.

Another embodiment of the invention is a method in which a chimeric DNA sequence is expressed in the cells of the transgenic mouse, wherein the chimeric DNA sequence comprises a basal keratinocyte specific transcription control sequence operatively linked to a DNA segment which encodes interleukin-5. The DNA segment is expressed in the transgenic mouse in an amount of interleukin-5 that is at least about two times, preferably at least about fifty times, and more preferably at least about one hundred times, greater than the amount of interleukin-5 in a corresponding nontransgenic mouse.

The invention also provides a method of using a transgenic mouse. The method comprises expressing a chimeric DNA sequence in the cells of the transgenic mouse. The chimeric DNA sequence, which is integrated into the genome of the transgenic mouse, comprises a basal keratinocyte specific transcription control sequence operatively linked to a DNA segment which encodes interleukin-5. The DNA segment lacks any endogenous interleukin-5 control sequences which are 5' to the interleukin-5 coding sequence. The DNA segment is expressed in an amount of interleukin-5 so as to result in eosinophil-associated pathologies in said transgenic mouse.

Yet another embodiment of the invention is a method in which an agent is administered to an IL-5 transgenic mouse of the invention. Preferably, the transgenic mouse comprises a chimeric DNA sequence comprising a thymocyte and/or T cell specific transcription control sequence operatively linked to a DNA segment which encodes interleukin-5. The DNA segment lacks any endogenous interleukin-5 control sequences which are 5' to the interleukin-5 coding sequence. The DNA segment is expressed as interleukin-5 in the transgenic mouse. After administering the agent, it is determined whether the agent reduces or inhibits interleukin-5 expression in the transgenic mouse relative to a transgenic mouse which has not received the agent ("control" mouse).

Another embodiment of the invention comprises a method in which an agent is administered to a transgenic mouse, the cells of which comprise a chimeric DNA sequence comprising a lung specific transcription control sequence operatively linked to a DNA segment which encodes interleukin-5. The chimeric DNA sequence is preferably integrated into the genome of the cells of the transgenic mouse and is expressed as interleukin-5 in the transgenic mouse. It is then determined whether said agent reduces or inhibits interleukin-5 expression in the transgenic mouse relative to a control transgenic mouse.

Yet another embodiment of the invention comprises a method in which an agent is administered to a transgenic mouse, the cells of which comprise a chimeric DNA sequence comprising a basal keratinocyte specific transcription control sequence operatively linked to a DNA segment which encodes interleukin-5. The chimeric DNA sequence is preferably integrated into the genome of the cells of the transgenic mouse and is expressed as interleukin-5 in the transgenic mouse. It is then determined whether said agent reduces or inhibits interleukin-5 expression in the transgenic mouse relative to a control transgenic mouse.

BRIEF DESCRIPTION OF THE FIGURES

FIGS. 5A–D. Cell differentials of bone marrow (A and B) and spleen (C and D) derived hematopoietic cells. Brush smear preparations of disassociated cells were stained with Wright-Giemsa prior to microscopy. The data from each tissue are presented in tabular form (A and C) and include total cellularity, individual progenitor and mature cell type percentages, and the absolute number of cells representing different stages of eosinophil differentiation. The tables provide data from wild-type (+/+) and NJ.1638 mice. Values appearing as exponents represent the number of measurements (i.e., animals) used to generate the data listed in the table. The table values in parentheses are the standard deviations associated with the measured and/or calculated numbers listed. *Mononuclear cell types include lymphocytes and monocytes/macrophages. ¶Only cells of the eosinophil lineage subtype class II, class III, and class IV were scored as marrow eosinophils. The description of the classes of cell types leading to and including mature eosinophils is found in the Detailed Description. ¶The number of cells in each class of eosinophil lineage cell type was calculated using the total cell counts and percentages listed in the tables as well as percentages derived from differentials of only eosinophil lineage cells: If £=the total number of eosinophil lineage cells (class I+class II+class III+class IV) then the total number of class I cells equals [£]×[percent class I cells derived from an eosinophil lineage differential]. Since the total number of (class II+class III+class IV) cells=[percent (%) tissue eosinophils]×[total WBC count], then {=[£]× [percent class I cells derived from eosinophil lineage differential]}+[percent (%) tissue eosinophils]×[total WBC count]. Therefore, £={[percent (%) tissue eosinophils]× [total WBC count]}÷{1–[percent class I cells derived from eosinophil lineage differential]}. The number of cells in each class of eosinophil lineage cell type was calculated by multiplying £ by the percentages of each cell type derived from the eosinophil lineage differentials. The graphs below each table represent histogram-like plots of the absolute numbers of cells in each eosinophil lineage class type/10$^6$ total tissue WBCs. The data presented represent average values of all age groups examined. The thumb print photographs are representative Wright-Giemsa stained cells of each granulocytic/eosinophil lineage class type.

DETAILED DESCRIPTION OF THE INVENTION

Figure 1:
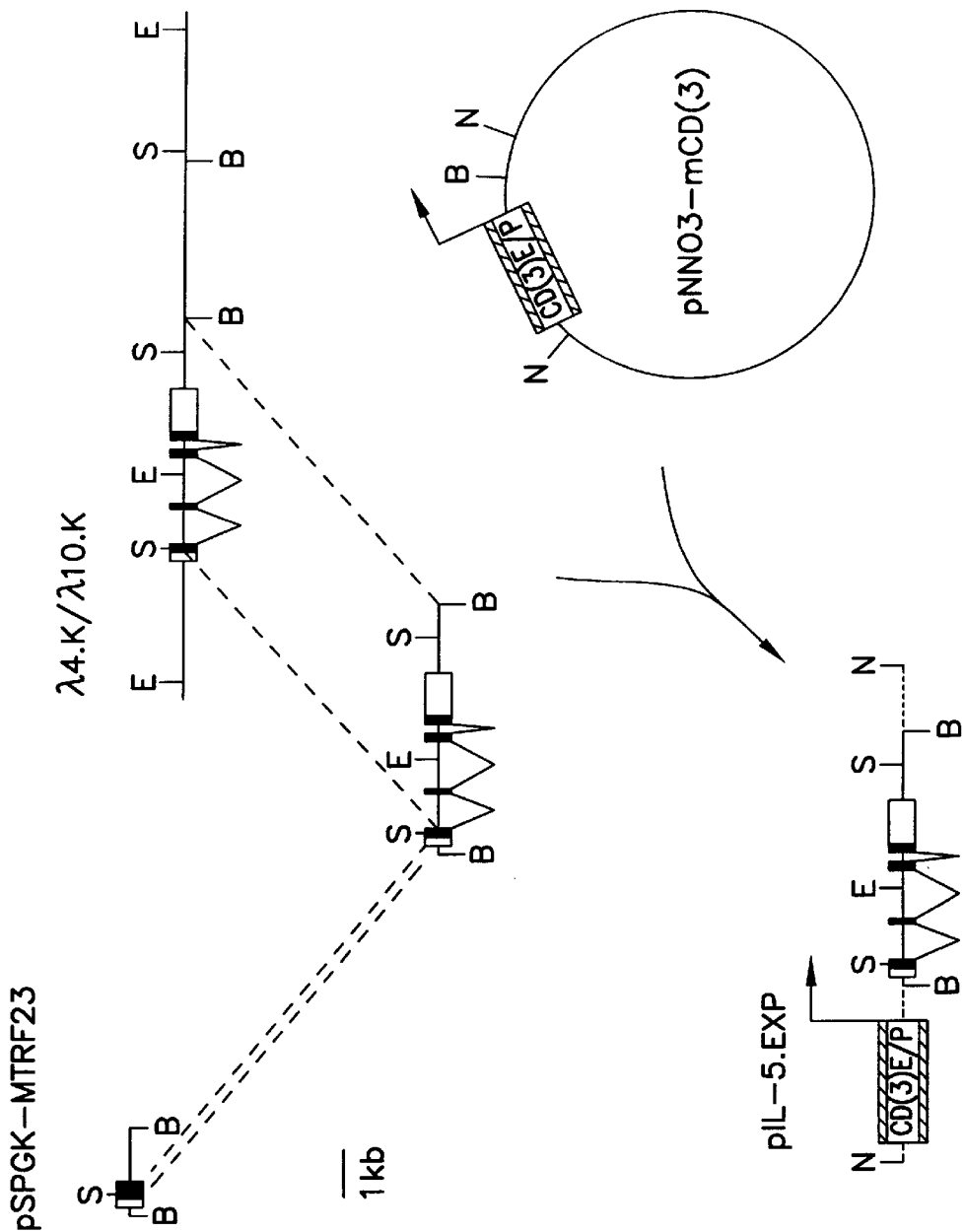
FIG. 1. Preparation of the IL-5 thymocyte/T cell transgene construct. The mini-gene construct was created as a cDNA:genomic fusion of sequences representing murine IL-5. Thymocyte/T cell specific expression of this fusion gene was achieved utilizing the basal promoter and tissue-specific enhancer (SEQ ID NO:3) of the murine CD3δ gene. The completed construct was cloned into the transgenic shuttle vector pNNO$^3$ and the 5.6 kb transgene insert was excised with NotI prior to introduction into fertilized eggs.

Transgenic animals which express a cytokine in a tissue and/or cell specific manner can be models for disease states associated with expression of that cytokine in those tissues or cells, as well as models for the efficacy of therapeutic agents which can be useful to treat those diseases. For example, transgenic mice expressing IL-5 from lung specific transcription control sequences, e.g., promoters and/or enhancers expressed in Clara cells in the lung (CC10) or in type II pneumocytes (SPC), can be useful as a model for diseases characterized by the presence of pulmonary eosinophilic infiltrations: asthma (extrinsic or intrinsic), pulmonary eosinophilia, Loffler's syndrome, eosinophilic pneumonia, eosinophilic myalgia, atopic disease, e.g., allergies or asthma, emphysema, pulmonary fibrosis, Wegener's granulomatosis, lymphoidmatoid granulomatosis, eosinophilic granuloma of the lung, adult respiratory distress syndrome, and post-trauma pleural effusions which contain eosinophils or eosinophil containing pleural effusions associated with infections, such as tuberculosis (see Spry, In: Eosinophils, Oxford University Press, pp. 205–212 (1988)).

Moreover, transgenic mice expressing IL-5 from a thymocyte and/or T cell specific transcription control sequence, e.g., CD2 and CD36, can be useful as a model for diseases that are associated with T cell expression of IL-5; bacterial infections, e.g., Actinomycetales, Enterobacteriaceae, Staphylococcal, and Streptococcal infections, fungal infections, e.g., Aspergillosis and fungal lung diseases, leukemias, e.g., eosinophilic leukemia, myelocytic leukemia, myeloblastic leukemia, Hand-Schuller-Christian disease, Letterer-Siew disease, Ornenn's syndrome, Well's syndrome, Kimura's disease, rheumatoid arthritis, Sjogren's syndrome, pulmonary eosinophilia, acute and chronic bronchitis. asthma, and the like (For an exhaustive list of these diseases, which are well known to the art, see Spry, In: Eosinophils, Oxford University Press, (1988)).

Transgenic mice expressing IL-5 from keratinocyte (skin) specific transcription control sequences, e.g., the K14 promoter and/or enhancer, can be useful as a model for atopic dermatitis, eosinophilic fasciitis, eosinophilia myalgia, contact hypersensitivity diseases, or any skin allergic or hypersensitivity reaction.

Furthermore, such transgenic animals can be employed as vehicles to test agents which are known to, or which may be useful to, reduce or inhibit the expression of IL-5 in vivo. Agents which inhibit eosinophil-associated pathologies and thus, which may act by inhibiting IL-5 production, are known to the art.

"Isolated cytokine nucleic acid" is RNA or DNA containing greater than 15, preferably 20 or more, sequential nucleotide bases that encode a cytokine, e.g., interleukin-5, or a variant fragment thereof having biological activity, that is complementary to the non-coding strand of the native cytokine RNA or DNA, or hybridizes to said RNA or DNA and remains stably bound under stringent conditions. Thus, the RNA or DNA is isolated in that it is free from at least one contaminating nucleic acid with which it is normally associated in the natural source of the nucleic acid and is preferably substantially free of any other mammalian RNA or DNA. The phrase "free from at least one contaminating source nucleic acid with which it is normally associated"

includes the case where the nucleic acid is reintroduced into the source or natural cell but is in a different chromosomal location or is otherwise flanked by nucleic acid sequences not normally found in the source cell. An example of isolated interleukin-5 nucleic acid is RNA or DNA that encodes a biologically active interleukin-5 polypeptide sharing at least 80%, preferably at least 90%. sequence identity with the murine interleukin-5.

As used herein, the term "recombinant nucleic acid," i.e., "recombinant DNA" refers to a nucleic acid, i.e., to DNA that has been derived or isolated from any appropriate tissue source, that may be subsequently chemically altered in vitro, and later introduced into target host cells, such as cells derived from animal, plant, insect, yeast, fungal or bacterial sources. An example of recombinant DNA "derived" from a source, would be a DNA sequence that is identified as a useful fragment encoding a cytokine, or a fragment or variant thereof, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Therefore, "recombinant DNA" includes completely synthetic DNA sequences, semi-synthetic DNA sequences, DNA sequences isolated from biological sources, and DNA sequences derived from introduced RNA, as well as mixtures thereof. Generally, the recombinant DNA sequence is not originally resident in the genome of the host target cell which is the recipient of the DNA, or it is resident in the genome but is not expressed, or not highly expressed in a cell-specific manner.

As used herein, "chimeric" means that a vector comprises DNA from at least two different species, or comprises DNA from the same species, which is linked or associated in a manner which does not occur in the "native" or wild type of the species.

The recombinant DNA sequence, used for transformation herein, may be circular or linear, double-stranded or single-stranded. Preferably, it is linear and double stranded DNA. Generally, the DNA sequence is in the form of chimeric DNA, such as plasmid DNA, that can also contain coding regions flanked by control sequences which promote the expression of the recombinant DNA present in the cells into which the DNA is introduced. For example, the recombinant DNA may itself comprise a promoter that is active in mammalian cells, or may utilize a promoter already present in the genome that is the target for the introduction of the recombinant DNA. Such promoters include the CMV promoter, as well as the SV40 late promoter and retroviral LTRs (long terminal repeat elements). A preferred embodiment of the invention includes promoters and/or enhancers which result in cell- or tissue-specific expression. Preferred thymocyte/T cell-specific transcription control sequences include, but are not limited to, CD3δ and CD2. Preferred lung specific transcription control sequences include, but are not limited to CC10 and SPC. Cell- and/or tissue-specific transcription control sequences are well known to the art. Aside from recombinant DNA sequences that serve as transcription units for the cytokine or portions thereof, a portion of the recombinant DNA may be untranscribed, serving a regulatory or a structural function.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is generally accomplished by ligation at convenient restriction sites. If such sites do not exist, the synthetic oligonucleotide adaptors or linkers are used in accord with conventional practice.

Aside from recombinant DNA sequences that serve as transcription units for a cytokine or portions thereof, a portion of the recombinant DNA may be untranscribed, serving a regulatory or a structural function.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the introduced DNA in the cell or its progeny.

The general methods for constructing recombinant DNA which can be introduced into target cells are well known to those skilled in the art, and the same compositions and methods of construction may be utilized to produce the DNA useful herein. For example, J. Sambrook et al., *Molecular Cloning: A Laboratory Manual,* Cold Spring Harbor Laboratory Press (2d ed., 1989), provides suitable methods of construction.

The recombinant DNA can be readily introduced into the target cells, i.e., totipotent cells such as fertilized eggs, by methods well known to the art. For example, see Cordell, U.S. Pat. No. 5,387,742, issued Feb. 7, 1995, which is incorporated by reference herein. Although defined primarily by reference to mice, the constructs described herein can be used to produce other non-human mammalian transgenic species, including, but not limited to, rats, hamsters, sheep, pigs, rabbits, gerbils, cats, dogs, bovines, primates and the like.

"Southern analysis" or "Southern blotting" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled,. biotinylated, or enzyme-labeled probe as described in sections 9.37–9.52 of Sambrook et al., supra.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as $^{32}P$, by biotinylation or with an enzyme. The RNA to be analyzed can be usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Ouant. Biol.,* 51, 263 (1987); Erlich, ed., *PCR Technology,* (Stockton Press, NY, 1989).

"Stringent conditions" are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0. 1% Ficoll/ 0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 $\mu$g/ml), 0.1% SDS, and 10% dextran sulfate at 42° C., with washes at 42° C. in 0.2×SSC and 0.1% SDS. These abbreviations are defined in Sambrook et al., supra.

The invention will be further described by reference to the following examples.

EXAMPLE I

Materials and Methods

Generation and identification of transgenic mice.

Murine IL-5 containing DNA fragments (Tohyama et al., *EMBO J.* 9, 1823 (1990)) were cloned in the plasmid vector pBluescript-KS(+) (Stratagene, La Jolla, Calif.) or the transgenic plasmid shuttle vector pNNO3 as part of the construction of the murine IL-5 cDNA:genomic fusion gene (SEQ ID NO:4:SEQ ID NO:5). This minigene, together with the transcriptional regulatory elements of the murine CD3$\delta$ gene (SEQ ID NO:3) were excised free of plasmid vector sequences using Not I and gel purified by electroelution onto dialysis membrane. The purified insert DNA was filtered using centrifuge microfiltration units (0.2 $\mu$M; Schleicher and Schuell, Keene, N.H.) prior to injection into fertilized eggs derived from a cross of $F_1$ (CBA/J X C57BL/6J) females and C57BL/6J males.

Transgenic positive founder animals were identified from Southern genomic blots of tail DNA using a $^{32}$P-labeled random primed IL-5 cDNA probe. Subsequent generations of mice were the result of backcross onto either C57BL/6J or $F_1$ (CBA/J X C57BL/6J) hybrid mice and identification of transgenic positive offspring was accomplished by genomic Southern blot analysis and an IL-5 transgene-specific PCR based assay. The primers employed in the PCR based assay were derived from the CD3$\delta$ regulatory sequences (sense primer) and sequences from the first exon of the IL-5 gene (anti-sense primer). Sense primer: 5' ACCCCACAC-CTAGCCCACTG 3' (SEQ ID NO:1); anti-sense primer: 5' TGGCAGTGGCCCAGACACAGC 3' (SEQ ID NO:2). The final PCR reaction conditions were: ~200 ng genomic tail DNA, 2 mM MgCl$_2$, 400 $\mu$M of each dNTP, 0.2 $\mu$M of each oligonucleotide primer, 1×PCR Buffer II (Perkin-Elmer, Foster City, Calif.), and 2.5 units of Taq polymerase (Boehringer Mannheim, Indianapolis, Ind.). The reactions were routinely carried out in a volume of 50 $\mu$l using the Gene Amp PCR System 9600 (Perkin-Elmer, Foster City, Calif.). The reaction program used consisted of an initial denaturation step of 94° C. for 5 minutes, followed by 30 cycles of the repeating series 94° C. for 1 minute, 55° C. for 1 minute, and 72° C. for 2 minutes. The reactions were completed with a 72° C. +0 minute extension period.

For lung-specific expression of IL-5, a 2.3 kb BamHI restriction fragment comprising the promoter of the rat Clara cell secretory protein "CC10" gene (Hackett and Gitlin, *Proc. Natl. Acad. Sci. USA,* 89, 9079 (1992)) was linked to the cDNA:genomic fusion of IL-5 (Lee et al., *J. Immunol.,* 158, 1332 (1997)). The expression vector was prepared by cloning a BamHI restriction fragment containing a 5.5 kb IL-5 cDNA/genomic fusion gene into the BglII site of the plasmid pNNO3 (Biogen, Cambridge, Mass.). The 2.3 kb BamHI fragment containing the promoter region of the rat CC10 gene was cloned into an upstream BamHI site in the polylinker of this plasmid. This transgenic construct was excised from plasmid sequences by Not I digestion and injected into embryos derived from a cross of $F_1$ (CBA/CaJ X C57BL/6J) females and C57BL/6J males. Transgenic positive founder animals were identified from genomic Southern blots of tail DNA. Subsequent generations of transgenic animals were the result of backcrosses onto the inbred strain C57BL/6J.

Animals were maintained in micro-isolator cages housed in a specific pathogen-free (SPF) animal facility. The sentinel cages within the animal colony surveyed negative for viral antibodies and the presence of known mouse pathogens.

RNA isolation and Northern blot analysis.

Total RNA was prepared from cell populations and tissues using a guanidine thiocyanate-acid phenol extraction protocol. The high RNase content of infiltrating eosinophils necessitated two modifications of this standard protocol to purify intact RNA: the reducing agent dithiothreitol (DTT; Sigma, St. Louis, Mo.) was added at very high concentrations (0.2–0.5 M) and the volume of lysis buffer relative to the mass of tissue homogenized was increased several fold. Total RNA (15 $\mu$g) from each source was fractionated by gel electrophoresis on a 1.2% agarose gel containing formaldehyde and transferred to GeneScreen (+) per the instructions of the manufacturer (NEN-Dupont. Boston, Mass.). The filter was pretreated for 2 hours at 45° C. in a solution containing 5×SET (1×SET is 0.15 M NaCl, 30 mM Tris-HCl pH 8.0, and 2 mM EDTA), 10×Modified-Denhardts and 50 mM phosphate buffer (1 M phosphate buffer contains 69 g of sodium monobasic phosphate and 134 g of sodium dibasic phosphate per liter). Following pretreatment, this solution was discarded and the filter was prehybridized and hybridized under the stringent conditions described below.

Initially, the filter was incubated with gentle agitation at 45° C. for 2 hours in 50% deionized formamide (Boehringer Mannheim, Indianapolis, Ind.), 5×SET, 1×Modified-Denhardts, 20 mM phosphate buffer, 2% SDS, and 100 $\mu$g/ml sheared and denatured salmon sperm DNA (Sigma, St. Louis, Mo.). This prehybridization buffer was subsequently discarded and the filter hybridized overnight at 45° C. in fresh buffer containing 3–5 ng/ml of a $^{32}$P-labeled random primed probe. The hybridized filter was washed as follows: the filter was rinsed several times with 4× SSC-1% SDS at room temperature and then washed at 65° C., first for 2×20 minutes in 4×SSC-1% SDS, then for 2×20 minutes in 1×SSC-0.2% SDS, and finally for 2×20 minutes in 0.1× SSC-0.2% SDS. Hybridization was visualized by autoradiography using Kodak XAR-5 x-ray film (Eastman Kodak, Rochester, N.Y.).

Serum IL-5 ELISA.

Peripheral blood (300–500 mm$^3$) was recovered by nicking the tail artery. Blood was collected in a 1.5 ml microcentrifuge tube and allowed to clot without agitation at room temperature for 30 minutes. The clotted blood was centrifuged at ~000 rpm for 10 minutes at 4° C. to recover serum which was then frozen on dry ice and stored at −80° C. until use. IL-5 levels were measured in these serum samples using a murine-specific IL-5 ELISA kit from Endogen, Inc. (Boston, Mass.). Measurements were made either on direct serum samples or serum diluted with the diluent provided by the manufacturer. Calorimetric assays associated with this ELISA were performed using a Molecular Devices V max microplate reader.

Fluorescence activated cell scanning (FACS) analysis.

Peripheral blood (50–100 μl) was collected from the tail and diluted directly into 4 ml of 1×PBS. Cells were collected by centrifugation at 1000 rpm for 5 minutes at 4° C. and red blood cells (RBC) were removed by resuspending the cell pellets in 0.5 ml of RBC lysis buffer (0.15 M ammonium chloride, 10 mM potassium bicarbonate, 0.1 mM EDTA) and incubating for 5 minutes at 4° C. The lysed samples were diluted with 4 ml of 1×PBS containing 1% BSA and 0.1% sodium azide (PBS/BA) and white blood cells (WBC) were collected by low speed centrifugation as described above. The WBC pellets were cleared of remaining cellular debris by an additional cycle of resuspension in 4 ml of PBS/BA followed by low speed centrifugation. This WBC pellet was resuspended in 0.1 ml of 1×PBS containing 0.1% sodium azide (PBS/A) and lymphocytes were stained by incubating for 20 minutes with anti-CD3ε conjugated with fluorescein isothiocyanate (FITC), anti-CD45R (B220) conjugated with phycoerythrin (PE), and biotinylated anti-CD45. All antibodies were purchased from Pharmingen (San Diego, Calif.).

The stained cells were collected by low speed centrifugation and unbound antibody was removed by a single cycle of resuspension in 4 ml of PBS/BA and low speed centrifugation. The cells were resuspended in 0.1 ml of PBS/BA and stained for 20 minutes with streptavidin-613 (Gibco-BRL, Bethesda, Md.) and unbound streptavidin was then removed by a single wash cycle with 4 ml of PBS/BA. The final cell pellet was resuspended in 0.5 ml of 1×PBS containing 1% formaldehyde and 0.1% sodium azide and stored at 4° C. until FACS analysis. Flow cytometry was performed using a FACSvantage cytometer and CELLQuest software (Becton-Dickinson). Lymphocytes were identified as CD45 positive cells in a gated population based on forward and side scatter profiles. The fractions of this population that were CD3e positive (T cells) or CD45R positive (B cells) were determined from sample analyses in which a minimum of 15,000 cells were acquired.

Tissue histology.

Experimental animals were sacrificed by lethal injection or $CO_2$ asphyxiation prior to organ/tissue harvest. Biopsies for histology were fixed overnight in 10% phosphate-buffered formalin at room temperature. The fixed tissue samples were subsequently carried through an ascending ethanol series before equilibration in xylene and paraffin impregnation. Paraffin sections (6 μM) were stained with hematoxylin and eosin and photomicrography was accomplished with a Ziess Axiophot microscope using Kodak Ectochrome 100 film (Eastman Kodak, Rochester, N.Y.).

EXAMPLE II

T Cell Specific Expression of IL-5

Constitutive expression of IL-5 in a peripheral lymphocyte population was achieved with a cDNA:genomic IL-5 fusion gene using the murine CD3δ promoter and enhancer (FIG. 1). This IL-5 transgene was designed to mimic the systemic pattern of IL-5 gene activity (i.e., elevated peripheral lymphocyte expression) as determined from models of parasite infestation and clinical studies of allergic inflammation. The transgene construct directs peripheral T cell expression, uncoupled from factors that mediate endogenous IL-5 gene activity, as a consequence of two structural features.

The transgene construct was made by fusing in-frame a 170 bp fragment derived from the IL-5 cDNA (SEQ ID NO:4) with the remaining portion of the genomic IL-5 gene (SEQ ID NO:5). Since the point of fusion was in exon 1, this hybrid gene has no upstream flanking sequences but includes all of the introns of the IL-5 gene as well as ~1.2 kb of 3'-flanking sequences. The transgene is thus devoid of all the known endogenous regulatory elements associated with IL-5 expression (Bourke et al., Blood, 85, 2069 (1995)) while retaining all of the structural features and sequences of the genomic IL-5 gene.

Peripheral T cell expression of this construct results from the use of regulatory elements derived from the murine CD3δ gene. CD3δ is a T cell specific cell surface protein that is part of the T cell receptor (TCR) complex and is involved in signaling mediated by major histocompatibility complex-TCR interactions. Expression studies of the CD3δ gene in both mice and humans have shown that this gene is activated during thymocyte maturation and continues to be expressed in all peripheral T cells. Hypersensitivity experiments and cell transfection studies showed that this pattern of expression was the result of an enhancer activity associated with an approximately 300 bp sequence in the flanking region downstream of the CD3δ gene. The utility of this enhancer element to drive peripheral T cell specific expression in transgenic mice has been demonstrated in studies which showed that by linking the CD3δ 3'-enhancer and the CD3δ basal promoter into one contiguous sequence, a regulatory element was created that is sufficient to drive expression of heterologous reporter genes in a temporal and spatial manner identical to the endogenous CD3δ gene. As a result, this IL-5 transgene construct promotes peripheral T cell expression of this cytokine, free from the influences of factors that regulate endogenous IL-5 expression.

EXAMPLE III

Generation and Characterization of Transgenic Mice Expressing IL-5 in Peripheral T Cells Several independent lines of transgenic mice were created using the CD3δ/IL-5 minigene construct. Three partially characterized lines of mice (NJ.759, NJ.1638, NJ.1643) were each found to contain integrations of 2–5 copies of this construct. In addition, individuals from each line of mice also exhibited a common set of phenotypic traits: dramatically elevated white blood cell (WBC) counts, peripheral blood eosinophilia (both in terms of eosinophil numbers and as a percentage of WBC), and the development of histopathologies that compromise the health and reproductive capabilities of these animals. To investigate further the pathophysiologic effects of peripheral expression of IL-5, one of these lines of mice (NJ.1638) was chosen for detailed study.

Figure 2A:
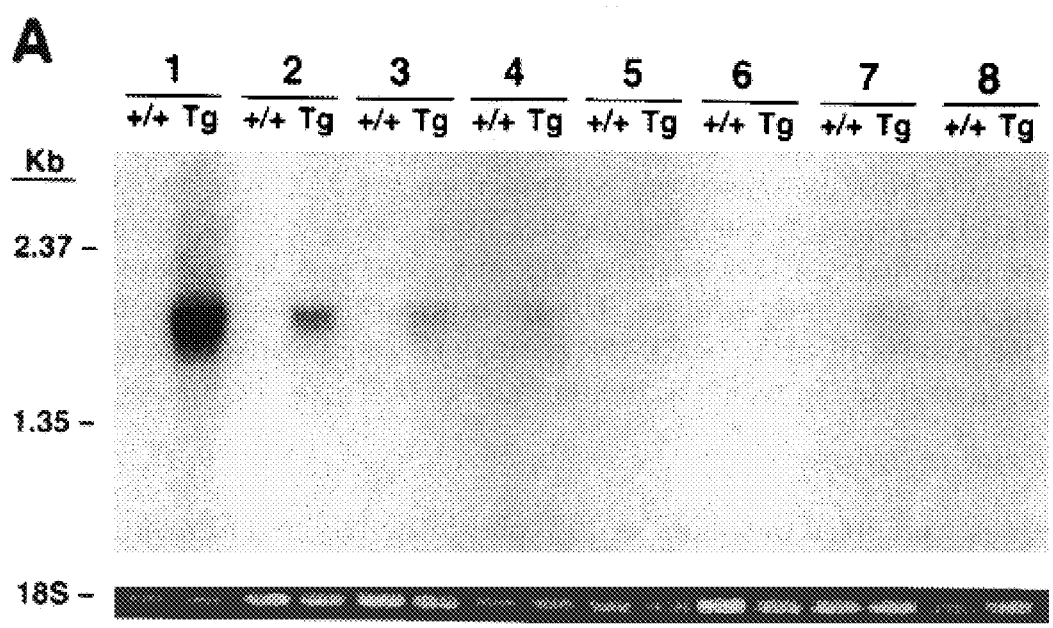
FIGS. 2A and 2B show Tissue-specific IL-5 gene expression and augmentation of IL-5 serum levels in transgenic mice. (A) Northern blot of wild-type C57BL/6J (+/+) and NJ.1638 transgenic (Tg) tissue RNAs probed with a random-primed $^{32}$P-labeled IL-5 cDNA. Each lane contains 15 μg of total RNA. Group 1, thymus; Group 2, bone marrow; Group 3, spleen; Group 4, lung; Group 5, leg muscle; Group 6, liver; Group 7, peritoneal cavity cells; Group 8, peripheral blood. A photograph of the 18S small ribosomal subunit stained with ethidium bromide is shown to verify the presence of RNA in each lane. (B) Quantitation of circulating serum protein levels using a murine-specific IL-5 specific capture ELISA. Serum IL-5 protein levels were assessed in wild-type mice at 7 months of age (+/+) and transgenic NJ. 1638 mice at 1, 4, 7, and 10 months postpartum. Serum IL-5 levels were also measured in 7 month old mice infested with the helminthic parasite *Mesocestroides corti*. The *M. corti* tetrathyridia were maintained by serial passages in mice. Female C57BL/6J mice (>19 gms, Roswell Park Animal Resources) were intraperitoneally injected with 100 μl of packed tetrathyridiae obtained from long-term infested mice. Peripheral blood samples were taken for IL-5 serum protein determination ten days post infestation.

The tissue-specific expression of IL-5 in NJ. 1638 mice was assessed by Northern blot analysis of total RNA derived from transgenic positive and age (7 months postpartum (p.p.)/sex (female)) matched normal (+/+) C57BL/6J mice (FIG. 2(A)). IL-5 transcripts were found in several of the NJ. 1638 tissues examined. In particular, as predicted by the previous characterization of the CD3δ enhancer-promoter IL-5 mRNAs were prevalent in the thymus. FIG. 2(A) also shows that IL-5 transcripts could be detected in peripheral sites known to contain sizable resident T cell populations (i.e., bone marrow, spleen, peritoneal cavity cells, lung, and blood). However, longer exposures of this blot showed that IL-5 transcripts can be detected even in tissues (i.e., liver and leg muscle) with only a small number of infiltrating T cells relative to the mass of tissue taken to make total RNA. Detectable steady-state levels of IL-5 mRNA were not found in any of the wild-type tissues examined.

Figure 2B:
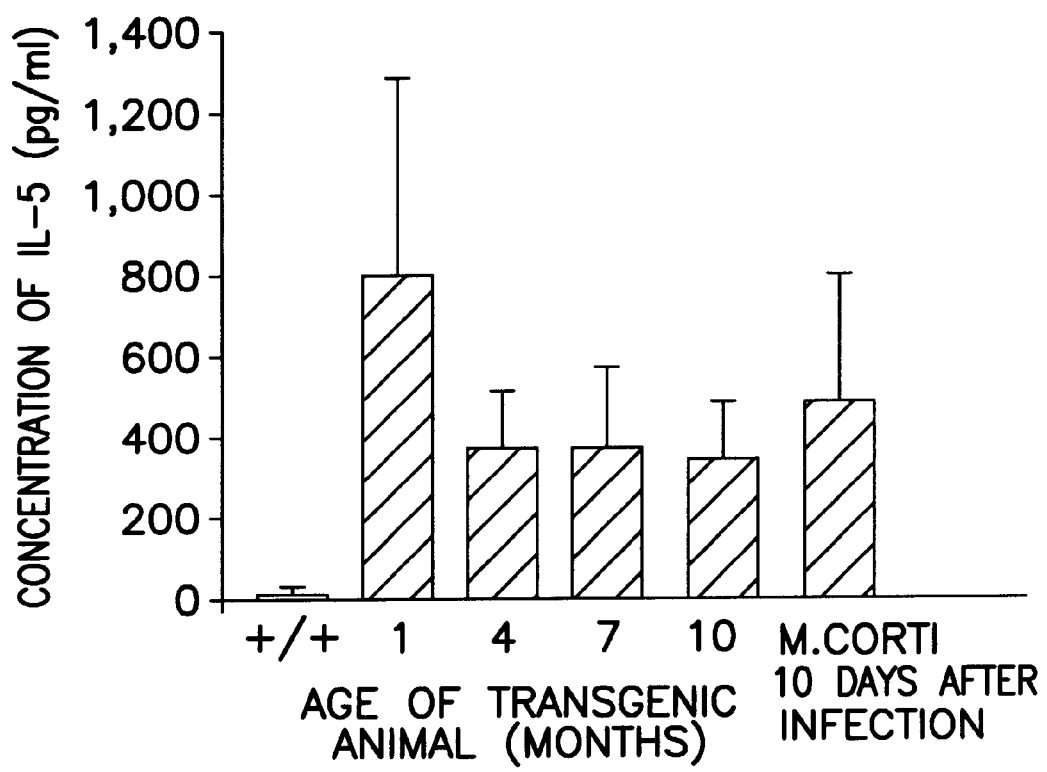

Circulating serum levels of IL-5 were measured in these transgenic mice as a function of postpartum age and the data are collected in the histograms contained in FIG. 2(B). A murine IL-5 specific ELISA (Endogen, Inc., Boston, Mass.) was used to measure serum IL-5 levels in transgenic, normal and parasite infested mice. IL-5 levels in the serum of wild-type (i.e., normal) animals were routinely at or below the level of detection of our assay ($\leq$2–5 pg/ml of serum). The data shown in FIG. 2(B) represents wild-type animals at 7 months of age. Circulating IL-5 levels remain at this low level in wild-type animals regardless of the age of the animal examined.

Serum IL-5 levels in transgenic animals, however, quickly elevated to very high levels in postpartum mice (800 pg/ml in one month old animals) before dropping slightly to a steady-state serum level of approximately 400 pg/ml which was maintained throughout the life of the animal. The final histogram of FIG. 2B shows that the NJ.1638 steady-state serum IL-5 level was equal to the highest IL-5 levels found in wild-type mice infested with the helminthic parasite *M. corti* (10 days postinfestation).

EXAMPLE IV

Peripheral Eosinophilia and Other Alterations in Blood Leukocyte Populations IL-5 overexpression in other characterized IL-5 transgenic mouse lines had previously shown that this cytokine induces a dramatic expansion of the number of blood eosinophils with only nominal effects on other mature leukocyte cell types (Tominaga et al., *J. Exp. Med.*, 173, 424 (1991); Dent et al., *J. Exp. Med.*, 172, 1425 (1990)). Consequently, eosinophil numbers, as a percentage of WBC, rose in these mice to as high as 60%. In addition, these expansions were also accompanied by mild increases in total WBC counts (3- to 7-fold).

Figure 3A:
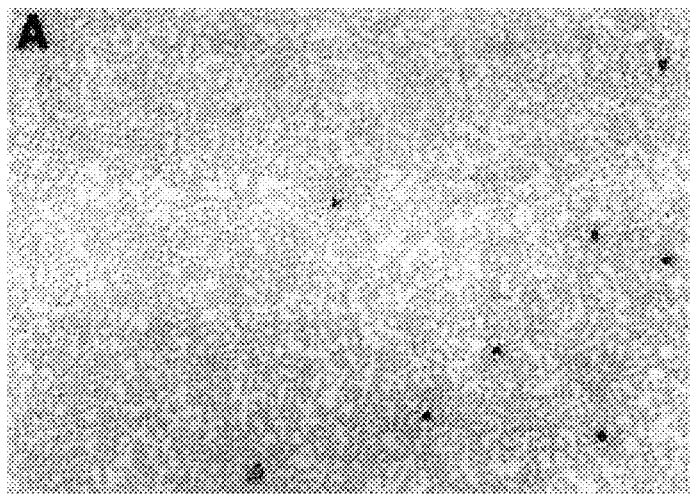
FIGS. 3A and 3B. Peripheral blood smears of 7 month old C57BL/6J (+/+) (A) and NJ.1638 transgenic (B) mice. Single-animal smear preparations were prepared from tail vein blood. The photographs shown are representative regions of equal cell density (i.e., equal red blood cell densities) stained with Wright-Giemsa.
Figure 3B:
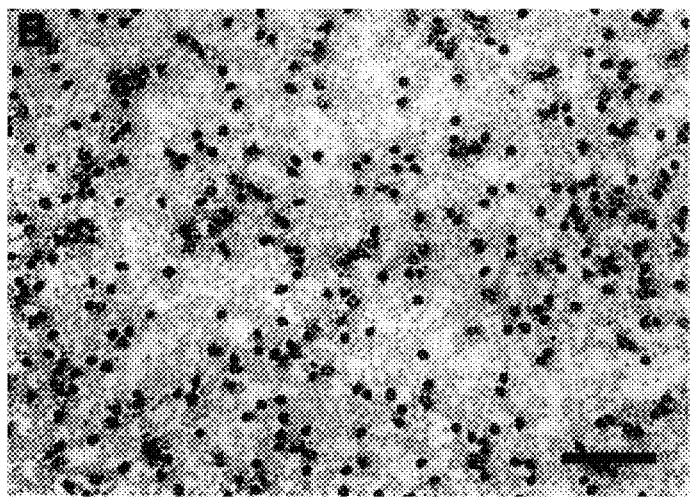

A similar phenomena was observed in NJ.1638 animals, although the effects of high-level peripheral IL-5 expression in these mice has far greater consequences than those observed in previous reports. FIG. 3 contains representative photographs of peripheral blood smears derived from wild-type and NJ.1638 mice. The transgenic mice suffered from both an obvious peripheral eosinophilia as well as a large increase in total WBC. The quantitative significance of these effects are shown in the blood differential data collected in Table 1.

The total WBC counts and cell differentials included in this Table are derived from wild-type and NJ.1638 transgenic animals at different postpartum ages. The generation of CD3$\delta$ positive peripheral T cells in the mouse begins late in gestation approximately 17.5 days post coitum. As a result, elevated IL-5 expression begins prior to birth and the hematological consequences of this expression should be evident early in postpartum age. As shown in Table 1, the onset of effects induced by peripheral expression of IL-5 occurred by one month of age resulting in total WBC counts of these animals >55,000 cells/mm$^3$ of blood (i.e., greater than a 7-fold increase over wild-type animals). The percentage of cells that are eosinophils in these animals also increased from a basal level of 1% to 47% of total WBC. Moreover, transgenic positive newborns of transgenic negative mothers had WBC cellularities >30,000 cells/mm$^3$ with a peripheral eosinophilia of 30%. As the transgenic mice got older, this remarkable deviation from the normal cellularity of wild-type animals continued to expand virtually unabatedly. The total cellularity of the blood increased so that by 15 months of age NJ.1638 animals had an average peripheral WBC count greater than 40-fold over wild-type (476,880 cells/mm$^3$ of blood). Eosinophil levels in these mice also increased to 64% of total WBC (i.e. >300,000 eosinophils/mm$^3$).

TABLE 1

| age (months) | mouse | hematocrit | cell number/mm$^3$ of blood (X 10$^{-3}$) | | | | | percentage of each cell type | | | |
|---|---|---|---|---|---|---|---|---|---|---|---|
| | | | total | lymphocyte | monocyte | eosinophil | neutrophil | lymphocyte | monocyte | eosinophil | neutrophil |
| 1 | +/+ | 47.6 | 7.54 | 6.00 | 0.80 | 0.07 | 0.67 | 77.8 | 10.6 | 0.8 | 10.8 |
| | | (0.6)[5] | (3.23)[5] | (3.00) | (0.34) | (0.08) | (0.29) | (5.9) | (1.8) | (0.8) | (6.5) |
| | NJ. 1638 | 51.5 | 55.23 | 24.67 | 1.11 | 26.51 | 3.00 | 46.2 | 2.0 | 46.8 | 5.2 |
| | | (4.7)[12] | (12.54)[4] | (8.04) | (1.00) | (11.69) | (3.04) | (15.4) | (1.8) | (13.8) | (4.4) |
| 4 | +/+ | 52.0 | 13.43 | 10.88 | 0.56 | 0.42 | 1.55 | 80.6 | 4.4 | 3.0 | 12.0 |
| | | (2.9)[7] | (3.32)[7] | (2.98) | (0.35) | (0.32) | (0.40) | (5.1) | (2.9) | (2.0) | (3.5) |
| | NJ. 1638 | 53.0 | 86.20 | 40.76 | 1.21 | 40.28 | 3.84 | 47.5 | 1.4 | 46.2 | 4.8 |
| | | (4.0)[8] | (33.08)[8] | (15.94) | (1.40) | (18.11) | (1.95) | (7.4) | (1.4) | (6.4) | (2.2) |
| 7 | +/+ | 43.7 | 12.30 | 9.43 | 0.80 | 0.37 | 1.70 | 73.6 | 5.6 | 4.2 | 16.7 |
| | | (2.5)[3] | (6.00)[3] | (5.3) | (0.72) | (0.25) | (1.08) | (17.4) | (2.9) | (4.7) | (14.0) |
| | NJ. 1638 | 49.0 | 245.80 | 113.34 | 0.34 | 159.92 | 5.32 | 45.1 | 0.4 | 50.7 | 3.7 |
| | | (5.4)[5] | (180.54)[4] | (89.02) | (0.76) | (81.21) | (2.39) | (4.2) | (0.9) | (6.5) | (3.5) |
| 10 | +/+ | 48.9 | 8.50 | 6.43 | 0.62 | 0.10 | 1.36 | 76.6 | 8.0 | 1.8 | 13.4 |
| | | (3.8)[9] | (6.28)[9] | (4.46) | (0.43) | (0.10) | (1.55) | (9.0) | (3.7) | (2.3) | (7.0) |
| | NJ. 1638 | 42.8 | 331.64 | 153.01 | 3.16 | 166.17 | 8.46 | 46.3 | 0.7 | 50.0 | 2.9 |
| | | (3.5)[10] | (250.82)[8] | (126.36) | (4.63) | (142.92) | (9.78) | (12.1) | (0.8) | (11.2) | (1.9) |
| 11 to 14 | +/+ | 44.8 | 7.40 | 5.68 | 0.32 | 0.34 | 1.02 | 76.2 | 4.6 | 4.0 | 14.3 |
| | | (1.9)[5] | (4.32)[5] | (3.33) | (0.16) | (0.32) | (0.68) | (4.5) | (2.0) | (1.3) | (5.0) |
| | NJ. 1638 | 38.5 | 390.67 | 146.63 | 4.91 | 224.62 | 13.37 | 37.5 | 1.7 | 56.9 | 3.8 |
| | | (4.6)[26] | (261.92)[29] | (115.33) | (7.08) | (161.35) | (17.08) | (14.0) | (2.7) | (14.6) | (3.7) |
| 15 to 17 | +/+ | 43.8 | 12.20 | 9.68 | 0.84 | 0.30 | 1.42 | 73.8 | 9.2 | 2.3 | 14.8 |
| | | (1.8)[5] | (6.8)[5] | (6.93) | (0.37) | (0.21) | (0.31) | (12.6) | (6.1) | (1.0) | (7.7) |
| | NJ. 1638 | 35.4 | 476.88 | 153.71 | 12.09 | 330.18 | 10.77 | 30.4 | 2.8 | 64.1 | 2.7 |
| | | (5.5)[16] | (269.46)[16] | (110.96) | (11.12) | (181.71) | (10.77) | (1.46) | (2.2) | (12.9) | (2.5) |

Peripheral blood cell counts and differentials as a function of postpartum age. Values appearing as exponents represent the number of measurements (i.e., animals) used to generate the data listed in the table. The tabular values in parentheses are the standard deviations associated with the measured numbers listed.

The percentage increase of eosinophils in NJ.1638 mice occurred at the expense of other leukocytes whose fraction of total WBC decreased in each mature cell type. This observation, however, is misleading if the dramatic increases in total cellularity were not also taken into account. For example, neutrophils decreased from 5.2% of total WBC in one month old transgenic animals to 2.7% in 15–17 month old mice. In addition, each of these transgenic neutrophil percentages were lower than the average neutrophil percentage exhibited by wild-type mice (13.9%). However, because of the enormity of the increase in total WBC associated with NJ. 1638 animals, neutrophil counts in these mice actually went up throughout the life of the animals, increasing to 10,770 neutrophils/mm$^3$ of blood (15–17 months) or >10-fold over wild-type levels. Similar observations were made for all of the non-eosinophil cell populations examined. In each case, the percentage of a given cell type decreases relative to wild-type mice, but in absolute terms peripheral expression of IL-5 at high levels resulted in massive increases in the total number of each of these peripheral blood cell types.

Table 1 also shows that hematocrits derived from both wild-type and NJ.1638 animals remained virtually unchanged. As a result, despite the dramatic increase of total WBC in NJ.1638 mice, red blood cells levels appeared not to be effected. However, whereas the hematocrits (i.e., red blood cell counts) of wild-type mice remained constant throughout the lifetime of the animals, the hematocrits of the transgenic animals decreased marginally with time. This observation reflects either a generalized decrease in the health of these animals with age, or perhaps long-term effects of systemic IL-5 expression resulting in an age dependent change in erythropoiesis.

EXAMPLE V

Physiological Changes of the Spleen and Liver Are Associated With CD3δ Driven IL-5 Expression The elevated levels of IL-5 expression in NJ.1638 mice also appeared to have dramatic physiological effects on several organ systems. The most prominent of these effects occurs in organ systems that engage in extramedullary hematopoiesis during the life span of the mouse (e.g., spleen-adult hematopoiesis, liver-fetal hematopoiesis). In wild-type mice, the spleen is a small (~80 mg wet weight) lymphoid organ that acts as a reservoir for peripheral B and T cell populations as well as circulating leukocytes. However, the spleen is also an important source of hematopoietic stem cells and accounts for nearly 10% of the adult animal's total hematopoietic capabilities.

Figure 4A:
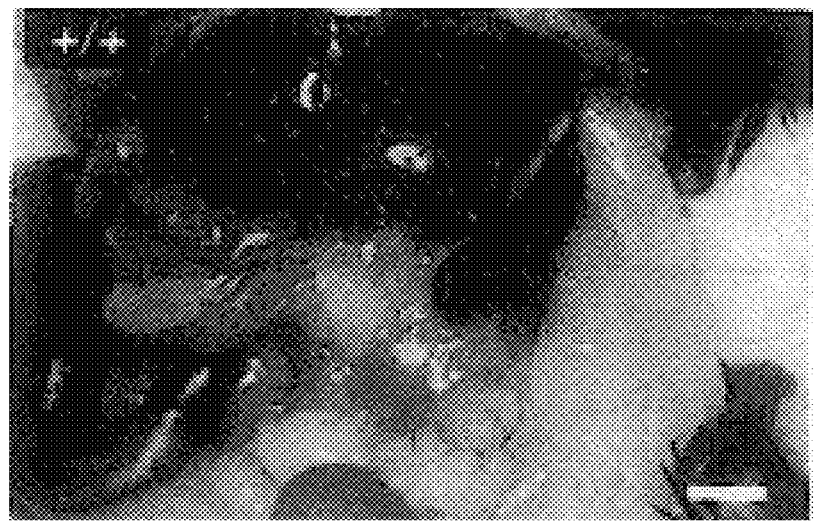
FIGS. 4A–G. Perturbations in spleen and liver structure/cellularity resulting from constitutive high-level expression of IL-5 in thymocytes/T cells. (A) Ventral view of the upper abdominal cavities of a 7 month old wild-type male (+/+) and an age and sex matched NJ.1638 mouse. The scale bar represents 0.5 cm. (B) Assessment of splenomegaly in NJ. 1638 mice as a function of postpartum age. Wild-type spleen weight (+/+) changed little in the time period examined. The wild-type spleen measurement shown are derived from animals 7 months of age. Spleen size is expressed as wet weight in mg. (C) Hematoxylin and eosin (H/E) stained transverse sections through the spleen of a wild-type (+/+) and age matched NJ.1638 mouse. The solid bar in the lower right corner equals 62.5 μM. (D) H/E stained transverse sections through the liver of a wild-type (+/+) and age matched NJ. 1638 mouse. The scale bar in the lower right corner equals 125 μM.
Figure 4B:

The effects of IL-5 expression on spleen size in NJ. 1638 mice are dramatically illustrated in FIGS. 4(A) and 4(B). The photographs found in FIG. 4(A) are ventral views of the upper abdominal cavity of a 7 month old wild-type mouse (+/+) in comparison to an age matched NJ.1638 mouse. Two effects on the spleen of transgenic mice were readily apparent. The spleen was enlarged in proportion to the expansion of the WBC counts of these animals. The wet weight of the transgenic spleen shown was 3.2 g (~40-fold increase over a wild-type spleen) and virtually filled the lower abdominal cavity.

A characterization of the splenomegaly that these mice suffer is shown in FIG. 4(B). These data quantify spleen growth in NJ. 1638 mice as a function of postpartum age. The kinetics of the observed splenomegaly is striking. The spleens of one month old animals were increased nearly 10-fold, averaging 680 mg in weight. The rate of expansion continued linearly with time throughout the life of the animal and as a result, by 10 months of age the average weight of a transgenic spleen was 1.93 g. To date, the largest of the spleen observed in an NJ.1638 mouse was a 5.28 g spleen (8 cm longitudinal axis) found in a 14 month old individual.

Figure 4C:
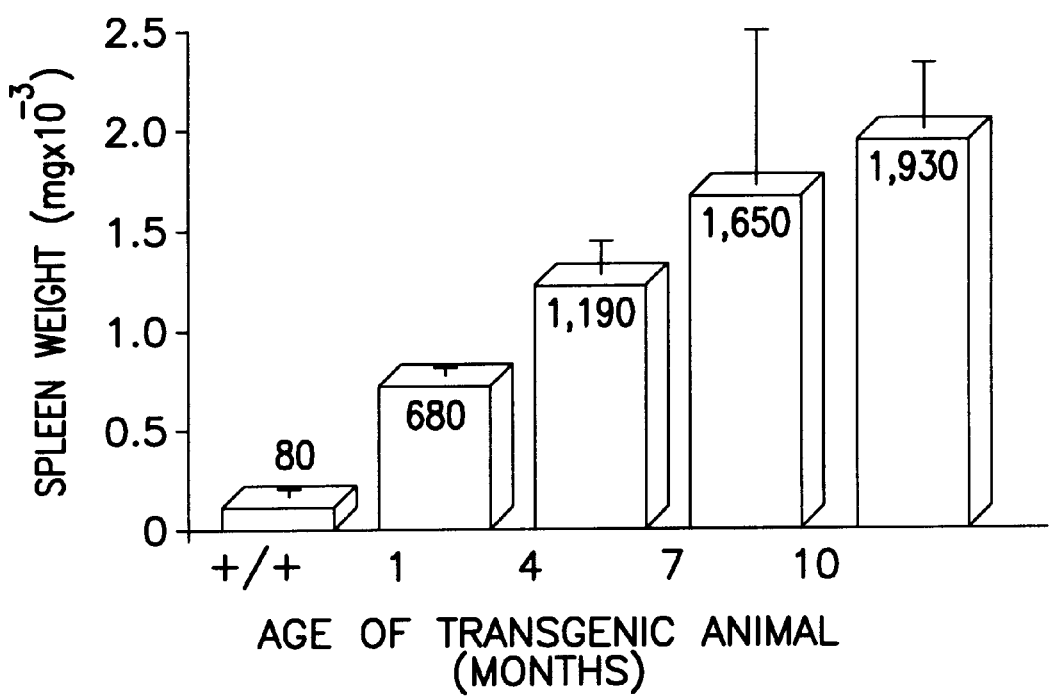

A closer examination of the transgenic spleen in FIG. 4(A) also revealed randomly distributed white patches or nodules suggesting the establishment of WBC foci and the exclusion of erythrocytes from these areas. The composition of these patches and the changes in transgenic spleen structure are shown in FIG. 4(C). FIG. 4(C) contains photographs of hematoxylin-eosin (H–E) stained tissue sections from wild-type spleen (+/+) and transgenic spleen (NJ.1638). The homeostatic red/white pulp structure of the wild-type spleen was clearly evident and the overwhelming majority of WBC in this spleen were mononuclear lymphocytes. The structural integrity and cell composition, however, was completely abolished in the transgenic spleen. In addition to the loss of red/white pulp boundaries, mature eosinophils and myeloid progenitor cells comprised a substantial fraction of total splenocytes and were distributed throughout the spleen. The white patches visible on the transgenic spleen apparently represented large areas in the spleen containing exclusively leukocytes predominated by mature eosinophils.

Figure 4D:
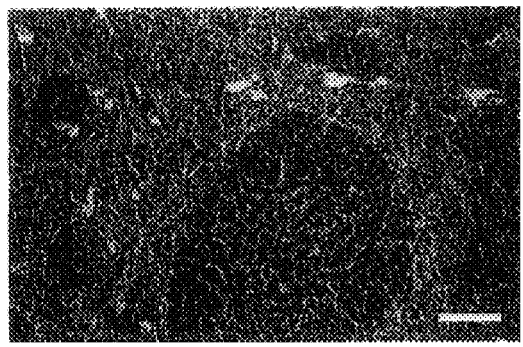
Figure 4E:
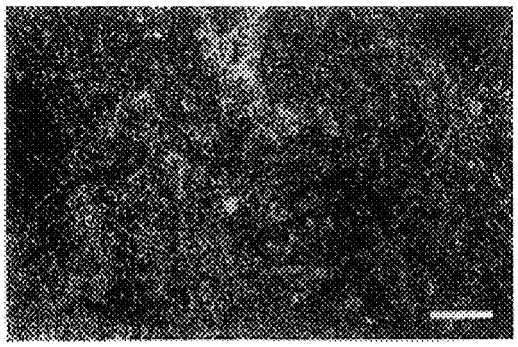
Figure 4F:
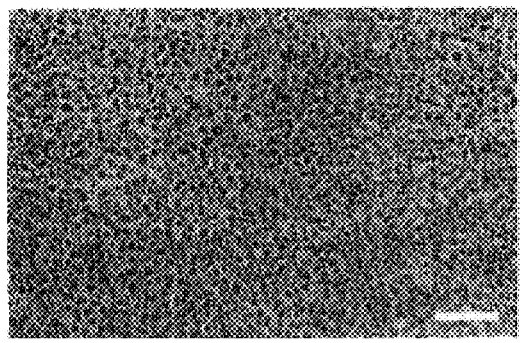
Figure 4G:
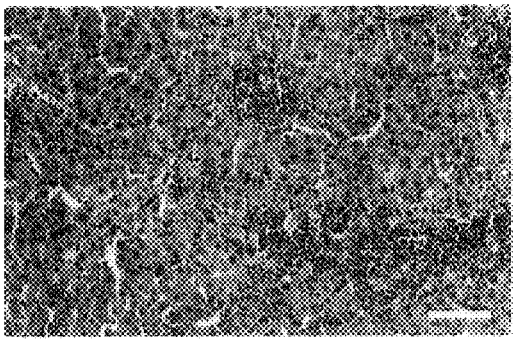

FIG. 4(A) also demonstrates that by 7 months of age the liver of transgenic animals became enlarged as compared to wild-type (~2-fold increase). In addition, the transgenic livers also developed visible white patches which were shown to be concentrations of mature eosinophils and myeloid progenitor cells in the photographs of H/E stained sections of transgenic liver in FIG. 4(D). This panel includes photographs of wild-type (+/+) liver as well as transgenic liver (NJ.1638). The hepatic tissue of the transgenic animal became infiltrated with large numbers of myeloid cells (mostly mature eosinophils) with large foci of leukocytes surrounding the hepatic blood vessels. FIG. 4(D) shows that the degree of myeloid cell infiltration was substantial. Smear preparations of the liver cell suspensions also showed the presence of erythroblasts and maturing erythrocytes, demonstrating that IL-5 stimulation of the liver elicits a wide spectrum of hematopoietic activities.

EXAMPLE VI

IL-5 Induced Changes in Bone Marrow and Extramedullary Hematopoiesis

Cell differential analyses of the two prominent hematopoietic compartments in mice, the bone marrow and spleen were performed, to investigate the in vivo role of IL-5 in eosinophilopoiesis and to assess the other possible hematological effects of IL-5 over expression. These data are collected in the Tables that are a part of FIG. 5 (see FIGS. 5(A) and (C), the data of which is duplicated in Tables 2 and 3, respectively). The data contained in these Tables includes total cell counts per femur or spleen, respectively, and "low resolution" cell differentials assessing the relative percentages of mature WBC and erythrogenic blast cells. Data were collected from both wild-type and NJ.1638 mice at 1, 4, and 10 months of age.

Total peripheral WBC counts of NJ.1638 mice grew by 40-fold over wild-type mice during the time frame examined, yet the systemic expression of IL-5 in these mice had no effect on total bone marrow cellularity (FIG. 5(A)).

Transgenic femoral cellularity remained approximately the same as age matched controls, each apparently increasing with age only as a reflection of femur size. The lack of increase in total cellularity, however, did not result from a constancy in the relative proportions of each hematopoietic cell type. Eosinophils and their committed progenitors increased from 3% of total marrow cells in wild-type mice to more that 70% of the transgenic bone marrow. These increases result at the expense of the other marrow cell-types, all of which decreased in relative proportion from their wild-type levels. The decrease in erythroblast cells was of particular physiological relevance.

FIG. 5(A) shows that transgenic femoral marrow loses 75% of its steady-state erythroblast cells which probably accounts for the lack of visible red color of the resected femurs. Since the hematocrits of transgenic animals were equal to wild-type values, the loss of red blood cell production from the marrow must be compensated for by extramedullary erythropoiesis. Although histological analyses of the liver suggested that this organ is now erythropoietic, this activity was small compared to the increased erythropoietic activity demonstrated in the spleen (FIG. 5(C)).

were approximately equal to age matched wild-type individuals and the transgenic fractions actually decreased in comparison to wild-type spleens with the age of the animals. However, if the increase in spleen cellularity was taken into account, the erythropoietic capability of the transgenic spleen increased substantially over wild-type levels. For example, at 4 months of age erythroblasts represented 17% of splenocytes in transgenic mice as compared to 20% in wild-type mice. Since the total cellularity of the 4 month old transgenic spleen is $3.11 \times 10^9$ cells, as opposed to the $1.86 \times 10^8$ cells composing the wild-type spleen, the erythropoietic capability of the transgenic spleen has increased more than 14-fold $((3.11 \times 10^9) \times 17 / (1.86 \times 10^8) \times 20)$.

The spleen cellularity data also demonstrated that unlike wild-type spleen which is composed of less than 1% eosinophils, these leukocytes become the predominant cell type of this organ as a result of IL-5 overexpression. Eosinophils represented approximately 50% of total splenocytes through the time frame examined and because by 4 months of age transgenic spleen cellularity was $>3 \times 10^9$ cells, the total number of eosinophils contained in the spleen of these animals was $>1 \times 10^9$ cells. These spleen eosinophils represented a reservoir greater than 16-fold the total number

TABLE 2

Percentage marrow cell types

| age (months) | mouse | total cells/femur (X $10^{-6}$) | erythroblast | mononuclear | eosinophil | neutrophil | Eosinophil lineage cells/femur (X $10^{-6}$) | | | |
|---|---|---|---|---|---|---|---|---|---|---|
| | | | | | | | Class I | Class II | Class III | Class IV |
| 1 | +/+ | 24.08 | 35.50 | 29.33 | 3.38 | 31.33 | 0.08 | 0.09 | 0.39 | 0.35 |
| | | $(2.90)^d$ | (17.59) | (15.37) | (1.60) | (8.81) | (0.05) | (0.04) | (0.22) | (0.23) |
| | NJ. 1638 | 17.12 | 9.17 | 8.50 | 70.50 | 11.83 | 0.20 | 0.69 | 3.50 | 7.98 |
| | | $(3.02)^6$ | (1.72) | (3.07) | (7.87) | (4.51) | (0.13) | (0.37) | (1.45) | (2.08) |
| 4 | +/+ | 32.65 | 39.66 | 25.34 | 2.75 | 31.74 | 0.12 | 0.08 | 0.34 | 0.42 |
| | | $(13.85)^3$ | (8.14) | (8.13) | (1.31) | (8.31) | (0.06) | (0.03) | (0.14) | (0.24) |
| | NJ. 1638 | 31.65 | 8.02 | 11.41 | 66.18 | 14.39 | 0.61 | 1.45 | 6.08 | 13.05 |
| | | $(3.60)^4$ | (4.99) | (4.49) | (6.59) | (5.16) | (0.09) | (0.45) | (0.73) | (2.53) |
| 10 | +/+ | 43.97 | 37.76 | 19.63 | 3.16 | 39.45 | 0.25 | 0.08 | 0.65 | 0.74 |
| | | $(6.79)^3$ | (4.77) | (2.47) | (1.74) | (8.92) | (0.18) | (0.05) | (0.43) | (0.52) |
| | NJ. 1638 | 33.23 | 6.03 | 9.33 | 71.75 | 12.89 | 0.53 | 1.05 | 5.55 | 17.30 |
| | | $(4.58)^4$ | (4.17) | (2.33) | (9.16) | (3.78) | (0.16) | (0.52) | (3.14) | (1.13) |

TABLE 3

Percentage spleen cell types

| age (months) | mouse | total cells/spleen (X $10^{-7}$) | erythroblast | mononuclear | eosinophil | neutrophil | Eosinophil lineage cells/femur (X $10^{-6}$) | | | |
|---|---|---|---|---|---|---|---|---|---|---|
| | | | | | | | Class I | Class II | Class III | Class IV |
| 1 | +/+ | 17.50 | 21.17 | 72.83 | 0.33 | 5.67 | 0.01 | <0.01 | 0.02 | 0.03 |
| | | $(3.64)^3$ | (6.81) | (8.04) | (0.29) | (1.04) | (0.01) | | (0.02) | (0.03) |
| | NJ. 1638 | 97.40 | 28.88 | 19.38 | 48.25 | 3.50 | 0.85 | 1.40 | 12.27 | 33.23 |
| | | $(7.20)^4$ | (2.14) | (2.36) | (2.75) | (1.47) | (0.46) | (0.44) | (2.71) | (5.65) |
| 4 | +/+ | 18.63 | 19.99 | 76.14 | 0.62 | 3.25 | 0.03 | 0.01 | 0.02 | 0.13 |
| | | $(4.05)^3$ | (13.99) | (15.90) | (0.80) | (2.60) | (0.03) | (0.01) | (0.02) | (0.17) |
| | NJ. 1638 | 311.40 | 16.98 | 27.38 | 51.31 | 4.26 | 2.25 | 8.56 | 56.18 | 92.69 |
| | | $(120.49)^4$ | (7.49) | | (10.78) | (4.69) | (1.29) | (5.02) | (24.17) | (28.51) |
| 10 | +/+ | 20.33 | 14.50 | 80.17 | 0.33 | 4.83 | 0.01 | <0.01 | 0.01 | 0.05 |
| | | $(2.32)^3$ | (7.37) | (8.52) | (0.29) | (1.53) | (0.01) | | (0.01) | (0.04) |
| | NJ. 1638 | 387.67 | 8.00 | 40.50 | 47.50 | 4.00 | 4.30 | 7.12 | 60.72 | 122.13 |
| | | $(118.00)^3$ | (3.46) | (7.40) | (7.50) | (3.00) | (2.78) | (4.41) | (37.50) | (46.95) |

The Tables contained in FIG. 5(C) show that the increased poietic activity was primarily a consequence of the dramatic increase in transgenic spleen cellularity. The cell differentials in the Table of FIG. 5(C) show the erythroblasts as a fraction of total spleen cells in one month old NJ.1638 mice of eosinophils in peripheral circulation (e.g., at 4 months of age: $1.5 \times 10^9$ spleen eosinophils/$(40.28 \times 10^3$ peripheral eosinophils/mm$^3$ of blood)$\times 2.2 \times 10^3$ mm$^3$ total blood volume). Although the proportions of other cell types in the transgenic spleen decreased relative to wild-type, the dramatic increase in total spleen cellularity resulted in similar increases in the total numbers of other WBC types stored in the transgenic spleen. These data probably reflect an immunological mechanism mediated by IL-5 which preformed stores of these cells (particularly eosinophils) are generated and stored in the spleen for use as needed.

Liquid murine bone marrow cultures have shown that IL-5 uniquely induces the lineage-specific production of eosinophils. In contrast, two other cytokines associated with leukocyte production (IL-3 and GM-CSF) elicit the production of eosinophils as well as several leukocyte cell types (e.g., neutrophils and macrophages) in these in vitro cultures. However, IL-5 stimulation of IL-3 (or GM-CSF) treated bone marrow cultures will transiently produce eosinophils. These data suggest that IL-5 is a critical regulator of cells already committed to the eosinophil lineage, having only minimal effects on early granulocytic progenitor cell populations.

The in vivo data presented here and in previous transgenic mouse studies show that only IL-5 overexpression exclusively produces a massive increase in the number of mature eosinophils; i.e., a specific peripheral eosinophilia. These observations indicate that the homeostatic level of eosinophils in mammals is determined by several cytokine-receptor interactions, but that the production of elevated levels of these granulocytes in the face of parasitic infestation or allergic inflammation is controlled by IL-5 stimulation of a mitotically active eosinophil committed progenitor cell type.

To determine the validity of this conclusion, "eosinophil/eosinophil-progenitor" cell differentials were performed on bone marrow and spleen cells from wild-type and NJ.1638 transgenic animals. These data are converted into the absolute cell numbers contained in the Tables of FIGS. 5(A) and (C) and are displayed in graphical form below each of these tables. Eosinophil differentiation was divided into four distinct stages termed "Class I, II, III, IV". This classification is based on nuclear morphology, Wright-Giemsa staining properties, and cytoplasmic granulation.

Class I cells ("promyelocytes") are characterized by a high nuclear to cytoplasmic ratio with spherical euchromatic nuclei. The cytoplasm of these cells have an intense basophilia and an absence of 1° (azuophilic) and 2° (specific) granules. Class I cells are mitotically active and committed to granulocytic differentiation, but not necessarily the eosinophil lineage.

Class II cells ("myelocytes") are the first cell type committed specifically to the eosinophil lineage. These cells are mitotically active, have a decreased nuclear to cytoplasmic ratio, and a nucleus undergoing morphological changes characterized by indention of the central region. The cytoplasm of these cells still retains a high degree of basophilia and contain small numbers of 1° granules.

Class III cells ("metamyelocytes") are the last mitotically active eosinophilic cell type prior to terminal differentiation. The nuclei of Class III cells are characterized by doughnut or ring shapes and the beginnings of condensation (i.e., a heterochromatic appearance). The cytoplasm of these cells is only slightly basophilic with evidence of both 1° and 2° granulation.

Class IV ("terminally differentiated eosinophils") is a quiescent cell type that initially resides in the marrow for several hours/days before exiting to the periphery. The nuclei of Class IV cells are heterochromatic and ring shaped, often twisting into "figure 8"-like structures. The cytoplasm of this cell type loses its basophilic staining properties and takes on the magenta coloration of the numerous and strongly eosin staining 2° granules. These terminally differentiated cells are the only class of cells that exit the marrow and, under homeostatic conditions, are the only eosinophil-like cell found in the periphery.

Figure 5B:
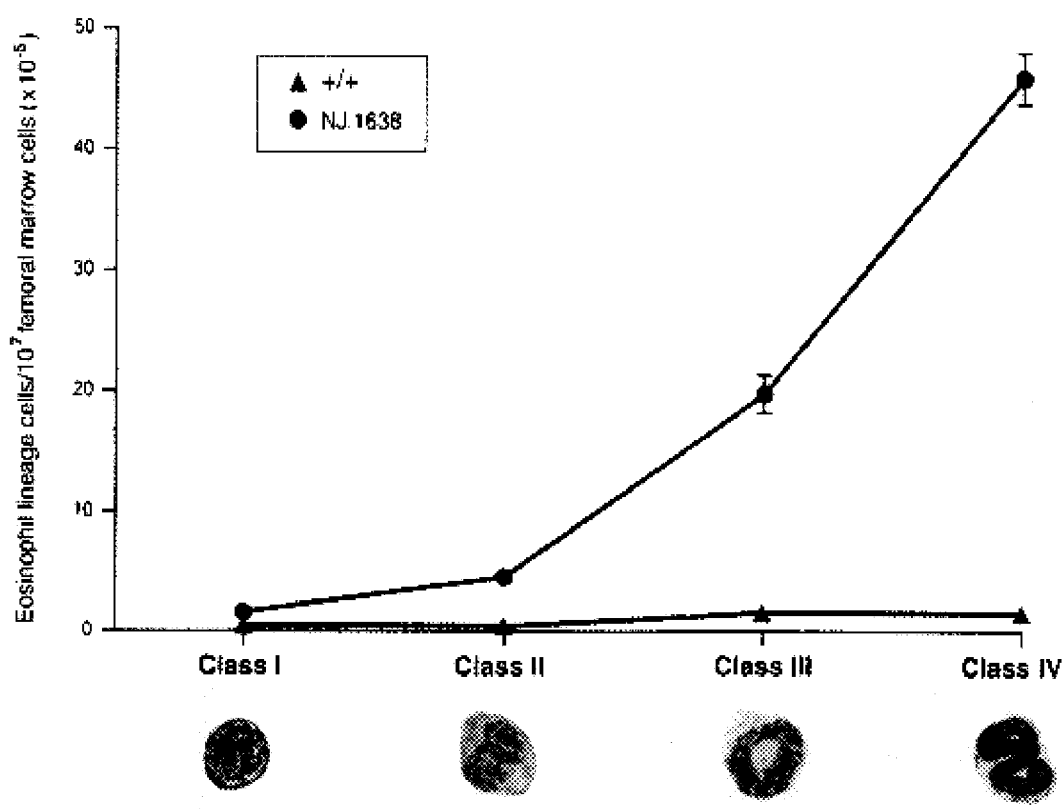
Figure 5D:
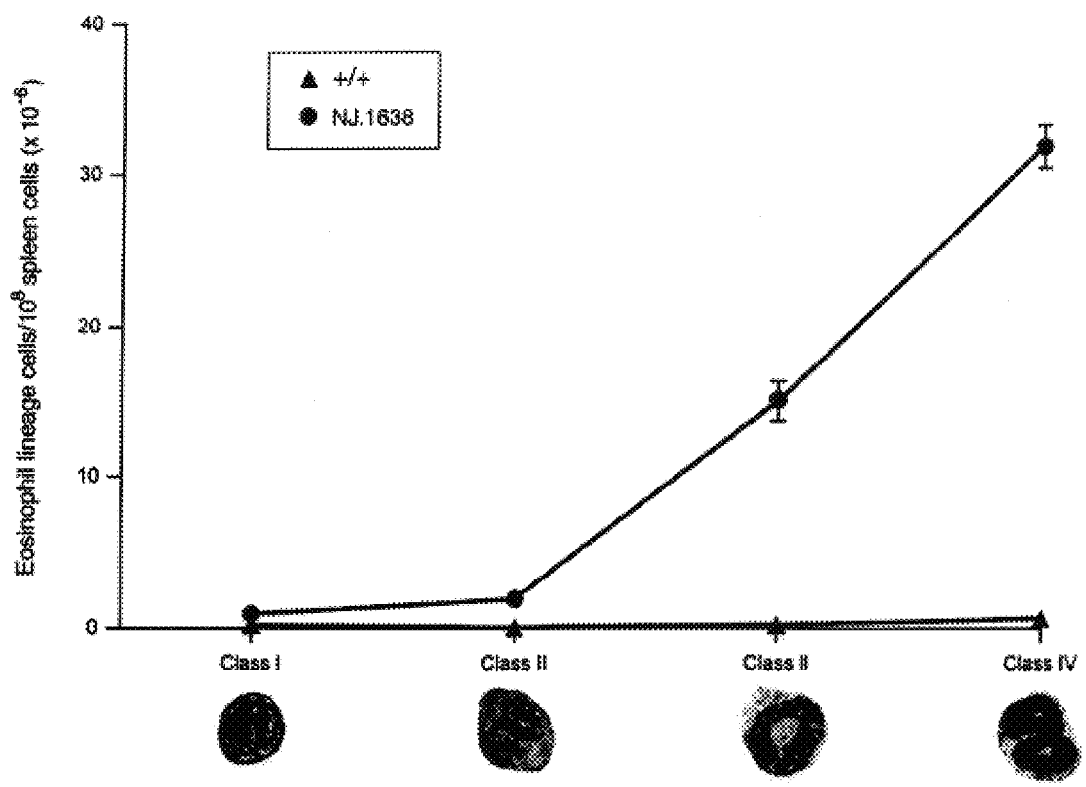

Thumb-print photographs of type examples for each eosinophilic class of cells are shown below the X-axes of the histograms in FIG. 5. The data displayed in the graphs of this Figure were an assessment of the IL-5 induced changes in the bone marrow (FIG. 5(B)) and extramedullary (FIG. 5(D)) eosinophilopoiesis. The absolute number of cells are plotted as a function of eosinophil class type. In wild-type mice, the numbers of mature eosinophils (Class IV) and progenitor cell types (Class I–III) represented a very small fraction (~3%) of total bone marrow cells and were nearly absent in the spleen (<1%). The graph of FIG. 5(B) shows that IL-5 stimulation of the bone marrow in NJ.1638 mice induced increases (compared to wild-type) in the number of cells representing each of the eosinophil lineage class types. However, the effects of IL-5 on more mature eosinophil cell types (Class III and IV) relative to the granulocytic cell type (Class I) and the earliest eosinophil lineage committed cell type (Class II) were substantial. The data show that IL-5 appeared to have specific mitogenic effects on more mature eosinophil lineage committed cells, increasing the number of cells representing Class III nearly 5-fold and Class IV >10-fold higher than Class II levels.

It is also important to note that the number of cells representing only eosinophil lineage committed Class types (II, III, IV) increased 10–30 fold relative to wild-type levels. This dramatic increase does not occur in the uncommitted granulocytic cell type, Class I. This specific stimulatory effect of IL-5 on more mature eosinophil committed cell types was also found in the extramedullary eosinophilopoiesis occurring in the spleen (FIG. 5(D)). Therefore, the original hypothesis of eosinophilopoiesis developed from liquid bone marrow cultures is essentially correct—interleukin-5 has substantive mitogenic effects only on more mature eosinophil committed cell types and is not the major regulator of the absolute numbers of early myeloid and granulocytic progenitor cell types.

EXAMPLE VII

Expression of IL-5 at High Levels Results in Eosinophilopoiesis at Extramedullary Sites The bone marrow total counts and cell differentials contained in the Table of FIG. 5(A) (duplicated in Table 2) show a large shift in hematopoietic activities toward the production of eosinophils. An examination of the total marrow cell numbers, however, demonstrated that this shift results in an eosinophilopoietic activity that was relatively minor compared to the extramedullary activity found in the spleen. For example, at 4 months of age the total number of eosinophilic progenitor cells (Class I, II, III) in the femoral marrow equals ~$1.63 \times 10^7$ cells (($0.61+1.45+6.08) \times 10^6$ cells/femur×2 femurs). In comparison, the spleen of the same animals contained greater than 40-fold more of these eosinophilic progenitor cells ($6.73 \times 10^8$ cells) suggesting that IL-5 is differentially stimulating extramedullary production of eosinophils.

The gene encoding the mouse eosinophil granule major basic protein (mMBP) is expressed in the bone marrow of wild-type mice and the prevalence of mMBP transcripts is unregulated in response to helminthic parasites. Measurable steady-state levels of mMBP mRNA were found only in tissue sites where eosinophilopoietic progenitor cell types were present; i.e., mature terminally differentiated eosinophils do not contain mRNAs coding for this 2° granule component. As a result, this assay is a sensitive method for the detection of early eosinophilic progenitor cells and thus tissue-specific eosinophilopoietic activities. The extent of these activities at different peripheral sites in wild-type and NJ.1638 mice is shown by the RNA gel blot analysis presented in FIG. 6.

Figure 6:
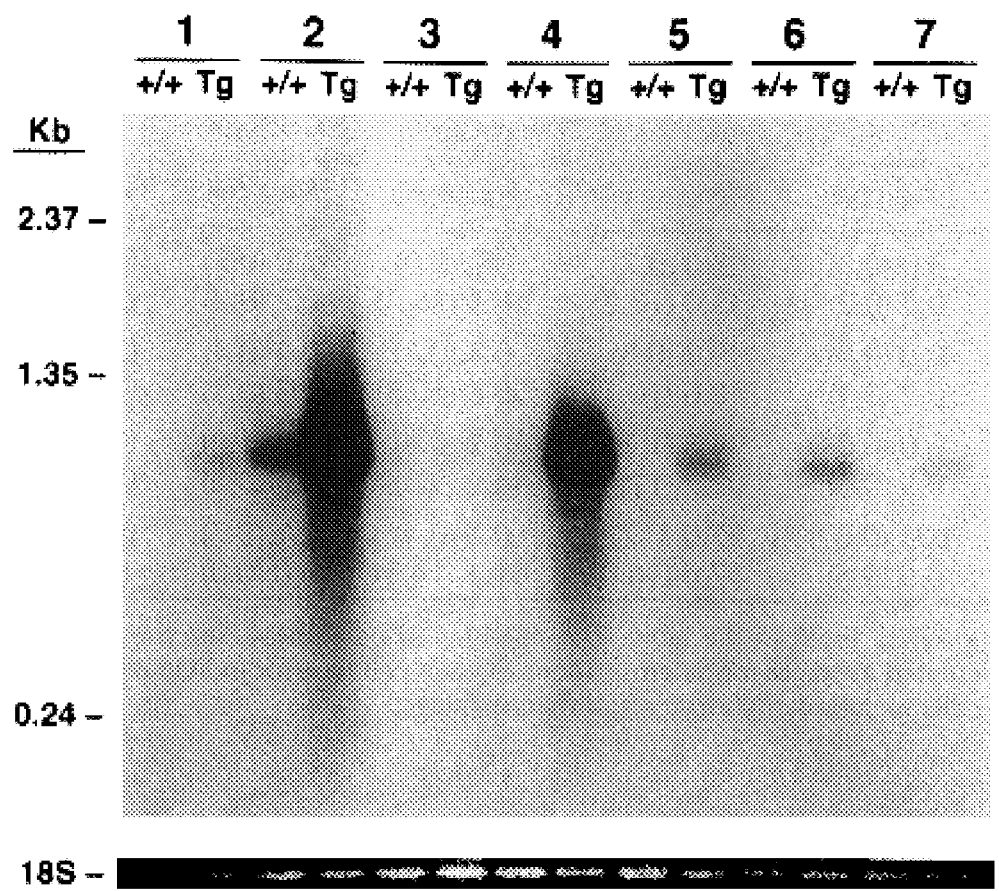
FIG. 6. Tissue-specific accumulation of eosinophil major basic protein (mMBP) gene transcripts. Northern blot of wild-type C57BL/6J (+/+) and NJ.1638 transgenic (Tg) tissue RNAs probed with a random-primed $^{32}$P-labeled mMBP genomic fragment, p9.35. Each lane contains 15 pg of total RNA. Group 1, peripheral blood; Group 2, bone marrow; Group 3, peritoneal cavity cells; Group 4, spleen; Group 5, liver; Group 6, lung; Group 7, leg muscle. A photograph of the 18S small ribosomal subunit stained with ethidium bromide is shown to verify the presence of RNA in each lane.

FIG. 6 contains a photograph of a Northern blot that includes total RNA from several tissues of 7 month old wild-type and age matched NJ.1638 mice. This blot was in agreement with histological analyses of mouse tissues which show that the only prominent location of eosinophilic progenitor cells in wild-type mice was the bone marrow. Longer exposures of this blot also showed the presence of small numbers of eosinophil progenitor cells in wild-type spleen. The lack of a hybridization signal in total RNA from transgenic peritoneal cavity cells, a compartment which lacks evidence of eosinophilic progenitors and whose cellularity is 50% mature eosinophils, demonstrated the specificity of this assay for only immature eosinophil lineage committed cells. These results confirm the bone marrow and spleen cell differential data shown in FIGS. 5(A) and (C), which showed that IL-5 stimulation causes the eosinophilic progenitor populations in each of these tissues to expand dramatically and this expansion is accurately reflected in the increase of tissue-specific MBP transcripts. The increase in spleen-derived transcripts was particularly dramatic owing to the tremendous increase in the number of eosinophil progenitor cells at this extramedullary site.

The data in FIG. 6 also demonstrated that IL-5 stimulation in vivo induces varying degrees of extramedullary eosinophilopoiesis (as judged by the presence of steady-state mMBP transcripts) in nearly all transgenic tissues examined. The overwhelming dominance of splenic extramedullary eosinophil production and the appearance of other peripheral focal clusters of eosinophilopoietic activity in NJ. 1638 mice indicated that the fundamental mechanism by which IL-5 induces a rapid, and often massive, peripheral eosinophilia is probably through the establishment/elaboration of extramedullary sites of eosinophilopoiesis.

which were eosinophils. The peritoneal cavity cellularity of NJ.1638 mice as a function of postpartum age is shown by results presented in Table 4. Surprisingly, IL-5 expression in these mice resulted in a dramatic elevation in the total cellularity of the peritoneal compartment. This observation was correct even for young mice (one month of age). As shown in Table 4, the cellularity of this cavity in one month old mice increased to a level of >40-fold above numbers found in wild-type mice ($8.36 \times 10^7$ cells versus $1.96 \times 10^6$ cells). These extremely elevated levels (i.e., $>100 \times 10^6$ cells) persist as the animals get older although the kinetics of cell accumulation are somewhat complex (i.e., variable on a mouse to mouse basis).

The increases in cellularity found in these mice were also accompanied by a shift in cell composition. Whereas wild-type peritoneal cavity cells were composed of mostly mononuclear cells (lymphocytes and macrophage/monocytes) (~98%), the cells infiltrating the peritoneal cavity of NJ.1638 mice were generally 40–60% eosinophils and 40–60% mononuclear cells with a small (<1%) influx of neutrophils and mast cells (Table 4). This observation, together with the dramatic increases in peritoneal cavity cellularity, demonstrates that the large cellular infiltrate of this compartment is not simply the result of the influx of vascular eosinophils but is also the consequence of the specific recruitment of mononuclear cell types (10-fold increase over wild-type). In summary, the observations presented in Table 4 show that the peritoneal cavity cellularities of these transgenic mice are comparable in number and composition to the induced cellularity associated with helminthic parasite (*M. corti*) infestation of the peritoneal cavity and may reflect similarities in the mechanisms which induce each phenomena.

TABLE 4

| | | cell number/peritoneal cavity (X $10^{-6}$) | | | | percentage of each cell type | | | |
|---|---|---|---|---|---|---|---|---|---|
| age (months) | mouse | total | mononuclear | eosinophil | mast cell | neutrophil | mononuclear | eosinophil | mast cell | neutrophil |
| 1 | +/+ | 1.96 | 1.92 | 0.00 | 0.04 | 0.00 | 98.00 | 0.00 | 2.00 | 0.00 |
| | | $(0.11)^3$ | (0.10) | (0.00) | (0.001) | (0.00) | (0.69) | (0.00) | (0.69) | (0.00) |
| | NJ. 1638 | 83.60 | 27.22 | 55.99 | 0.16 | 0.16 | 33.03 | 66.50 | 0.18 | 0.18 |
| | | $(23.35)^3$ | (13.65) | (22.90) | (0.15) | (0.15) | (18.22) | (18.43) | (0.16) | (0.16) |
| 4 | +/+ | 7.30 | 7.24 | 0.02 | 0.03 | 0.00 | 99.20 | 0.35 | 0.40 | 0.05 |
| | | $(3.30)^4$ | (3.28) | (0.03) | (0.04) | (0.00) | (0.49) | (0.57) | (0.40) | (0.1) |
| | NJ. 1638 | 142.00 | 72.02 | 69.07 | 0.48 | 0.16 | 48.57 | 50.77 | 0.30 | 0.10 |
| | | $(73.80)^3$ | (49.11) | (31.46) | (0.67) | (0.27) | (10.44) | (10.53) | (0.30) | (0.17) |
| 7 | +/+ | 6.43 | 6.21 | 0.02 | 0.17 | 0.00 | 96.76 | 0.23 | 2.63 | 0.10 |
| | | $(2.12)^3$ | (2.01) | (0.04) | (0.11) | (0.01) | (1.73) | (0.40) | (1.82) | (0.17) |
| | NJ. 1638 | 126.08 | 66.02 | 57.09 | 0.10 | 0.53 | 52.67 | 44.02 | 0.10 | 0.38 |
| | | $(45.36)^6$ | (23.73) | (28.58) | (0.16) | (0.54) | (11.47) | (9.30) | (0.15) | (0.33) |
| 10 | +/+ | 7.92 | 7.68 | 0.05 | 0.16 | 0.03 | 96.98 | 0.50 | 2.08 | 0.43 |
| | | $(2.21)^4$ | (2.16) | (0.05) | (0.07) | (0.02) | (0.69) | (0.44) | (0.70) | (0.34) |
| | NJ. 1638 | 89.93 | 51.57 | 37.37 | 0.00 | 0.85 | 57.57 | 41.10 | 0.00 | 1.00 |
| | | $(17.64)^3$ | (15.78) | (17.23) | (0.00) | (0.76) | (15.98) | (14.90) | (0.00) | (1.00) |

Peritoneal cavity cell counts and differentials as a function of postpartum age. Values appearing as exponents represent the number of measurements (i.e., animals) used to generate the data listed in the table. The tabular values in parentheses are the standard deviations associated with the measured numbers listed.

EXAMPLE VIII

A Massive Peritoneal Cavity Eosinophilia Accompanies CD3δ Driven IL-5 Expression Unlike wild-type mice, the peritoneal cavities of NJ.1638 mice were infiltrated by large numbers of cells, many of

EXAMPLE IX

CD3δ Driven Thymocyte/T Cell Production of IL-5 Results in a Variety of Inflammatory Histopathologies As noted above, three independent transgenic lines with the CD3δ/IL-5 construct were generated. Prior to the detailed analysis of individuals from the NJ.1638 line of mice, animals derived from all three founder mice had been observed to suffer from a series of inflammatory-like pathologies, including unexplained early death (average life expectancy of <12 months). The extreme severity of these pathologies in the founder NJ.759 and its offspring has led to the extinction of this transgenic line.

To determine the scope and details of the histopathologies that result as a consequence of IL-5 overexpression in were observed. However, in the next interval, 6–12 months of age, approximately one third of the animals examined showed evidence of hair loss and skin ulceration. In mice surviving >12 months of age, the frequency of skin pathologies increased to >75%. Once established, the number and severity of the skin lesions usually increased rapidly. These severely effected mice often became lethargic, showed signs of kyphosis, and had a high rate of mortality.

TABLE 5

| Mouse | Age (months) | Histopathology | Total no. of animals | No. of animals exhibiting pathology | Frequency of occurrence (%) |
| --- | --- | --- | --- | --- | --- |
| Normal | 0–12 | Death by 12 months of age | 131 | 0 | 0% |
| NJ.1638 | 0–12 | | 102 | 70 | 69% |
| Normal | 0–6 | Loss of hair and development of ulcerating skin lesions | 40 | 0 | 0% |
| | 6–12 | | 40 | 0 | 0% |
| | >12 | | 40 | 0 | 0% |
| NJ.1638 | 0–6 | | 38 | 0 | 0% |
| | 6–12 | | 24 | 8 | 33% |
| | >12 | | 21 | 16 | 76% |
| Normal | 0–12 | Extreme congestion and swelling of lymph nodes | 131 | 0 | 0% |
| NJ.1638 | 0–12 | | 102 | 9 | 8.8% |
| Normal | >12 | Occurrence of rectal prolapse | 40 | 0 | 0% |
| NJ.1638 | >12 | | 21 | 3 | 14% | thymocytes/T cells, hundreds of mice derived from the NJ.1638 founder were systematically examined over 24 15 months. In addition to splenomegaly and liver pathologies (see FIGS. 4(A) and (B)), these mice exhibited signs of immune-mediated inflammation at peripheral sites that have a high homeostatic resident population of eosinophils in wild-type mice. The advent of these "symptoms" appeared to be age dependent.

Figure 7A:
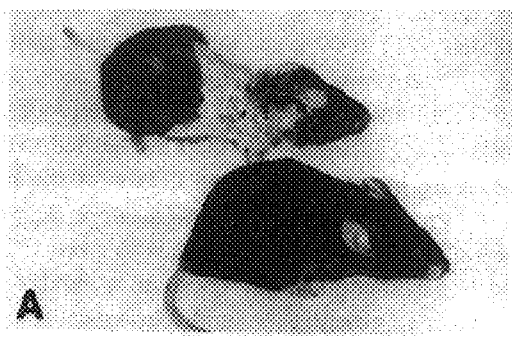
FIGS. 7A–D. Histopathologies exhibited resulting from ectopic expression of IL-5 in NJ.1638 mice. All photographs shown were taken using Kodak Ektachrome 100 daylight slide film and a Nikon F3 camera. (A) Representative photograph of two NJ. 1638 mice (14 months postpartum) exhibiting the extremes of dermal phenotypes found in these mice. (B) Higher magnification view of the mouse in panel (A) displaying hair loss and skin ulcerations. (C) Fully-body photograph of a 7 month old NJ.1638 mouse exhibiting spontaneous swelling of multiple peripheral lymph nodes. (D) Photograph of the genital-rectal areas of three NJ.1638 mice (14 months postpartum) showing either no pathology (mouse pictured on the far left) or different degrees of rectal prolapse.

Several studies of large numbers of NJ.1638 animals (and age matched controls) are collected in Table 5. One of the more difficult issues associated with maintaining NJ.1638-derived mice was the sudden unexplained deaths that occur in these mice. The data found in Table 5 show that in a population of >100 NJ.1638 mice, 69% of these animals die before 12 months of age (no deaths recorded in age matched wild-type mice). The death of many of these animals was not necessarily preceded by a deterioration of health. Postmortem examinations failed to unambiguously identify the cause of death, although in some of these mice the heart had enlarged 2–3-fold. Similar observations are seen in human HES (hypereosinophilic syndrome) patients and are consistent with other inflammatory diseases involving the expansion of eosinophil numbers. The most common of the overt histological pathologies experienced by these mice was the loss of hair and ulceration of the skin. Photographs of a mouse exhibiting typical dermatological lesions are shown in FIGS. 7(A) and (B).

Figure 7B:

The two mice in panel (A) are NJ.1638 individuals that are 14 months of age. Whereas one of these mice exhibited the hair loss and skin ulceration sometimes found in NJ.1638 mice, its age matched transgenic littermate appeared healthy and showed no sign of dermatological problems. FIG. 7(B) shows a close-up view of the effected individual. Alopecia was a common occurrence in these mice and usually preceded skin ulceration.

Figure 7C:
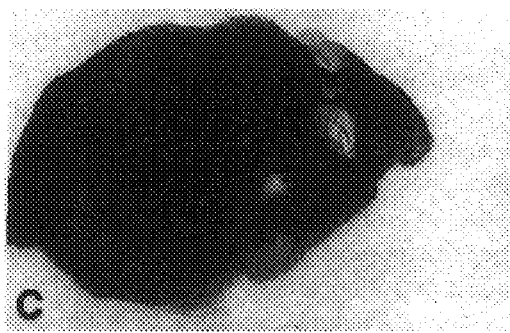

Table 5 lists the dermatological observations associated with NJ.1638 mice as a function of postpartum age. In mice 0–6 months of age no incidents of dermatological problems The spontaneous swelling of lymph nodes as the result of the accumulation of peripheral WBC was a recognizable phenotype of NJ.1638 mice. An example of this syndrome is shown in the photograph of FIG. 7(C). Several peripheral lymph nodes below the skin of the mouse in this photograph had enlarged as a result of the accumulation of cells. The lymph nodes enlarged as a solid mass characterized by the presence of several cell types. Although the identity of all of the cells composing these nodules had not been determined, many of the cells were mature eosinophils, non-eosinophil myeloid progenitor cells, and B/T lymphocytes. A quantitative assessment of the frequency with which this phenotype occurs is shown in Table 5. Enlarged lymph nodes occurred in nearly 9% of NJ.1638 mice below the age of 12 months. The frequency of occurrence did not appear to be an age dependent phenomena and spontaneously occurred with equal frequency in all age groups of mice studied. In addition, the enlargement of lymph nodes was not restricted to the periphery. Swelling and cell accumulation also occurred within the lymph nodes associated with the intestine (Peyer's patches) as well as the ventral mesenteric lymph nodes. These observations suggest that lymph nodes become congested with cells either because of IL-5 stimulated poietic activities similar to other extramedullary sites or IL-5 overexpression promotes the spontaneous occurrence (and/or enhances the survival) of leukemic/lymphomic transformations which proliferate in the nodes.

Figure 7D:

NJ.1638 mice also experienced inflammatory symptoms of the lower bowel exemplified by the occurrence of rectal prolapse. The occurrence of this pathology was strictly an age dependent phenomena and was found only in mice surviving >12 months of age. FIG. 7(D) contains a photograph of the genital-rectal area of three 14 months old NJ.1638 mice. These animals were selected because they show the spectrum of rectal pathologies that were found in these transgenic mice, including no rectal pathology (far right), minor rectal prolapse (middle), severe rectal prolapse with wet loosen stool (far left). Table 5 shows that the frequency with which rectal prolapse occurs in these older mice was 14% (rectal prolapse was not seen in any of the control animals in this study).

In general NJ.1638 mice are in poor health and have diminished reproductive capabilities relative to age and sex matched controls. These symptoms were so severe in another independently derived transgenic line (NJ.759) that it led to the extinction of this line.

This suggests that the observed pathologies occur secondarily as either a consequence of immune changes induced in the mice in an age dependent manner or occur as a result of an additional signal that elicits an uncontrolled inflammatory cascade. This additional signal may be as simple as a slight irritation and scratching. The induced physical trauma may elicit eosinophil degranulation and since the number of cells are so high, the resulting reaction quickly escalates into a severe pathology.

Figure 8:
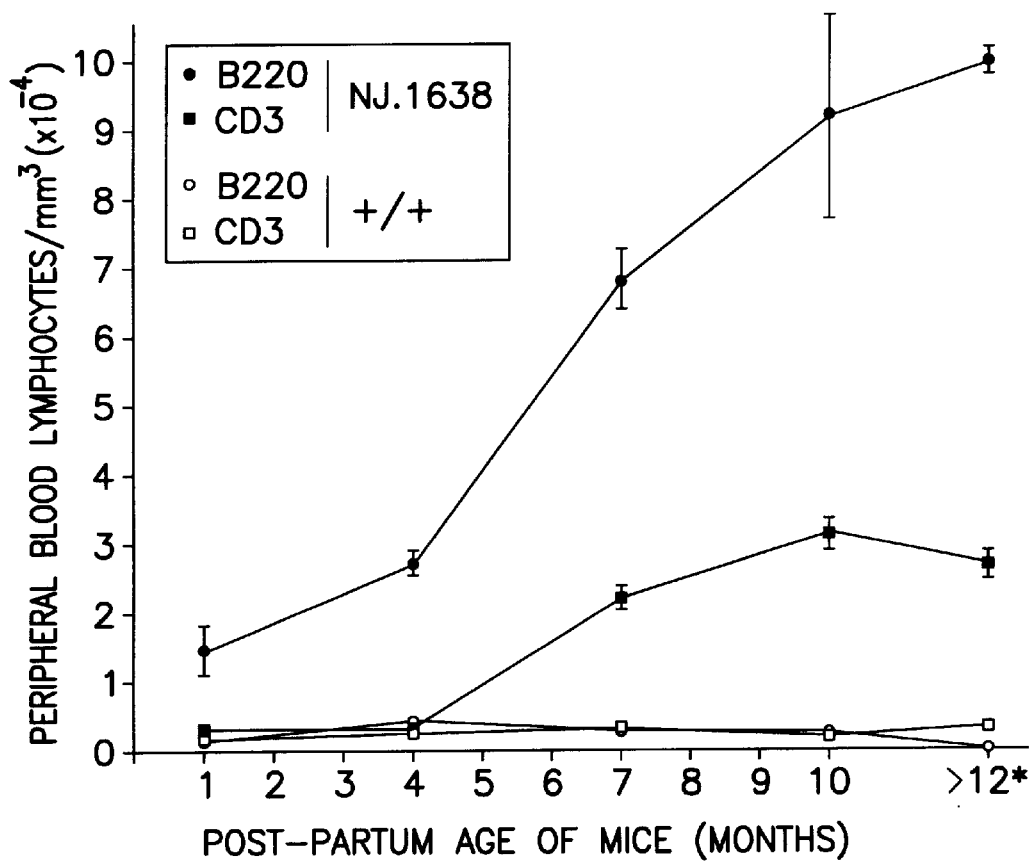
FIG. 8. IL-5 induced changes in NJ.1638 lymphocyte population kinetics as a function of postpartum age. Peripheral blood of NJ.1638 mice, and age matched wild-type controls, were analyzed by FACS using the T cell specific marker CD3 and the B cell marker B220. The data reduction was accomplished through the assessment of the fraction of cells identified by each marker relative to a lymphocyte gate established from scatter blots of total white blood cells (WBC). The data points shown were generated by multiplying the FACS-derived percentages by the absolute number of lymphocytes determined from cell differentials of peripheral blood (see Table 1). In all cases, the data points presented are the result of the analyses of multiple individuals (n 24).
Figure 9:
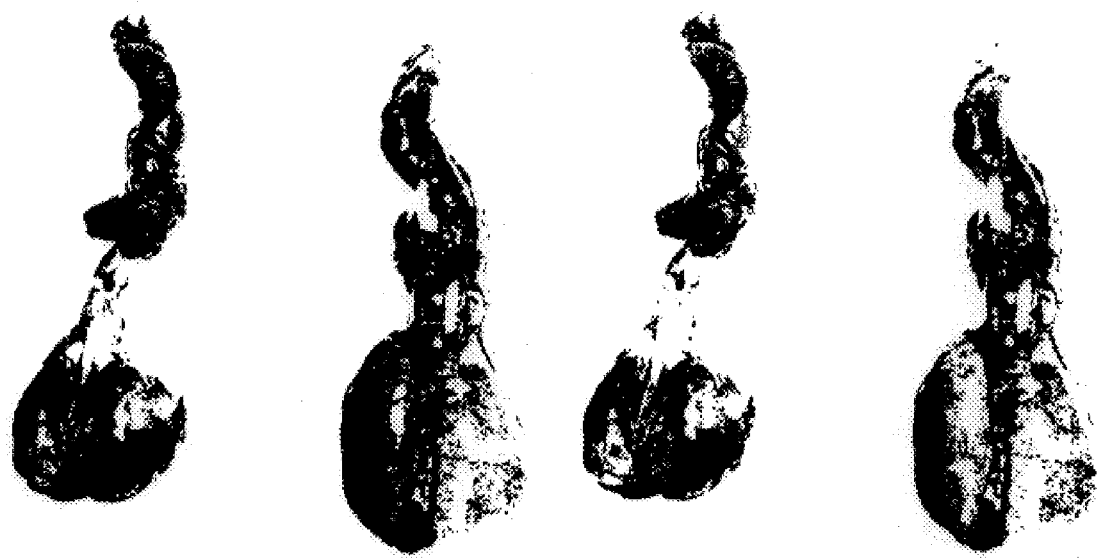
FIG. 9. Lungs dissected from wild-type (left) and CC10/IL-5 transgenic (right) mice.
Figures 10A, 10B:
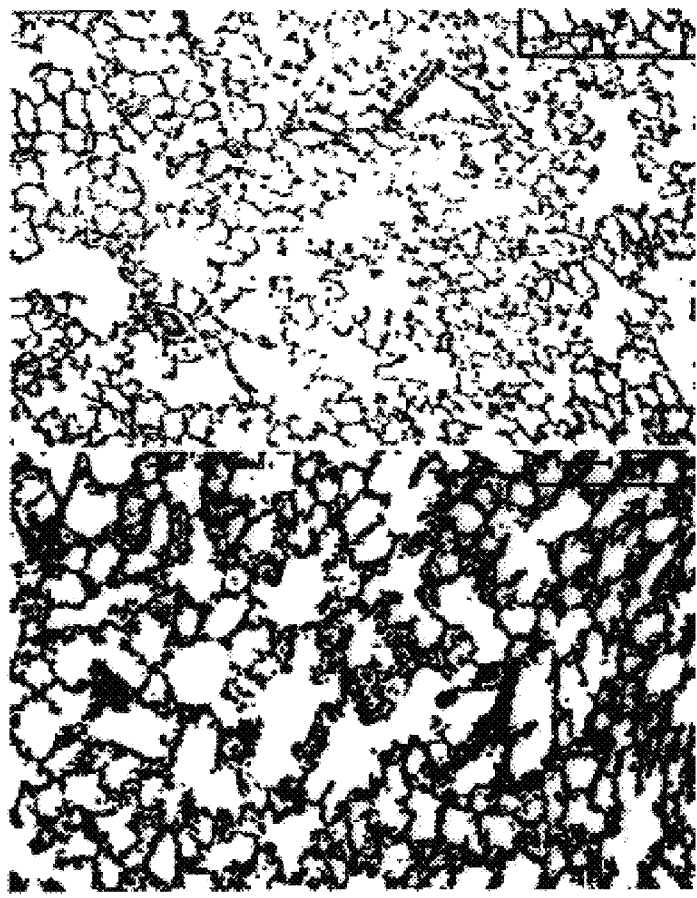
FIGS. 10A–B. Histological sections from the lungs of wild-type (A) and CC10/IL-5 transgenic (B) mice. The lungs of transgenic mice have gross distortions in the alveoli. Eosinophils are clearly present in the transgenic lungs.
Figures 11A, 11B:
FIGS. 11A and B. Histological sections from the lungs of wild-type (A) and CC10/IL-5 transgenic (B) mice. These sections show the massive increase in cellularity in the peri-bronchial lymphoid tissues of the lung of transgenic mice.
Figures 12A, 12B, 12C:
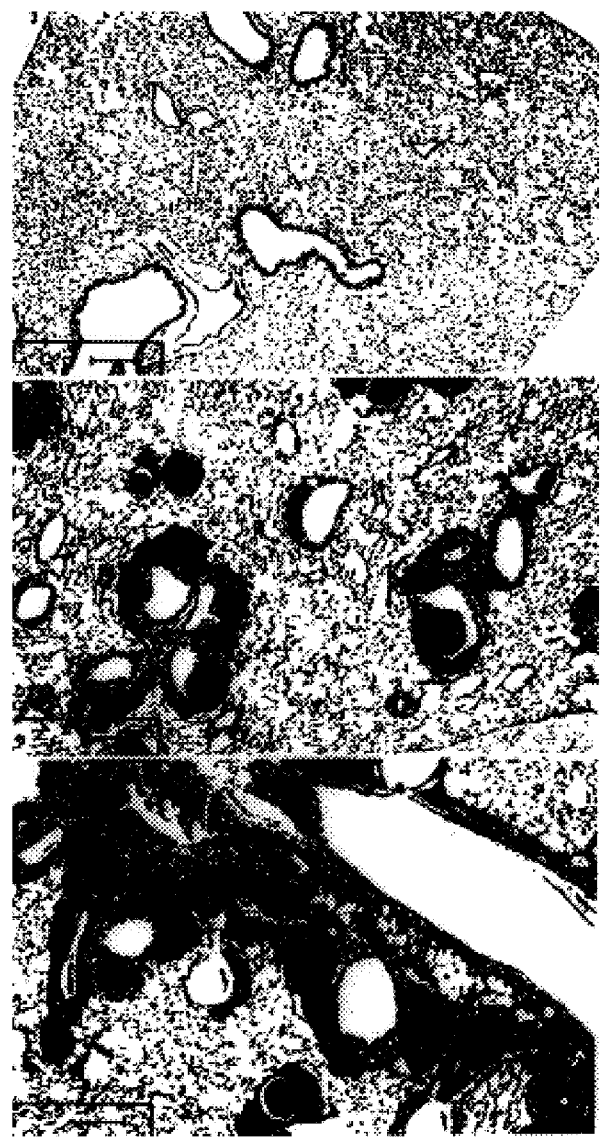
FIGS. 12A–C. Histological sections from the lungs of wild-type (A) and CC10/IL-5 transgenic (B and C) mice. These sections show the massive increase in cellularity in the peri-bronchial lymphoid tissues of the lung of transgenic mice.
Figure 13A:
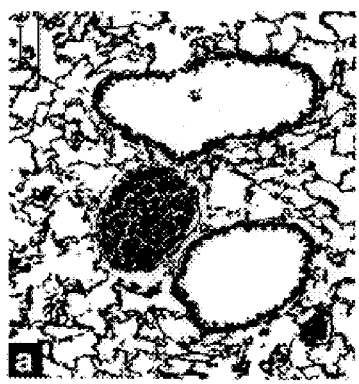
FIGS. 13A–F. Immunofluorescence of the lung sections from a CD3δ.IL-5 (line 1638) transgenic mouse. These sections were stained with an eosinophil-specific antibody to the major basic protein (MBP) of the eosinophil granule. a) lung stained with H&E; b) lung stained with anti-MBP; c) negative control for background fluorescence; d) an enlarged lymph node from the intestine stained with H&E; e) an enlarged lymph node from the intestine stained with anti-MBP; f) negative control for background fluorescence.
Figure 13B:
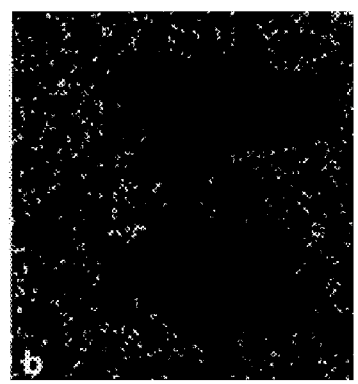
Figure 13C:
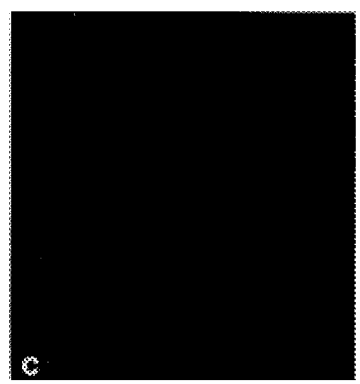
Figure 13D:
Figure 13E:
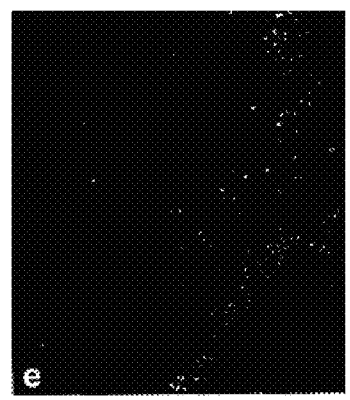
Figure 13F:
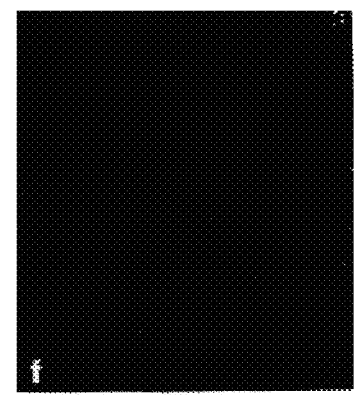
Figures 14A, 14B:
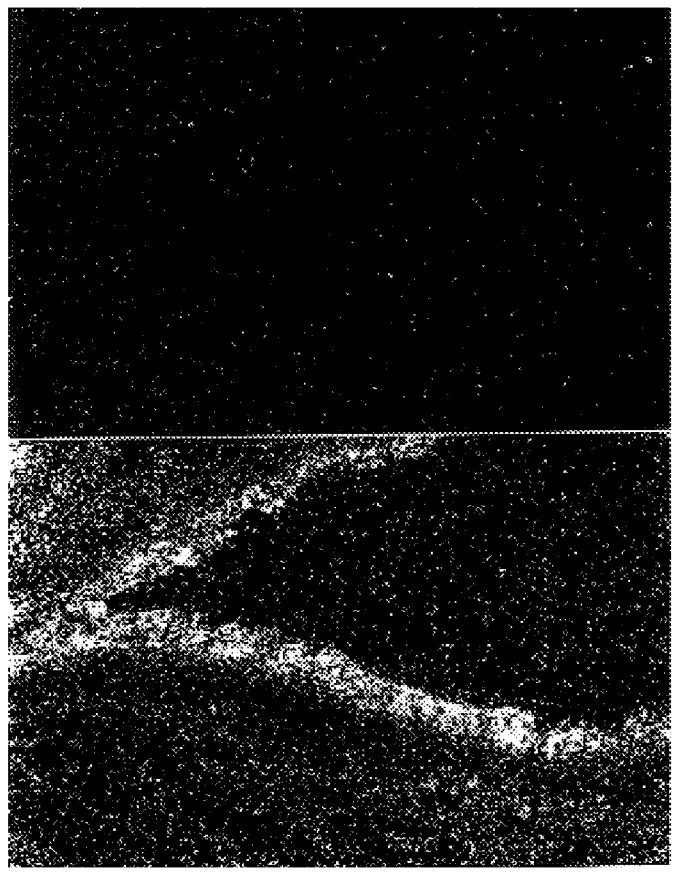
FIGS. 14A–B. In situ hybridizations to lung sections from CC10/IL-5 transgenic mice. An RNA probe specific for IL-5 was hybridized to a transgenic lung section (A). The negative control is shown in the bottom panel (B).
Figures 15A, 15B:
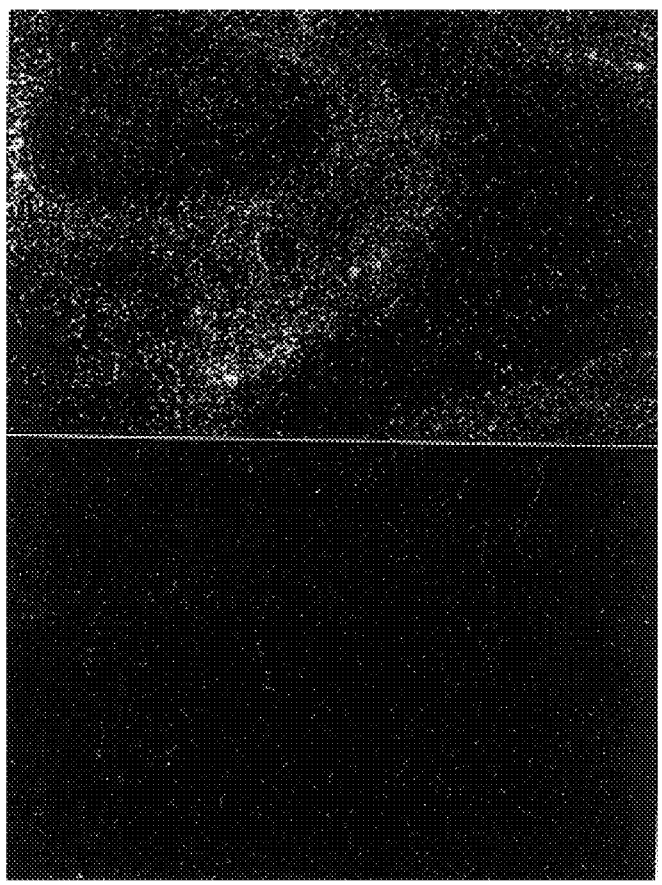
FIGS. 15A–B. In situ hybridizations to lung sections of a large airway from CC10/IL-5 transgenic mice. An RNA probe specific for IL-5 was hybridized to a transgenic lung section (A). This section shows the intense staining of the lung bronchial airway epithelium. The negative control is shown in the bottom panel (B).
Figures 16A, 16B:
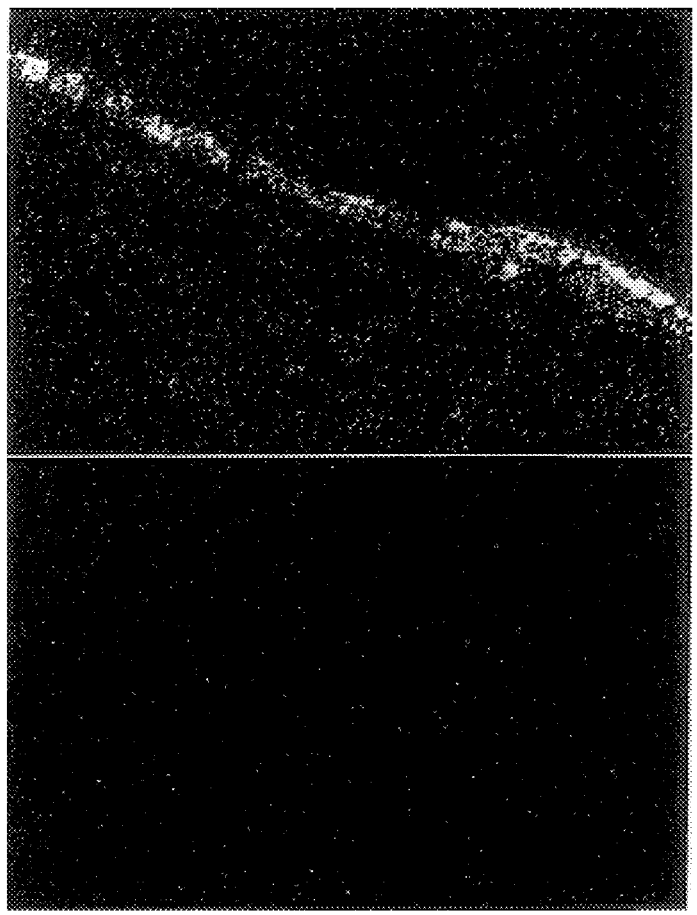
FIGS. 16A–B. In situ hybridizations to lung sections from CC10/IL-5 transgenic mice. An RNA probe specific for IL-5 was hybridized to a transgenic lung section (A). This section shows the intense staining of the lung bronchial airway epithelium. The negative control is shown in the bottom panel (B).

The suggestion that the histopathologies result from age dependent immune changes is supported by the data of FIG. 8 showing changes in circulating lymphocyte numbers. These data showed that CD3δdriven IL-5 expression resulted in no changes in peripheral T cell number early in life (0–4 months) and only a 3–5 fold increase in B cell numbers. However, as the mice get older (6–12 months) lymphocyte numbers suddenly increased so that by 12 months of age T cell levels had expanded 3–5 fold above wild-type levels and B cell populations had increased >30-fold. These changes correlate well with the onset of histopathologies.

Regardless of the mechanism(s) inducing the observed pathologies, the data presented here demonstrate that the constitutive expression of IL-5 in a cell type and peripheral location that are endogenous sites of expression in disease states replicates many of the observed hematopoietic and pathologic changes associated with an eosinophil-mediated TH2 type inflammatory reaction.

EXAMPLE X

IL-5 Induced Changes in Lymphocyte Cell Numbers

Previous studies of IL-5 effector functions in the mouse have suggested that this cytokine also induced changes in B cell activity. In addition, other studies have shown that aberrant expression of another TH2 associated cytokine, IL-4, results in significant changes in T cell activity. In an attempt to correlate induced changes in lymphocyte cell numbers with the onset and progression of the observed histopathologies, specific changes in peripheral lymphocyte populations were assessed by FACS analysis on venal blood. These experiments were designed to assess the absolute changes in peripheral blood B and T lymphocytes. Peripheral T cells were identified by the presence of the cell surface protein CD3 and mature B cells were identified by the presence of the marker B220. The observed absolute changes in cell number of each lymphocyte population as a function of postpartum age is graphically displayed in FIG. 4.

In wild-type mice, circulating CD3 positive (T cells) and B220 positive (B cells) lymphocyte numbers were approximately the same and changed only nominally with the age of the mice. In general, the basal level of each lymphocyte type ranged from 3–5×$10^3$ cells/mm$^3$ of blood. In NJ.1638 mice the data found in FIG. 4 showed that constitutive systemic expression of IL-5 induced age dependent changes in the numbers of each lymphocyte population. T cell numbers, for example, appeared to be initially (0–4 months of age) unaffected (relative to wild-type) by elevated levels of IL-5. The absolute number of T cells, however, increased after 4 months of age in NJ.1638 animals such that by 7 months of age these animals had T cell numbers equal to 22,000 cells/mm$^3$ of blood, a 6-fold increase from pre-4 month (and wild-type) levels. The number of T cells further increased only slightly in older mice, reaching an upper limit of 28,000 T cells/mm$^3$ of blood.

The effects of thymocyte/peripheral T cell specific IL-5 expression on B lymphocyte populations in these mice was dramatic in magnitude, affecting even very young animals. By one month of age, B cell numbers had increased to 16,000 cells/mm$^3$ of blood (i.e., 4.5-fold increase as compared to wild-type). This elevation in B cell numbers continued throughout the life of the animals increasing to more than 100,000 B cells/mm$^3$ of blood in animals >12 months of age (i.e., a >30-fold increase over wild-type animals).

These data show that the early increases in circulating lymphocyte numbers of NJ.1638 mice (0–4 months of age) were almost exclusively due to increases in the B cell compartment. In addition, during the age period when both T and B cell numbers are rapidly increasing (6–12 months) the rate of B cell increase far exceeds the rate of T cell accumulation. As a result, instead of contributing equal numbers of cells to the lymphocyte population, older transgenic mice accumulated 4-fold higher numbers of B cells relative to the corresponding T cell pool. These data provide a suggestive correlative relationship between changes in lymphocyte populations and the age dependent development of histopathologies in NJ. 1638 mice.

Discussion

While all of the available transgenic studies of ectopic IL-5 expression suggest that this cytokine predominantly effects steady-state levels of peripheral eosinophils, the data presented herein also suggest that IL-5 has additional regulatory effects on eosinophils and other cell populations if constitutively expressed in a spatial, temporal, and cell-type specific manner closely analogous to endogenous IL-5 expression.

Moreover, the data suggests that this cytokine is a key component of possible immune-mediated inflammatory pathways leading to the development of destructive physiological changes. The expression of IL-5 in thymocytes and peripheral T cell populations resulted in dramatic changes in peripheral WBC numbers with particular effects on circulating eosinophils. The effects of constitutive IL-5 expression, however, were not limited to eosinophil populations. Substantive increases were demonstrated in all WBC populations, including a >30-fold augmentation of B220+ B-lymphocyte populations. Deregulated peripheral expression of IL-5 also induced several physiological changes in these mice characterized by the infiltration and/or expansion of eosinophil populations at several extramedullary sites. The effects on extramedullary eosinophilopoiesis were particularly striking and were responsible for most of the increases found in mature eosinophil numbers. The consequences of these IL-5 mediated changes resulted in the development of several unique histopathologies leading to severe pathophysiologic changes and premature death.

The effects on circulating eosinophil numbers shown in NJ.1638 mice greatly exceeded the observed effects found in other transgenic mice expressing this cytokine at similar or even higher IL-5 serum levels. Data were presented which show that this enormous and somewhat specific increase in eosinophil numbers is most likely the result of at least two regulatory effects that can be associated with IL-5 and its expression from a peripheral lymphocyte population.

Data presented in FIG. 6 are an in vivo demonstration of the kinetic effects of IL-5 on progenitor cell populations and lineage committed cell types. These data confirm several of the conclusions derived from in vitro hematopoietic assays and definitively show that IL-5 has little to no effect on uncommitted granulocytic progenitor cell populations (Class I cells using the nomenclature presented here).

IL-5 was also shown to have only nominal effects in the numbers of very early eosinophil-committed progenitor cell types (Class II cells). The data presented hereinabove clearly demonstrate that only more mature eosinophil-committed cell types (Class III and Class IV cells) respond mitogenically to IL-5 stimulation. These observations provide in part the mechanism for the eosinophil-specific effects of IL-5 expression: other cell types may respond (directly or indirectly) to IL-5, however, those effects are small compared to the mitogenic effects this cytokine has on eosinophil-committed progenitor cells.

The extent of extramedullary eosinophilopoiesis found in NJ.1638 mice was shown to be extensive and primarily responsible for the extreme elevations of total cell number. In addition, using the appearance of steady-state mRNA for eosinophil granule protein genes as a measure for eosinophil-committed poetic activity (FIG. 7), it was shown that extramedullary eosinophilopoiesis was not restricted to the spleen but also occurred in nearly all organ systems and tissue types. These data may reflect a critical function of IL-5 as a mediator of eosinophil numbers through the expansion of extramedullary sites of poises.

An extension of this hypothesis also may explain the unique expansion of WBC numbers in compartments such as the peritoneal cavity that occur in NJ.1638 mice. If lymphocytes provide the key inflammatory signals to indicate a parasitic infestation of this compartment, then stimulation of this pathway would lead to the recruitment of WBC and the differential expansion of eosinophil numbers. Data presented in FIG. 2 showed that CD3δ-driven IL-5 expression induces the expansion of WBC numbers to levels associated with an active *M. corti* helminthic infestation of this compartment; this expansion also included the differential recruitment of eosinophils. This observation is unique to the IL-5 transgenic mice described here and is probably a consequence of IL-5 expression from a cell type and location that is consistent with endogenous expression of this signal during an immune response.

The proliferation of WBC, the expansion of eosinophil numbers and recruitment of additional sites of extramedullary eosinophilopoiesis lead to a series of debilitating histopathological changes that ultimately compromise the health and life of these animals. These changes include the uncontrolled growth of the spleen as a function of age and the extensive infiltration of the liver by WBC (especially eosinophils) in transgenic animals of all age groups. Some of the physiological changes are dramatic but produce no observed phenotype. For example, IL-5 expression substantially curtails marrow derived erythropoiesis and shifts this process to an extramedullary site (spleen). As a result, despite this potentially pathophysiologic change, red blood cell counts in transgenic animals showed little change from wild-type mice.

In summary, transgenic mice expressing IL-5 under the control of cell-type specific promoters developed unique pathophysiological changes and histopathologies specific to the site of IL-5 expression. In each case, the effects were accompanied by an expansion of peripheral blood eosinophil numbers, the establishment of extramedullary eosinophilopocisis, and tissue-specific infiltration. The site of IL-5 expression is believed to be an important determinant of tissue-specific eosinophil infiltration and the establishment of inflammatory responses involving eosinophils.

EXAMPLE XI

Generation and Characterization of Transgenic Mice Expressing IL-5 in Lung Tissue Because elevated levels of IL-5 have been correlated with allergic reactions, transgenic mice expressing IL-5 from a lung-specific promoter were prepared (Example I). Three independent lines (NJ.1659, NJ.1723, NJ.1726) were initially characterized with respect to transgene copy number, peripheral blood cellularity, and lung histology. All three lines of mice had elevated white blood cell counts, including a peripheral eosinophilia, and increases in the peribronchial cellularity of the lung. Transgene copy number varied in each line (NJ.1659 (1), NJ.1723 (10), NJ.1726 (15)) and generally correlated with the extent of the observed pathologies. On this basis, the NJ.1726 transgenic line of mice was chosen for further study of the pathophysiologic effects of expressing IL-5 in the lung epithelium.

NJ.1726 mice were back crossed to C57BL/6J (+/+) for a minimum of four generations. All data reported were derived from mice 3–8 months of age. The transgenic animals had live births and numbers of weaned offspring comparable to wild-type (+/+) mice. In addition, the transgene was inherited equally among male and female pups, indicating an autosomal insertion. The apparent morbidity and life expectancy of NJ.1726 mice were unchanged relative to transgene-negative littermates.

Figure 17:
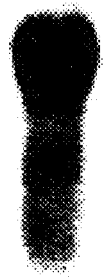
FIG. 17. Northern blot of wild-type (+/+) and NJ.1726 (Tg) tissue RNA probed with a random-primed $^{32}$P-labeled IL-5 cDNA. Each lane contains 15 $\mu$g of total RNA. Lane 1, bone marrow; lane 2, liver; lane 3, lung; lane 4, spleen. A photograph of the 18S small ribosomal subunit stained with ethidium bromide is shown to confirm the presence of RNA in each lane.
Figure 17:

Total RNA was isolated from lung tissue and formaldehyde-agarose Northern blots were prepared as described previously (Horton et al., *J. Leukoc. Biol.,* 60, 285 (1996)). Northern blot analysis showed that expression of IL-5 in transgenic animals was limited to the lung and was not detectable in any of the wild-type tissues (FIG. 17).

Figure 18:
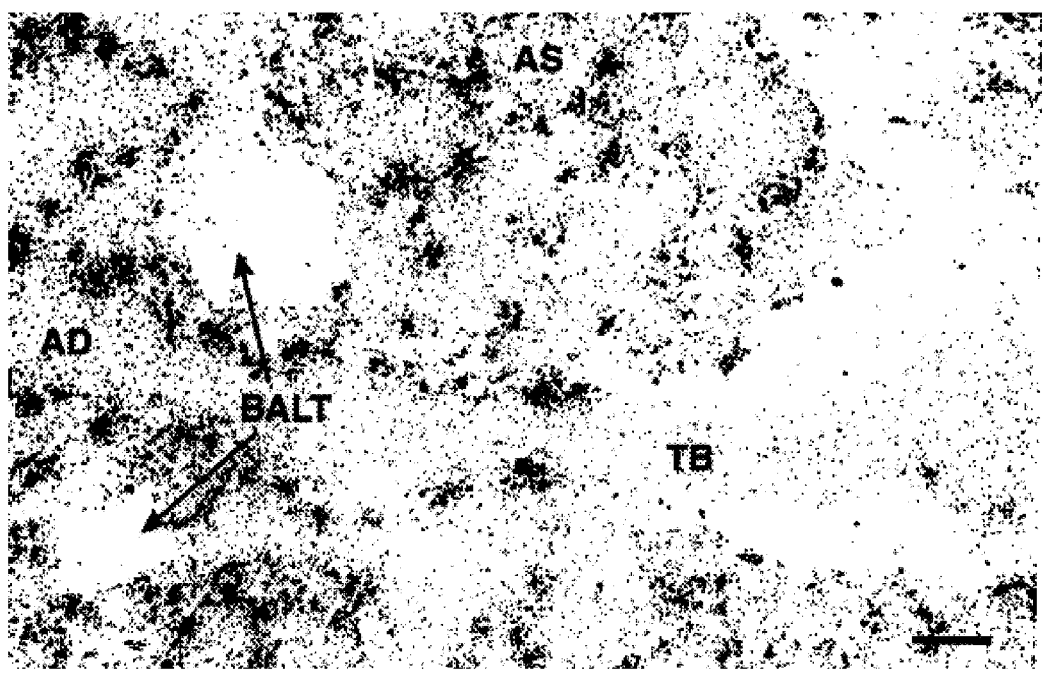
FIG. 18. In situ hybridizations showing the localization of IL-5 transcripts to the lung epithelium of NJ.1726 mice. An IL-5 antisense RNA probe was synthesized from an IL-5 cDNA cloned into the plasmid vector pBluescript KS(+). No signal was detected when a sense probe was hybridized to adjacent sections. TB, terminal bronchiole; AD, alveolar duct; AS, alveolar space; BALT, bronchus-associated lymphoid tissue. Scale bar=25 Em.
Figures 19A, 19B:
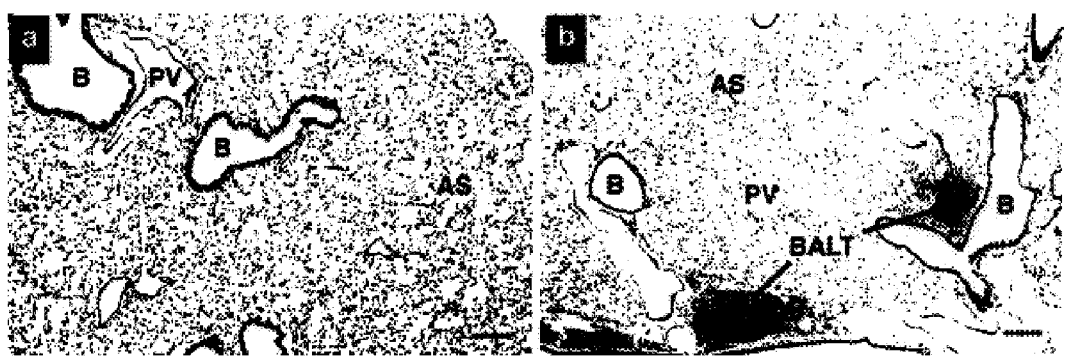
FIGS. 19A–E. Histological sections from the lungs of wild-type and transgenic mice. Panel (a) is a lung section from a wild-type (+/+) mouse. Panels (b–d) are lung sections from NJ.1726 mice. Panel (e) is a section from a NJ.1638 mouse. Sections were stained with hematoxylin/eosin prior to bright-field photomicroscopy. Panels (b) and (c) are representative photographs of the variation in phenotype found in NJ.1726 mice. The arrows in panel (c) indicate airways in an NJ.1726 mouse nearly occluded by the expansion of peribronchial lymphoid tissue. The high magnification view of a BALT aggregate (panel (d)) shows in greater detail the additional histopathologies associated with these expanded regions. Panel (e) demonstrates that although T cell-specific expression of IL-5 elevates serum levels to 400–800 pg/ml, no pulmonary changes occurred and thus the pathologies occurring in NJ.1726 mice are the result of lung-specific IL-5 expression. B, bronchiole; PV, pulmonary blood vessel, AS, alveolar space; BALT, bronchus-associated lymphoid tissue. The scale bar of panels (a), (b), (c), and (e) are 200 $\mu$m. The scale bar of the high magnification view in panel (d) is 50 Am.
Figure 19C:
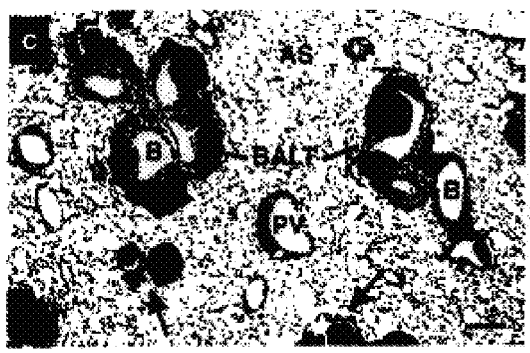
Figure 19D:
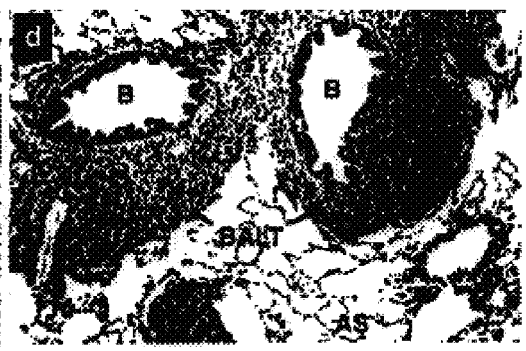
Figure 19E:
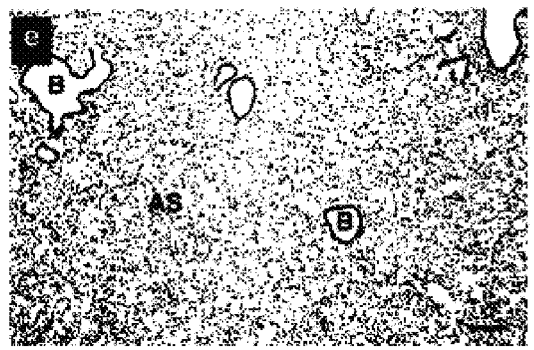

Furthermore, paraffin sections of paraformaldehyde fixed lungs that were subjected to in situ hybridization reactions using $^{35}$S-labeled IL-5 antisense RNA probes (Lee et al., *Develop.,* 115, 277 (1997)) showed that principal locations of IL-5 expression in adult NJ.1726 lungs included Clara cells of the larger airways and the proximal portion of the pulmonary acinus (i.e., the transitional zone between the conducting airways and the gas exchange areas), as well as cells whose histological characteristics, number, and location suggested that they are alveolar epithelial type II cells (FIG. 18). This expression was found throughout the lung and is consistent with the expression pattern of the rat CC10 gene in adult rat lungs (Strum et al., *Tissue & Cell* 24, 461 (1992)).

To determine IL-5 levels in bronchial alveolar lavage (BAL) fluid and blood serum in transgenic and control animals, animals were sacrificed by injection (i.p.) with a lethal dose of ketamine (600 mg/kg of body weight) and xylazine (30 mg/kg of body weight). The animals were placed under a stereodissecting microscope, the trachea was exposed and a cannula was inserted and secured by sutures. The lungs were lavaged 4 times with 1 ml aliquots of ice-cold phosphate-buffered saline (PBS) with 0.2% fetal calf serum. Approximately 3.6–3.8 ml of the instilled lavage fluid was recovered (no difference in recovery was noted between transgenic and wild-type animals). The recovered BAL fluid was centrifuged (1000 rpm for 10 minutes at 4° C.) to remove cells, and aliquots of the supernatant were frozen on dry ice and stored at −80° C. until use. Peripheral blood (300–500 mm$^3$) was recovered by nicking the tail. Blood was allowed to clot at room temperature for 30 minutes and serum was recovered by centrifugation (1000 rpm for 10 minutes at 4° C.), frozen on dry ice, and stored at −80° C. until use. IL-5 and IL-4 levels were measured using murine cytokine ELISA kits as described by the manufacturer (Endogen, Inc., Boston, Mass.).

IL-5 levels in the BAL fluid and serum were assessed by ELISA (Table 6). The (+/+) level of IL-5 in both compartments was at or below the level of detection (<5 pg/ml). In contrast, IL-5 levels in BAL fluid of NJ.1726 mice were dramatically elevated (269 ng/total lavage). An apparent consequence of airway expression at these high levels was displacement of IL-5 into the vasculature such that serum IL-5 was nearly 1700 pg/ml. IL-4 was not detectable (i.e., ≦5 pg/ml) in the BAL fluid of NJ.1726 mice. Moreover, Northern blot comparisons of endogenous pulmonary cytokine/chemokine gene activity in (+/+) and transgenic animals showed that IL-4, RANTES, MCP-3, and eotaxin remained at low and/or nearly undetectable levels in the lungs of NJ.1726 mice.

The hematopoietic consequences of IL-5 overexpression in the lung and augmentation of blood serum levels are also shown in Table 6. Microhematocrits were performed from tail-derived blood. Blood films and marrow brush smears were prepared as described by Lee et al., *J. Immunol.*, supra. Cytospins of cells isolated from collagenase-treated lungs or recovered BAL fluid were prepared using a Shandon Cytospin 3 (Shandon Scientific LTD. Cheshire, England). Cell differentials were performed from slides stained with Leukostat (Fisher Diagnostics, Fisher Scientific, Pittsburgh, Pa.) or Wright's stain. Total cell counts were quantified by hemocytometer and, together with the percent cell type by differential, were used to calculate specific cell number.

segregating them from the airway lumen. All NJ.1726 animals examined exhibited these pulmonary changes (n=11). The majority (54%) showed increases in BALT within the range presented FIGS. 19(*b, c*)).

For reasons that remain unclear, approximately 27% of 3–8 month old animals displayed the extreme form of this pathology (FIG. 19(*c*)). The accumulation of leukocytes was associated with the expansion of the lymphoid tissue around nearly all the larger airways. This expansion was often so great that it resulted in the apparent closure or near occlusion of affected airways (arrows in FIG. 19(*c*)). The appearance of this extreme phenotype was random and did not segregate to specific cages of mice or locations within the mouse colony, nor did it shorten the life span of transgenic animals. FIG. 19(*d*) shows bronchioles and the surrounding leukocytes at higher magnification. In addition to epithelial hypertrophy, the lymphocytic infiltration was associated with perturbations of the bronchial epithelium and thickening of the epithelial submucosal region of some bronchioles.

TABLE 6

| Mouse* | Hematocrit | IL-5 Present in the BAL (ng.total lavage) | Serum IL-5 (pg/ml) | Cell number/mm$^3$ of blood (X $10^{-3}$) | | | | | Cell number/femur (X $10^{-6}$) | | | | |
|---|---|---|---|---|---|---|---|---|---|---|---|---|---|
| | | | | Total | lymphocyte | monocyte | eosinophil | neutrophil | Total | erythroblasts | lymphocyte | eosinophil | neutrophil |
| +/+ | 55.3 (4.6)$^4$ | N.D. | N.D. | 9.9 (3.0)$^4$ | 6.1 (3.9) | 1.2 (0.5) | 0.2 (0.1) | 2.5 (1.0) | 27.8 (4.9)$^4$ | 11.0 (2.4) | 5.9 (0.9) | 0.7 (0.8) | 10.1 (5.1) |
| NJ. 1726 | 54.3 (4.3)$^4$ | 269 (37)$^4$ | 1696 | 41.4 (449)$^4$ | 18.8 (16.3)$^4$ | 2.6 (10.6) | 17.3 (8.7) (1.0) | 2.7 (1.5) | 30.3 | 4.1 (1.6) (3.8)$^4$ | 3.8 | 15.2 (0.6) | 7.3 (3.9) (1.8) |

Values appearing as exponents represent the number of animals used to generate the data listed in the Table. The numbers in parentheses are the standard deviations associated with the values listed. Differential cell numbers are the calculated averages derived from percent determinations of each cell type for individual animals. All differential percentages were based on ≥ 200 cells. N.D., not detected. *, listed data are derived from mice 7 months of age. +/+, C57BL/6J mice.

NJ.1726 mice have white blood cell (WBC) counts that were moderately elevated relative to (+/+) (~4-fold), exceeding 41,000 cells/mm This increase resulted primarily from an expansion of peripheral eosinophils (2% vs. 42%) although all other WBC types examined increased in absolute number. NJ.1726 femoral marrow cellularity, however, remained unchanged relative to (+/+) mice. The lack of change associated with the total marrow cell count masks a fundamental shift in cell composition. Eosoinophils increased by >20-fold relative to wild-type (+/+) mice and accounted for 50% of the transgenic marrow cells. In contrast, there was a substantive decrease in erythroblasts (60% loss). This decrease, however, did not affect peripheral red blood cell counts as assayed by hematocrit (55.3 vs. 54.3), most likely reflecting a shift in erythropoiesis from the marrow to an extramedullary site (e.g., spleen).

A systemic gross and microscopic survey of adult tissues revealed that, except for mild splenomegaly, the only pathologic manifestations of pulmonary IL-5 overexpression were found in the lungs. Prior to resection, lungs were inflated with 0.5 ml of 10% phosphate-buffered formalin and fixed overnight at room temperature. The fixed tissue samples were embedded into paraffin and sections (4–6 $\mu$M) were prepared on TESPA-treated slides for immunofluorescence or acid-washed slides for histochemical staining. The most prominent abnormalities included expansion of bronchus-associated lymphoid tissue (BALT) and the infiltration of peribronchial spaces by leukocytes. The severity of these changes varied among animals and is shown in comparison to wild-type animals (+/+) in the hematoxylin/eosin (H/E) sections of FIGS. 19(*a–c*). BALT aggregates (dominated by mononuclear cells) were surrounded by a lymphoepithelium The leukocyte infiltration associated with NJ.1726 lungs resulted directly from the specific expression of IL-5 in the lung epithelium. FIG. 19(*e*) is a representative H/E section of lung from an age-matched transgenic animal constitutively expressing IL-5 from a T-cell specific promoter (transgenic line NJ.1638). Serum IL-5 in these mice reaches as high as 800 pg/ml; yet, as shown here, the animals did not exhibit any significant lung pathology (i.e., an increase in peribronchial leukocytes or an expansion of BALT).

Figures 20A, 20B, 20C:
FIGS. 20A–F. Goblet cell hyperplasia, epithelial hypertrophy, and collagen deposition are induced by airway expression of IL-5. Panels (a–c) are alcian blue (pH 2.5) staining of wild-type (+/+) (panel (a)) and NJ.1726 (panels (b, c)) lung sections. Panel (b) shows a bronchiole. Panel (c) shows a large bronchus. Intensely blue staining areas are glycoprotein (mucin)-containing goblet cells. Panels (d–e) are Masson's trichrome staining of paraffin sections derived from wild-type (panel (d)) and NJ.1726 (panels (e, f)) lungs. The darkly blue staining extracellular material is collagen. The arrows in panel (f) indicate hypertrophy in the bronchial epithelium. AE, airway epithelium; B, bronchiole; PV, pulmonary blood vessel; AS, alveolar space; BALT, bronchus-associated lymphoid tissue. Scale bars denote 50 lm (panels (a-14 e)) and 25 Em (panel (f)).
Figures 20D, 20E, 20F:
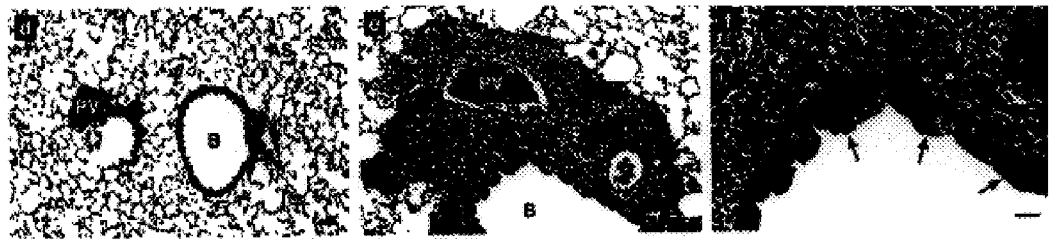

Additional histological analyses of NJ.1726 lungs demonstrated that other changes have also occurred as a consequence of airway expression of IL-5. Lung sections stained with alcian blue (pH 2.5) to detect weakly acidic sulphated mucins showed relatively few epithelial goblet cells in (+/+) animals (FIG. 20(*a*)). In contrast, NJ.1726 mice had an increase in the number, distribution, and staining intensity of goblet cells. These increases were evident in the epithelium of both bronchioles (FIG. 20(*b*)) and larger bronchi (FIG. 20(*c*)). Masson's trichrome staining (FIGS. 20(*d–f*)) demonstrated that the areas of expanded BALT in NJ.1726 lungs were often accompanied by the deposition of collagen (blue staining extracellular glycoprotein) and hypertrophy of the bronchial epithelium. A higher magnification view of the bronchiole and the surrounding BALT showed that the epithelial hypertrophy involved both ciliated and mucus-secreting cells (arrows in FIG. 20(*f*)). Interestingly all of these additional histopathologic changes were independent of the severity of the BALT expansion. Goblet cell hyperplasia, epithelial hypertrophy, and focal collagen deposition were observed in nearly all NJ.1726 mice and appear to be tightly linked to IL-5 airway expression.

Figure 21A:
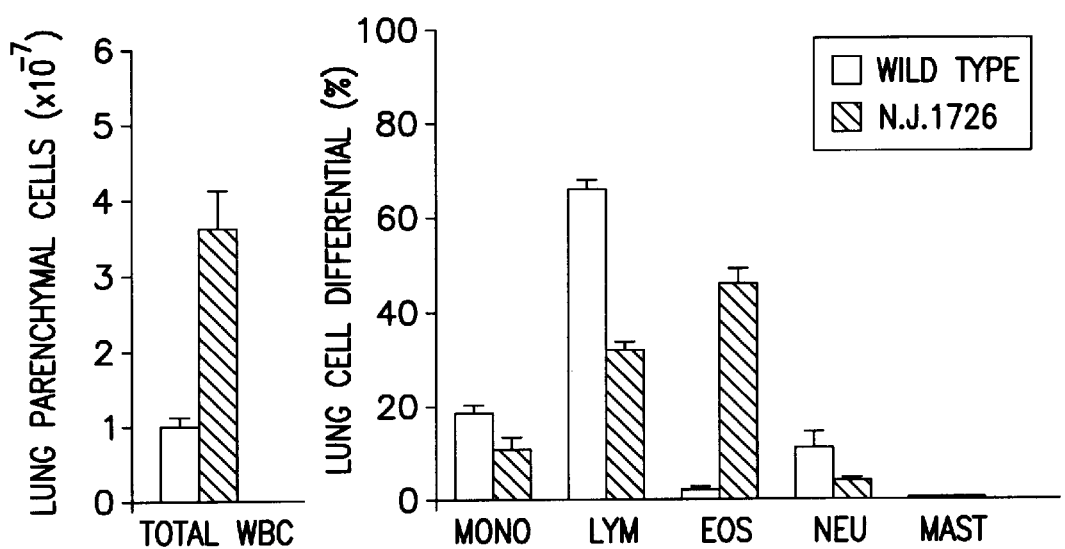
FIGS. 21A–B. Cell differentials and eosinophil-specific immunofluorescence demonstrate a dramatic peribronchial infiltrate. (A) Collagenase-digested perfused lungs from NJ.1726 mice (n=4) and transgenic negative littermates (n=3) were dispersed to single cell suspensions prior to the assessment of lung parenchymal cellularity. The total cell counts of lung parenchymal leukocytes are shown as the histograms on the left. The relative numbers of different types of leukocytes (lung cell differentials) were determined from Wright's stained cytocentrifuge preparations and are shown as the histograms on the right. These data are expressed as the means (±SD) of the percentage of each cell type derived from differentials based on 200 cells. Mono, monocytes and macrophages; Lym, lymphocytes; Eos, eosinophils: Neu, neutrophils; Mast, mast cells. (B) Parenchymal eosinophils were localized within the lung by immunofluorescence using an anti-mMBP polyclonal rabbit antiserum. Serial lung sections (4 um) were stained with HJE (panels 1, 4, 6), anti-mMBP serum (panels 2, 5, 7), and prebleed serum (panel 3) to visualize lung histology and eosinophil infiltration. These photographs represent serial tissue sections from a lung of an NJ.1726 mouse (panels 1–3, 4, 5) or a wild-type (+/+) control animal (panels 6, 7). B, bronchiole; PV, pulmonary blood vessel; AS, alveolar space; BALT, bronchus-associated lymphoid tissue. Scale bars 50 Wm.

The total cellularity and composition of the parenchymal infiltrate was determined by analyses of cells recovered from collagenase treatment of perfused lungs. Cell suspensions were prepared from collagenase treatment of perfused lungs as previously described (Hammelmann et al., *Am. J. Respir. & Crit. Med.* (1996)). The resulting cell counts and differentials are displayed in FIG. 21A. The total cellular infiltrate of NJ.1726 lungs increased four-fold relative to wild-type and was dominated by eosinophils (approximately 50%). The fractional increase of eosinophils occurred with decreases in the percentages of all other WBC types. However, if the increase in total lung parenchymal cells of NJ.1726 is taken into account, then the absolute numbers of all leukocyte populations increased relative to wild-type. Thus, in addition to a 57-fold increase in the numbers of parenchymal eosinophils, the absolute numbers of NJ.1726 lung lymphocytes and monocytes/macrophages in the lungs of transgenic mice increased relative to the lungs of wild-type by 1.8-fold and 2.1-fold, respectively.

Figure 21B:
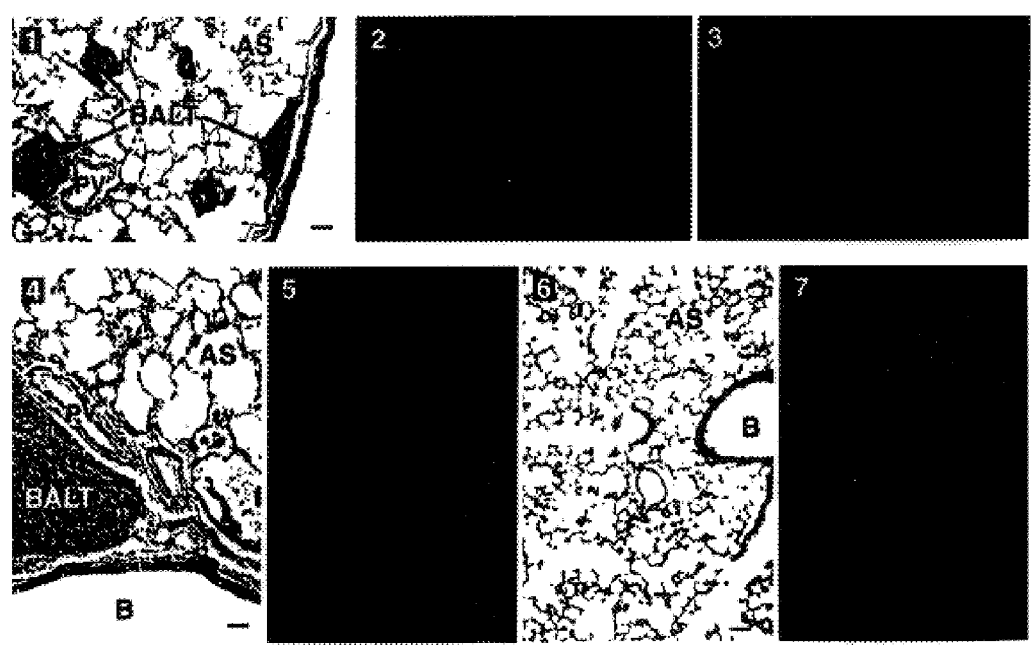

The presence of eosinophils infiltrating the peribronchial spaces was confirmed by immunofluorescence using a polyclonal antisera against mMBP, a specific marker for eosinophils (FIG. 21B). Serial sections from formalin-fixed paraffin-embedded tissue were placed onto TESPA-treated slides. The sections were deparaffinized using a xylene/ethanol/water gradient, treated for 30 minutes in 0.1% trypsin/0.1% CaCl (pH 7.5), rinsed well in water, and blocked overnight (>12 hours) in PBS/10% goat serum/0.1% sodium azide at 4° C. The blocked tissue sections were rinsed in PBS and then rabbit prebleed serum (diluted 1:20) or an anti-murine eosinophil granule major basic protein (mMBP) serum (diluted 1:20) was applied. Following the addition of the primary antibody, the slides were incubated for 45 minutes at 37° C. in a humidified chamber. The slides were washed with PBS (3×5 minutes each) and blocked with 0.1% Chromotrope 2R (J. T. Baker, Phillipsburg, N.J.) in PBS for 30 minutes at room temperature. The sections were rinsed in 2–3 changes of PBS and stained with a FITC conjugated anti-rabbit IgG (diluted 1:40, Sigma, St. Louis, Mo.) for 30 minutes at 37° C. The slides were washed in PBS (3×5 minutes each) and coverslips mounted using a mixture of 90% glycerol/10% PBS/0.1% p-phenylenediamine (Sigma, St. Louis, Mo.). Tissues were visualized and photographed using a compound fluorescent microscope (Zeiss Axiophot). Mature eosinophils were common in the peribronchial spaces of NJ.1726 mice and distributed throughout the lung parenchyma (FIG. 21B (panels 1–3)). Concentrated foci of eosinophils surrounding areas of BALT were also common (FIG. 21B (panels 4, 5)). The expanded peribronchial lymph nodes, the respiratory epithelium, and the airway lumen were virtually devoid of eosinophils. The immunofluorescence data also demonstrated that extensive areas of extracellular major basic protein were not detectable in the airway lumen, suggesting that the pathophysiologic changes observed in NJ.1726 mice were not the result of eosinophil degranulation and cationic protein deposition.

Figure 22A:
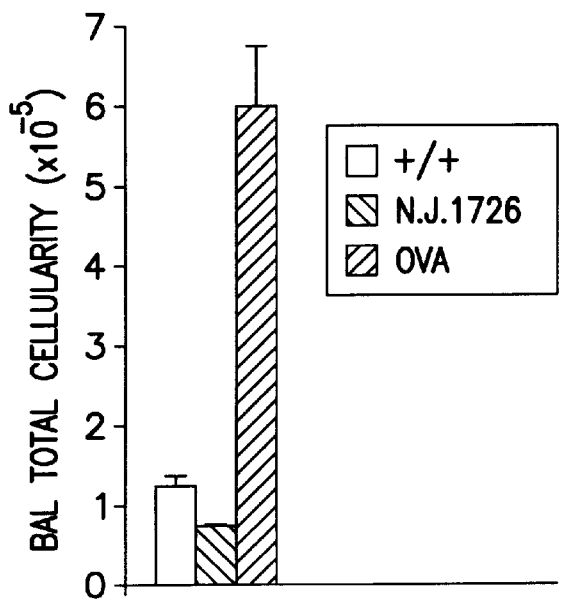
FIGS. 22A–B. Infiltration of the airway lumen by eosinophils did not occur as a consequence of the pulmonary changes in NJ.1726 mice. BAL cells derived from the lungs of 7 month old wild-type (+/+) (n=6), NJ.1726 (n=3), and, for comparison, control (+/+) animals (n=4) sensitized (i.p.) and challenged with aerosolized ovalbumin (OVA) (BAL cells assessed 2 days post-aerosol challenge) are displayed as histograms showing total BAL cellularity (left) and the relative numbers of different types of leukocytes (BAL differentials) determined from Wright's stained cytocentrifuge preparations (right). The fractional compositions of each cell type are expressed as percentages) derived from differentials of 200 cells. Data represent mean values ±SD. Mφ, macrophages, Lym, lymphocytes; Eos, eosinophils; Neu, neutrophils; Mast, mast cells.

Despite the massive infiltration of eosinophils in the peribronchial interstitium, a prominent eosinophil infiltrate of the airway lumen was not evident. FIG. 22 compares the total cellularity and composition of leukocytes found in the BAL fluid of wild-type (+/+), NJ.1726, and ovalbumin (OVA) sensitized/challenged (+/+) mice. Mice were sensitized/challenged with aerosolized chicken ovalbumin as described by Renz et al., *J. Allergy & Clin. Immunol.*, 89, 1127 (1967). The total number of BAL cells in NJ.1726 mice did not change appreciably relative to wild-type mice (+/+) ($1.06 \times 10^5$ vs. $0.87 \times 10^5$ cells, respectively) and showed only a small increase in the percentage of BAL eosinophils. This result was dramatically different from observations of BAL cells derived from OVA sensitized/challenged (+/+) mice. The respiratory inflammation induced in this mouse model resulted in a significant increase (approximately 6-fold) in total BAL cellularity that occurred almost exclusively as a consequence of an increase in the number of eosinophils recruited to the airway lumen (>60% of total BAL cells).

AHR in response to a cholinergic agonist is a physiologic perturbation characteristic of asthma and other respiratory disorders. In an attempt to correlate the IL-5 induced inflammatory changes in NJ.1726 mice to this response, airway responsiveness to methacholine challenge was measured.

Airway responsiveness was assessed by inducing airflow obstruction with a methacholine aerosol using a non-invasive method. Minute volume, tidal volume, breathing frequency, and enhanced pause (Penh) were obtained from conscious mice placed in a whole body plethysmograph (Model PLY 3115, Buxco Electronics Inc., Troy, N.Y.). Mice were unrestrained and tolerated repetitive measurements with this system. Chamber pressure was measured with a transducer (Model TRD 5700) connected to preamplifier modules (Model CHA 0150) and analyzed by System XA software (Model SFT 18110). The chamber pressure was used as a measure of the difference between thoracic expansion (or contraction) and air volume removed from (or added to) the chamber during inspiration (or expiration). The differential of this function with respect to time produced a pseudo-flow value that is proportional to the difference between the rate of change of the thoracic volume and nasal flow. Mice were placed in each chamber for 2 minutes and pulmonary airflow obstruction was assessed by measuring Penh using the following formula according to the manufacturer's recommendations: Penh=[(Te/0.3 RT)−1]×[2 PEF/3 PIF], where Penh=enhanced pause (dimensionless), Te=expiratory time (seconds), RT=relaxation time (seconds), PEF=peak expiratory flow (ml/s), and PIF=peak inspiratory flow (ml/s). The breathing pattern was collected for 2 minutes and an average of each variable was derived from 30 breaths (or 30 seconds, whichever occurred first). The peak Penh value was recorded. Measurements of methacholine responsiveness were obtained by exposing mice for 1 minute to saline, followed by incremental doses (2.5–320 mg/ml) of aerosolized methacholine (Model CN-25 Collision MRE type nebulizer BGI, Inc., Waltham, Mass.) and monitoring the breathing pattern for 2–3 minutes after challenge. Dose response data were plotted and the methacholine dose sufficient to double Penh ($ED_{200}$) was derived by log-linear interpolation. This procedure was completed within 60 minutes.

NJ.1726 mice, or wild-type animals, were exposed to increasing concentrations of aerosolized methacholine and AHR was measured by whole-body plethysmography. Data from transgenic and control animals (n=11 for each group) were collected as the means of duplicate single-animal measurements and are displayed in graphical form in the left panel of FIG. 22A. The effective doses of methacholine that achieved 50% maximal responsiveness ($ED_{200}$) are shown as histograms to the right of the primary data.

Figure 22B:
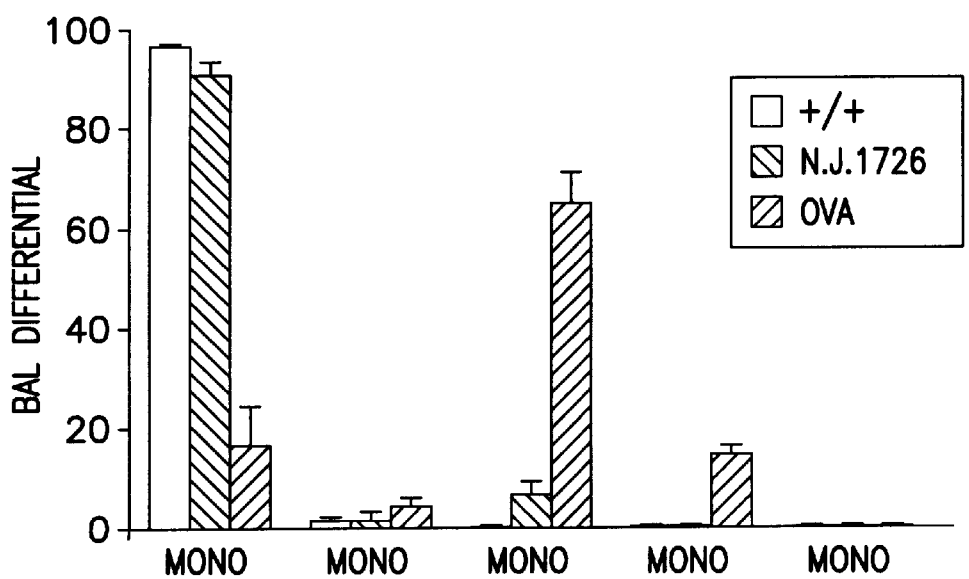
Figure 23A:
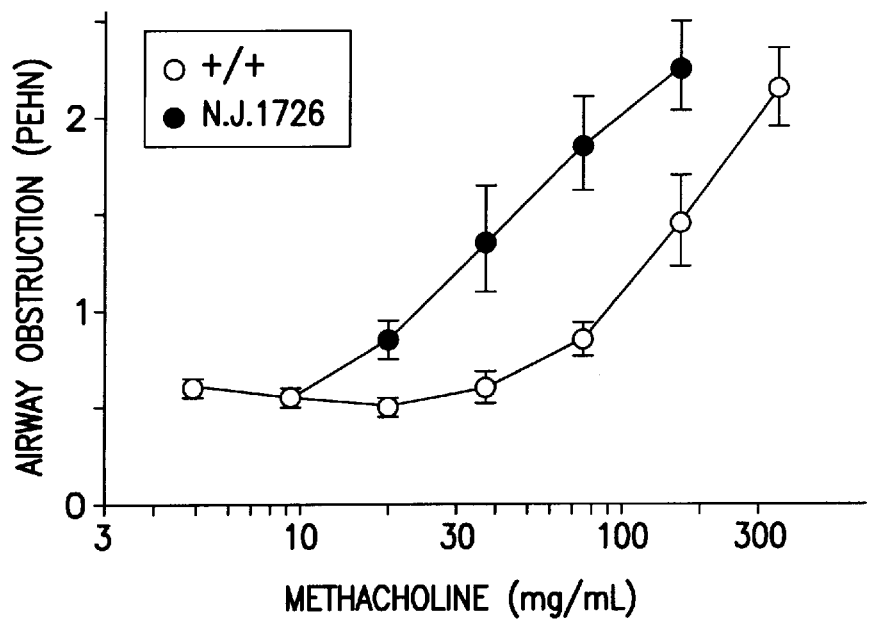
FIGS. 23A–D. AHR in the absence of antigen sensitization/challenge occurs only in lung-specific IL-5 expressing transgenic mice. Airway responsiveness of NJ.1726 mice (panel A) and transgenic mice expressing IL-5 from a T cell specific promoter (transgenic line NJ.1638) (panel B) was measured immediately after exposure to aerosolized methacholine. In each case, measurements were made relative to age matched (3–5 months) transgenic negative littermates. Mice were assessed on two occasions and the average for each animal was obtained. Values reported are group means ±SD (n=11). These data are used to derive the Effective Dose$_{200}$ levels (i.e., 50% maximal response), shown in the histograms to the left. The ED$_{200}$ for NJ.1726 transgenic mouse group was significantly different from the control wild-type mice (*p≦0.01).
Figure 23B:
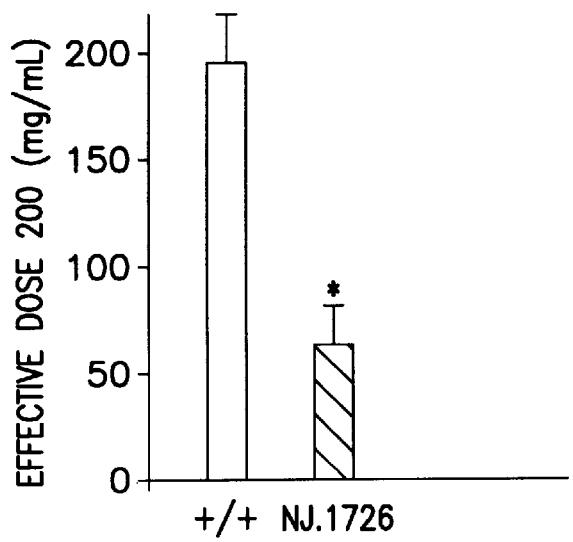
Figure 23C:
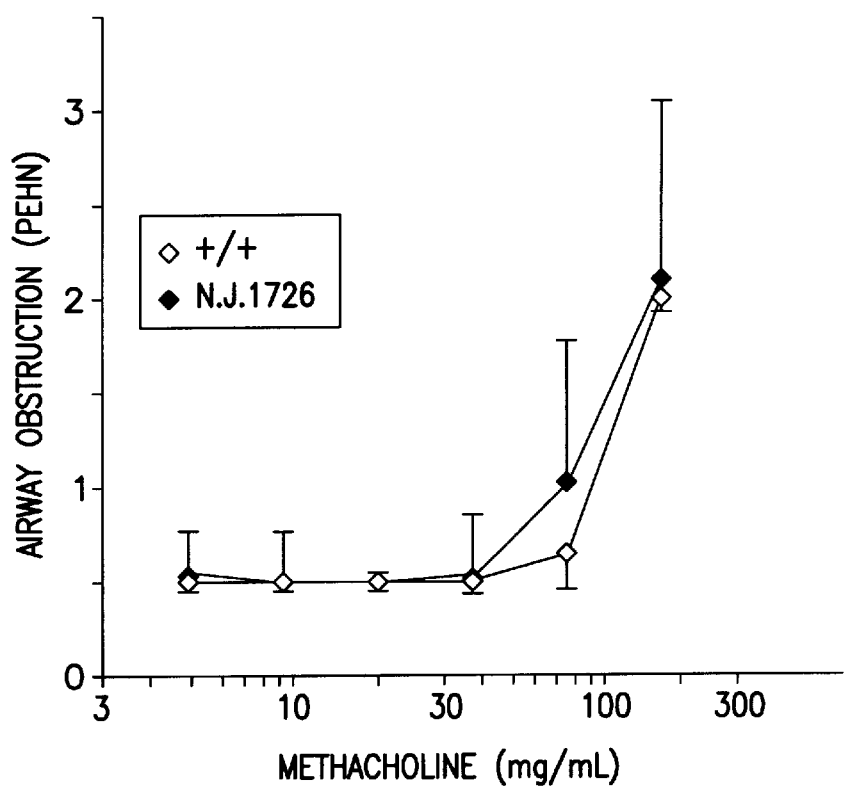
Figure 23D:
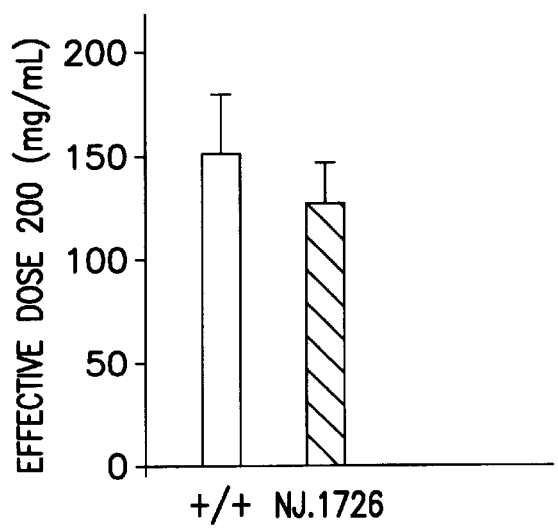

NJ.1726 mice had a lower threshold dose for methacholine-induced airflow obstruction compared with wild-type controls. In addition, NJ.1726 mice also displayed AHR to methacholine challenge in group mean dose-response data or when the mean of individual NJ.1726 $ED_{200}$ measurements were compared to the control animals (69 mg/ml vs. 197 mg/ml, respectively). This increase in AHR was restricted to lung-specific IL-5 expressing animals and was not observed in transgenic mice (line NJ.1638)

constitutively expressing high levels of serum IL-5 (FIG. 22B). This result is of particular significance because of the high WBC count (>400,000 cells/mm$^3$ of blood; ~60% eosinophils) and the ubiquitous presence of elevated levels of tissue eosinophils in these mice. Notably, the airway responsiveness displayed by NJ.1726 mice was achieved in the absence of an inflammatory stimulus (e.g., aerosolized antigen challenge). In relative terms, the increase in AHR observed in naive transgenic mice is comparable to that observed in ovalbumin sensitized/challenged C57BL/6J mouse models of asthma (3-fold vs. (3–5)-fold, respectively).

Discussion

The prominent changes observed in NJ.1726 mice were an expansion of BALT, goblet cell hyperplasia, epithelial hypertrophy, and an increase in peribronchial eosinophils. Areas of BALT in the lung are composed mostly of B-cells and have been suggested as regions of antigen uptake (Bienenstock, *Int. Arch. Appl. Immunol.*, 76, 62 (1985); Pabst and Gehrke, *Am. J. Respir. Cell & Mol. Biol.*, 3, 131 (1990)). In NJ.1726 mice, these areas are dominated by mononuclear cells (mostly lymphocytes) and thus the expansion of BALT may be a consequence of IL-5 proliferative effects on existing B lymphocyte populations (Lee et al., supra; Havada et al., *J. Immunol.*, 134, 3944 (1988)). If IL-5 effector functions rely in part on paracrine mechanisms, then the specific effects associated with the cellularity surrounding larger airways may be an indication of this regulatory loop. In addition to the effects on larger airway peribronchial lymph nodes, other histopathologic changes also occurred suggesting that chronic expression of IL-5 at an elevated level leads to generalized pulmonary distress. Collectively, these generalized changes (i.e., increased numbers of goblet cells, deposition of collagen among the leukocyte aggregates, and hypertrophy of the airway epithelium) occurred in nearly all transgenic animals and are consistent characteristics of several human inflammatory lung diseases (e.g., asthma (Busse and Sedgewick, *Ann. Allergy*, 68, 286 (1992); Verge et al., *J. Allergy & Clin. Immunol.*, 97, 1110 (1996); Sur et al., *J. Allergy & Clin. Immunol.*, 97, 1272 (1996)), chronic eosinophilic pneumonia, and bronchopulmonary aspergillosis) that are associated with increased IL-5 levels in the lung.

The infiltration of the peribronchial interstitium by eosinophils in the absence of antigen sensitization/challenge was a diagnostic phenotype. This infiltration, however, did not result in the subsequent recruitment of eosinophils into the airway lumen. Since allergic type I hypersensitivity (i.e., aerosolized OVA challenge) in wild-type mice induced a large airway lumen infiltrate dominated by eosinophils, the lack of eosinophils in the airspaces of NJ.1726 animals suggests specific differences exist between these models. It is likely that in addition to elevated levels of IL-5 expression, aerosolized OVA challenge also results in the expression of other signals (e.g., chemokines) that are critical for the activation and subsequent migration of eosinophils from the peribronchial spaces.

Expression of IL-4 using the rat CC10 promoter produces pathologic changes leading to the recruitment of lymphocytes and both eosinophils and neutrophils into the airway lumen (Raiken et al., *Proc. Natl. Acad. Sci. USA*, 93, 7821 (1996)). In addition, IL-4 expression elicited hypertrophy of the epithelium of the larger airways and increased the baseline airway resistance of transgenic lungs relative to wild-type controls. Moreover, IL-4 expression in the lung had no demonstrable effect on AHR in response to methacholine challenge.

Since the measured levels of IL-4 in the BAL fluid were only 4% of the IL-5 levels found in NJ.1726 mice, it is difficult to compare, in absolute terms, the effects of IL-4 versus IL-5 airway expression. However, several qualitative conclusions are worth noting. (1) Whereas the presence of IL-4 in the BAL of transgenic mice induced a leukocytic airway lumen infiltrate (5-fold relative to wild-type) that included macrophages (44%) and approximately equal numbers (i.e., 15–20%) of lymphocytes, eosinophils and neutrophils, expression of IL-5 at levels 23-fold higher did not alter total BAL cell numbers and induced only a small increase in BAL eosinophils. (2) Overexpression of either IL-4 or IL-5 in transgenic mice induced histopathologic pulmonary changes (e.g., epithelial hypertrophy and increases in BALT). The histopathologies reported here for IL-5 transgenic mice are more pronounced than the observed IL-4 pathologies. (3) Unlike the IL-4 transgenic mice, the expression of IL-5 in the airway lumen leads to AHR in the absence of antigen sensitization/challenge. Although AHR to methacholine challenge may also be a consequence of the higher level of cytokine expression found in NJ.1726 mice, this pathophysiologic response does correlate with the higher degree of histopathology observed in IL-5 transgenic mice.

The inability of IL-5 deficient mice to develop AHR and airway eosinophilia after ovalbumin sensitization/challenge suggested that IL-5 was required. Recently, Corry et al. (*J. Exp. Med.*, 183, 109 (1996)) reported that although treatment of mice with antibodies to IL-4 mimics the responses of IL-4 deficient mice, treatment with anti-IL-5 antibodies results in the elimination of eosinophil airway infiltration but has no effect on AHR in response to ovalbumin sensitization. Several explanations have been offered to resolve these differences (e.g., differences in sensitization protocols and inbred mouse strain variation); however, it is most likely that the antibody treatment protocols may have incompletely neutralized endogenous IL-5. This conclusion is supported by studies in ovalbumin sensitized/challenged guinea pigs in which low levels of anti-IL-5 antibodies inhibited eosinophil infiltration into the airways without affecting AHR, whereas high levels of anti-IL-5 antibodies eliminated both eosinophil recruitment and AHR (Mauser et al., *Am. Rev. Respir. Th.*, 148, 1623 (1993)). The implication is that airway eosinophilia and AHR are separate events. This effect, however, is more complex than cells within the lung responding to elevated levels of serum IL-5. Transgenic animals with high serum IL-5 levels derived from several non-lung cell types display no pulmonary pathologies (see FIG. 19(*e*)) and measurements of AHR in response to methacholine challenge showed that these mice also do not exhibit bronchial hyperreactivity in the absence of antigen sensitization/challenge (see FIG. 23).

The data reported herein support the independence of eosinophil infiltration of the airway lumen and the development of AHR. In the absence of a prominent leukocytic BAL infiltrate dominated by eosinophils, constitutive expression of IL-5 in the airways of mice at high levels was sufficient to induce the development of AHR. This phenomenon occurs in the absence of antigen sensitization/challenge and only in animals where the primary source of IL-5 is the lung. The observations presented cannot eliminate the possibility of IL-5 induced eosinophil effector functions mediated through either the large peribronchial infiltrate or the small influx of eosinophils into the airway lumen as factors in the development of AHR. However, the induction of this pathophysiologic response in NJ.1726 mice shows that AHR, a prominent airway lumen leukocytic infiltrate, and histopathologic pulmonary changes are not necessarily concomitant events. In this paradigm, ectopic lung-specific IL-5 expression reproduces some (e.g., elevated numbers of eosinophils and their specific recruitment to peribronchial spaces), but not all of the signals associated with allergic inflammation and the recruitment of eosinophils to the airway lumen.

EXAMPLE XII

Figure 24:
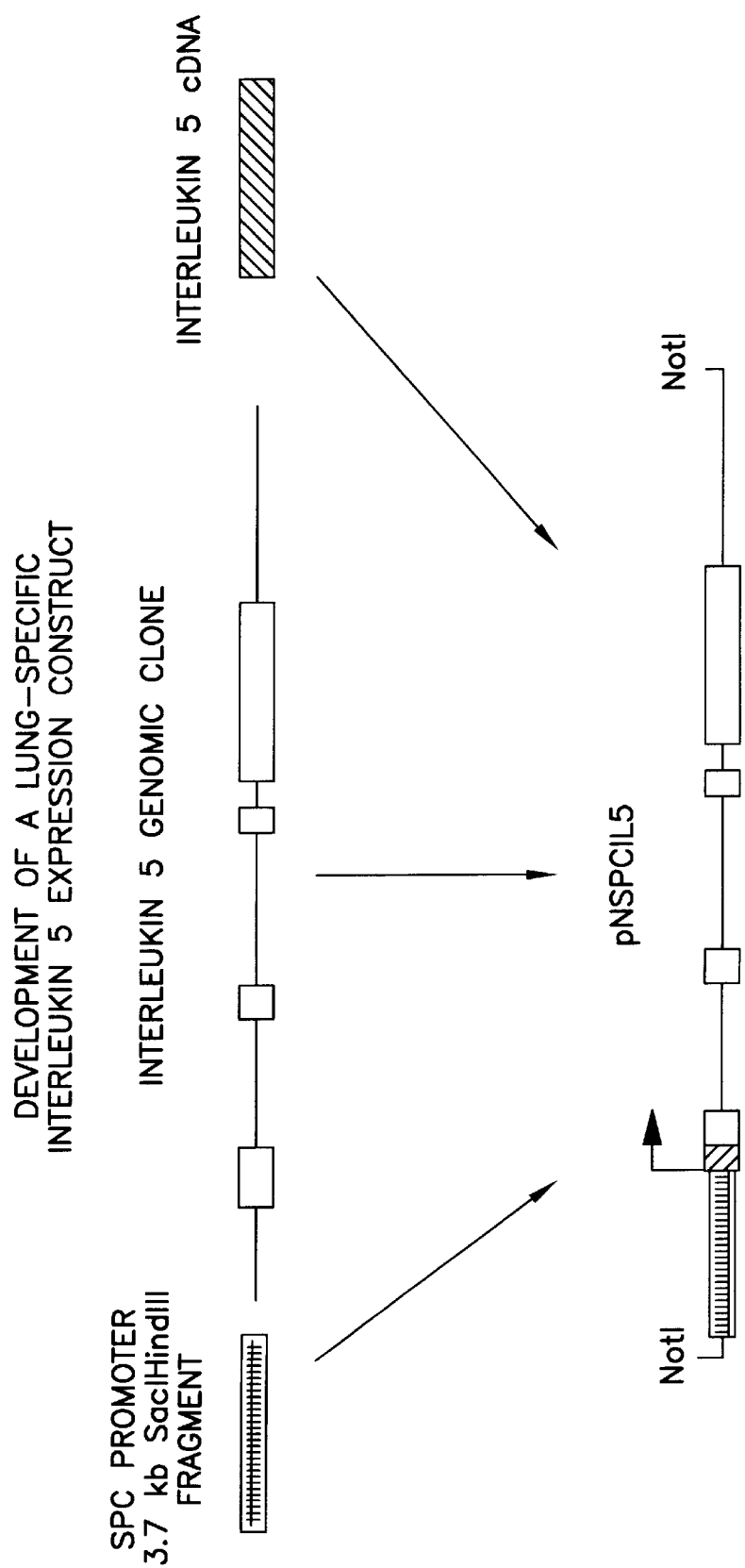
FIG. 24. Preparation of the surfactant protein C (SPC) promoter IL-5 transgene construct (pNSPCIL5). The construct was created as a cDNA:genomic fusion of sequences representing murine IL-5. The completed construct was cloned into the transgenic shuttle vector pNNO3 and the transgene insert was excised with Not I prior to introduction into fertilized eggs.

Generation and Characterization of Transgenic Mice Expressing IL-5 from the Surfactant Protein C Promoter in Lung Tissue Nine founder lines of transgenic mice were prepared that express the IL-5 gene from the surfactant protein C (SPC) promoter (Korfhagen et al., *Proc. Natl. Acad. Sci. USA*, 87, 6122 (1990); Wikenheiser et al., *Proc. Natl. Acad. Sci. USA*, 90, 11029 (1993); Peters et al., *EMBO J.* 13, 3296 (1994); Glasser et al., *J. Biol. Chem.*, 265, 21986 (1990)), a promoter which is expressed in type 11 pneumocytes of the lung. The construct was created by inserting a 3.7 kb SacI-HindIII restriction fragment containing the regulatory regions 5' to the SPC coding sequences into the multiple cloning site (MCS) of the pUC-derived plasmid pNNO3 (FIG. 24). A 5.5 kb BamHI IL-5 cDNA:genomic fusion gene (Lee et. al., *J. Immunol.*, 158, 1332 (1997)), which contains all of the IL-5 coding sequences but is devoid of any regulatory regions, was then cloned downstream of the SPC promoter fragment. The SPC/IL-5 sequences were excised from the plasmid vector with NotI digestion, gel-purified, and injected into mouse embryos for the production of the SPC/IL-5 transgenic lines.

Figure 25A:
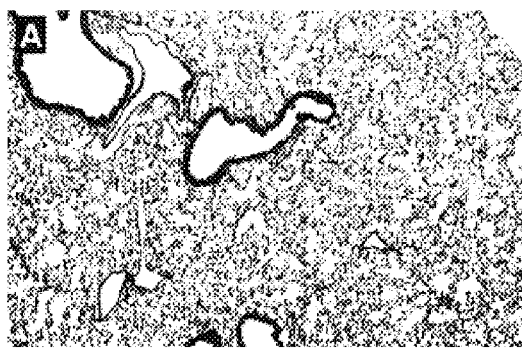
FIGS. 25A–D. Hematoxylin-eosin stained paraffin sections of the lung. (A) wild-type; (B) CCIL-5; (C) SPC/IL-5. Each photograph is a low power (5× view, mid-sagital. (D) Higher power (16×) close-up of the SPC/IL-5 lungs.
Figure 25B:
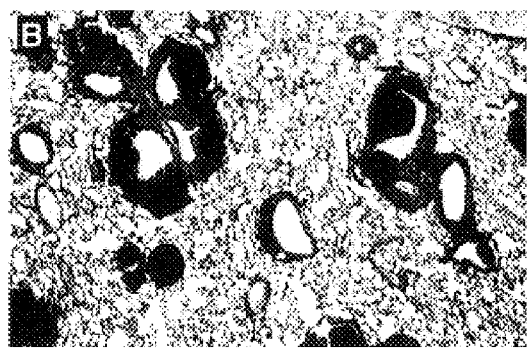
Figure 25C:
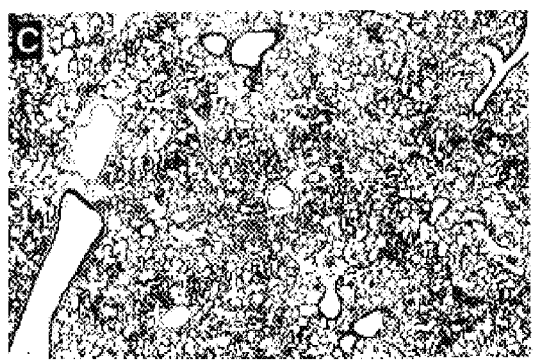

Each of the lines had elevated levels of eosinophils in peripheral blood and high levels of serum IL-5. In contrast to mice expressing IL-5 from the CC10 promoter in the lung epithelium (CCIL5), four of the nine SPCIL5 mice died before reaching four months of age. At necropsy, the lungs of these mice showed a massive inflammatory infiltrate (FIGS. 25A–C).

Figure 25D:
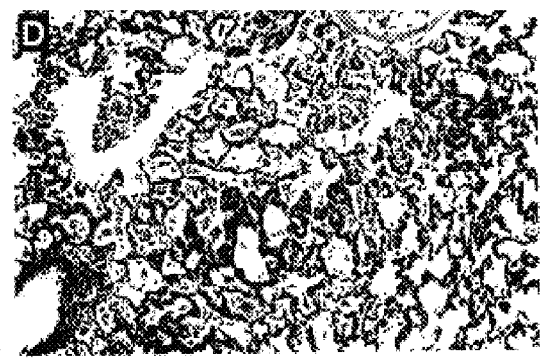
Figure 26A:
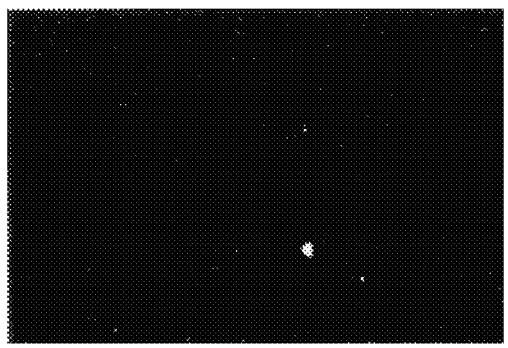
FIGS. 26A–B. In situ hybridization to sections from the lungs of SPC/IL-5 transgenic mice (16×). The left panel shows results with the anti-sense IL-5 probe; the right panel, the sense control probe.
Figure 26B:
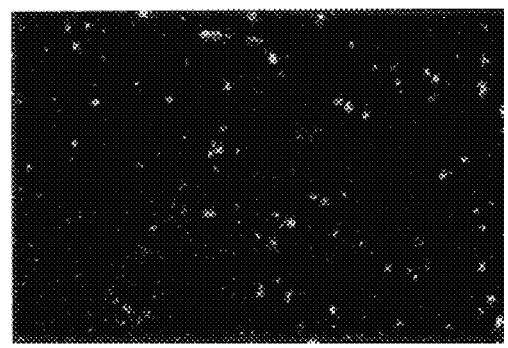

By two months of age, CCIL5 mice have increased cellularity in the lungs, and in particular in the peribronchial lymph nodes. At the same age, SPCIL5 mice showed increased lung cellularity throughout the parenchyma, but not in the peribronchial lymph nodes. The cells comprising the alveoli of the SPCIL5 mice were infiltrated with eosinophils and there was evidence of cellular migration into the airways (FIG. 25D). Moreover, in situ hybridization results showed that the SPC promoter is expressed specifically in the type II alveolar cells of the lung (FIG. 26). Thus, the cellular origin, rather than the level of expression, of IL-5 may be determinative of the histopathologies and severity of disease observed in different transgenic lines. Therefore, SPCIL5 mice may be useful as models in diseases such as asthma (extrinsic or intrinsic), eosinophilic pneumonia, eosinophilic myalgia, atopic disease, e.g., allergies or asthma, emphysema, or other diseases that result in limiting pulmonary function.

EXAMPLE XIII

Figure 27:
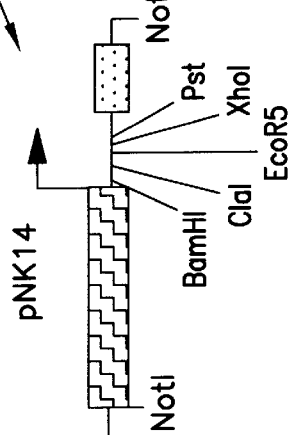
FIG. 27. Preparation of the construct to express IL-5 constitutively in keratinocytes (i.e., the skin) of mice. A cDNA/genomic IL-5 fusion construct was created such that the resulting fusion gene lacks any of the endogenous ILS 5' flanking regulatory sequences. Basal keratinocyte specific expression was achieved using the enhancer/promoter of the human keratin 14 gene (Genbank Accession No. U 11076).
Figure 27:
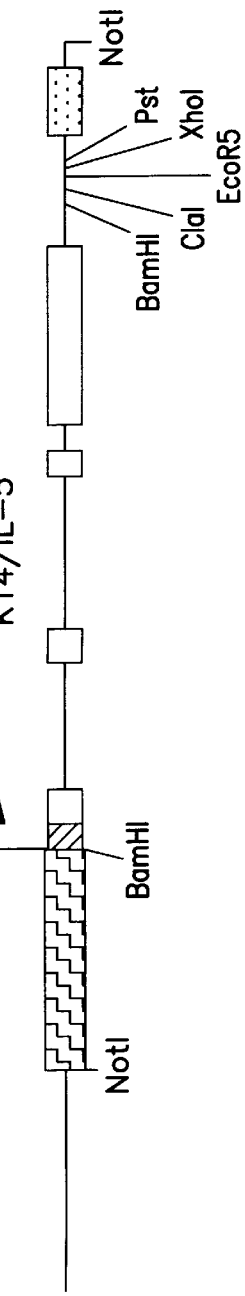

Generation and Characterization of Transgenic Mice Expressing IL-5 from the K14 Basal Keratinocyte-Specific Promoter Transgenic mice were also prepared that constitutively express the IL-5 gene from the K14 basal keratinocyte specific promoter. The construct was prepared by inserting a 1.9 kb EcoRI-BamHI restriction fragment containing the human Keratin14 (K14) regulatory elements (Turksen et al., *Proc. Natl. Acad. Sci. USA*, 89, 5078 (1992)) into the multiple cloning site (MCS) of the pUC-derived plasmid pNNO3 (Biogen, Cambridge, Mass.) (FIG. 27). Previous studies have shown that the K14 regulatory region of this gene directs high level expression of heterologous gene constructs in a keratinocyte-specific manner (Vassar and Fuchs, *Genes Dev.*, 5, 714 (1991)). A 0.5 kb BamHI-HindIII restriction fragment containing an intron and poly adenylation sequence from the K14 gene was also cloned into this MCS. A 5.5 kb BamHI IL-5 cDNA:genomic fusion gene (Lee et al., *J. Immunol.*, 158, 1332 (1997)), which contains all of the IL-5 coding sequences but is devoid of any regulatory regions, was then cloned into a BamHI site downstream of the human K14 promoter/enhancer fragment, but upstream of the intron/poly A sequences. Because the 5' terminal portion of the construct is derived from an IL-5 cDNA, all previously identified endogenous regulatory elements have been eliminated (Lee et. al., *J. Immunol.*, 158, 1332 (1997)). The K14/IL-5 sequences were excised from the plasmid vector with NotI digestion, gel-purified, and injected into mouse embryos for the production of the K14/IL-5 transgenic lines.

Several transgenic lines were generated from embryos of C57BL/6J mice and each transgenic line exhibited elevated levels eosinophils in the blood and skin. One line (NJ.692) was chosen for further study.

Figure 28A:
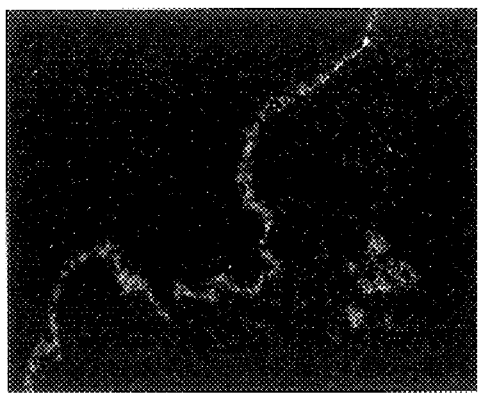
FIGS. 28A–B. In situ hybridizations to sections from the skin of an approximately 4 month old NJ.692 mouse. Dark-field analysis (5×) show that IL-5 expression is restricted to the basal keratinocytes. Hybridization with the anti-sense probe is shown in the left panel; the sense central is shown in the right panel.
Figure 28B:
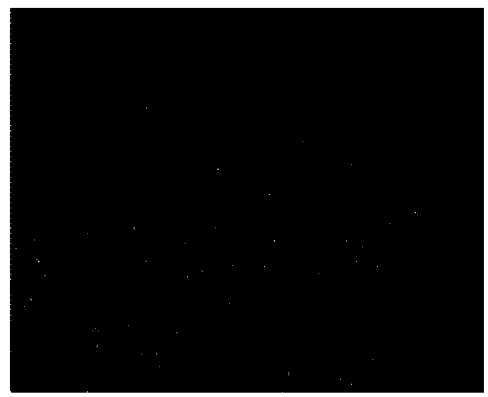
Figures 29A, 29B:
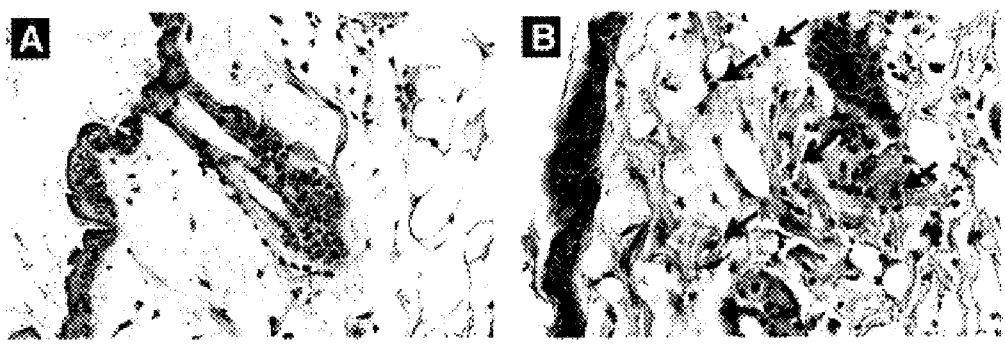
FIGS. 29A–B. Recruitment of eosinophils to the skin of NJ.692 transgenic mice. Each panel is a bright field image of a hematoxylin-eosin stained section from the skin of a (A) wild-type mouse (approximately 4 months of age), (B) an approximately 4 month old NJ.692 mouse (400×). The arrows in panel B indicate examples of the many infiltrating eosinophils found in the sections of transgenic skin.
Figure 30A:
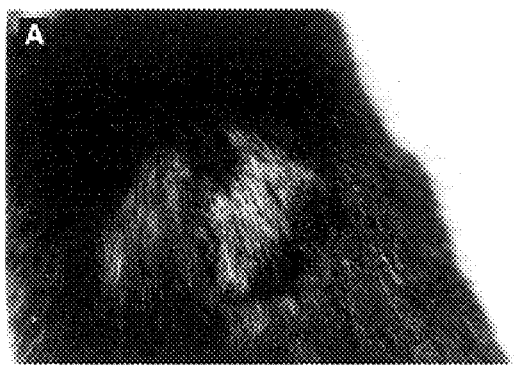
FIGS. 30A–B. Dermatological problems spontaneously occur in some NJ.692 mice. (A) Representative example of hair-loss (alopecia). The loss of hair is often associated with erythema and the loss of skin compliance. (B) Example of the ulcerating skin lesions that occur in NJ.692 mice.

In situ analyses of NJ.692 mice showed that IL-5 expression was restricted to the basal keratinocytes (FIG. 28). Initial histologic characterization of NJ.692 mice showed that eosinophil numbers in the skin of these mice rose dramatically (FIG. 29). This increase in skin-associated eosinophils occurred in animals of all age groups examined (0–6 months of age). Macroscopic observations of a small cohort of these animals during the same time period showed that among this group of mice, all individuals displayed a thickening of the skin and a loss of skin compliance. In addition, individual mice showed clinical signs of hair-loss (alopecia) and in some instances ulcerating skin lesions (see FIGS. 30A and B). These observations were loosely correlated with age, however, they were variable and not all individuals of a given age displayed these phenotypes.

Figure 30B:
Figures 31A, 31B, 31C:
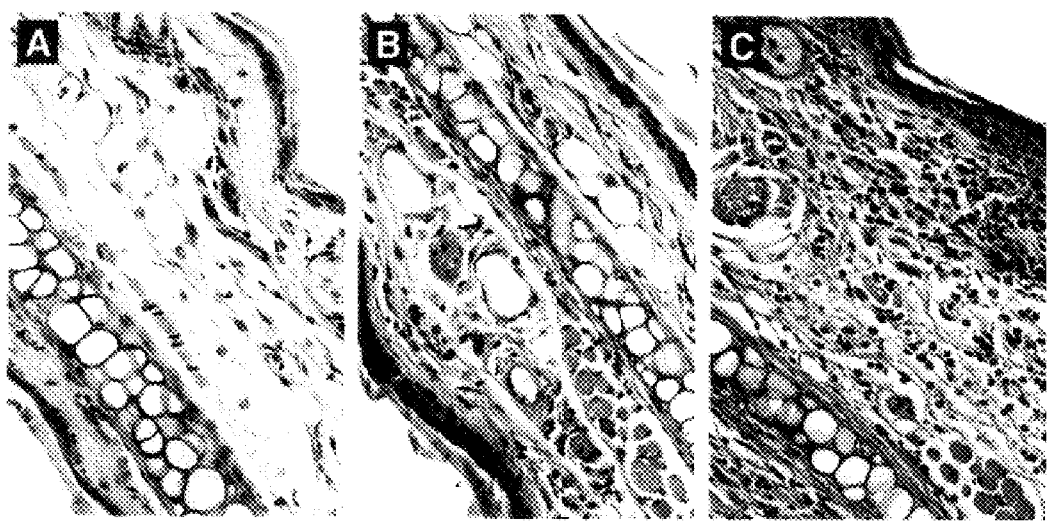
FIGS. 31A–C. Skin inflammatory response of NJ.692 mice to the contact hypersensitivity reagent oxazolone. Wild-type and NJ.692 mice were sensitized and then challenged with oxazolone. Each panel is a bright field image of a hematoxylin-eosin stained section from the skin of a (A) wild-type mouse, no oxazolone treatment; (B) wild-type mouse sensitized and challenged with oxazolone (48 hours post-challenge); (C) NJ.692 mouse sensitized and challenged with oxazolone (48 hours post-challenge). In all cases the magnification is the same (400×). Note the dramatic changes occurring in the NJ.692 mouse. These inflammatory reactions are characterized by exaggerated edema (i.e., swelling of the ear) and a massive cellular infiltrate of the affected area.

In order to demonstrate the utility of these mice as a model system to study eosinophil-mediated inflammatory reactions in the skin, NJ.692 mice were exposed to the chemical irritant oxazolone. The results from these experiments demonstrated that, relative to wild-type mice, transgenic NJ.692 animals undergo a substantially more robust inflammatory reaction (assessed by ear-swelling). FIG. 30 also shows that the skin cellular infiltrate of NJ.692 animals was dominated by eosinophils. This result was unique to NJ.692 skin and not observed in wild-type animals (compare FIGS. 31B to 31C).

The invention is not limited to the exact details shown and described, for it should be understood that many variations and modifications may be made while remaining within the spirit and scope of the invention defined by the claims.

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

ACCCCACACC TAGCCCACTG                                          20

(2) INFORMATION FOR SEQ ID NO:2:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

TGGCAGTGGC CCAGACACAG C                                        21

(2) INFORMATION FOR SEQ ID NO:3:

(i) SEQUENCE CHARACTERISTICS:
       (A) LENGTH: 1560 base pairs
       (B) TYPE: nucleic acid
       (C) STRANDEDNESS: single
       (D) TOPOLOGY: linear (ii) MOLECULE TYPE: Genomic DNA (xi) SEQUENCE DESCRIPTION: SEQ ID NO:3:

CGGGATTTTG CTGCCTTACC ACAGCCCAAA GCAGGCTGTG TGTTTAGAAG CTGAGCCACA      60

AAGAAGTTTC CATGACATCA TGAATGGGGG TGGCAGAGAA GAATATTGGG GCTCAGAGGG     120

TGTGTGTGTG TGTGTGTGTG TGTGTGTGTG TGTGTGTGTG AGAGAGAGAG AGAGAGAGAG     180

AGAGAGAGAG AGACAGACAG AGAGACAGAG AGACAGAAAG ACAGAAAGAC AGAAAGACAG     240

AGACAGAGCT GTCAAGAATT TTCTTCTACT TCGTGGGTTC TGGGGATTGT ACTAAGGTCA     300

TGAGGCTTGT GTGGCAAGCA CCCTTACCCA CTGAGCCATC TTGCCTGCCC TCATCCTCAA     360

ATTAATTAAA AATAAAGAAC ATGATGAATT GACGCCAGTG CCAAGCTAGC GGCCGCGGTC     420

CAACCACCAA TCTCAAAGCT TGCATGCCTG CAGGTCGACT CTAGAGGATC AGCCAGGGTT     480

TAGCACTATC CTCCGCCAAC AGACTCATGG GTATTCAGAA AAAGGAAGAG TGGGGGAGGA     540

ACTAGAAGAA ATCTGCCTCT CTACCTTCTG CCTTTGATGG TGTAAGACTG TCAAAGCAAC     600

AGTGGGCTAG GTGTGGGGTA AGACACAAAC AGGTGCAAAC TGCTCTTTCT GAAGCAAAGA     660

GTTTGGGATG ATTGATACAA AGCAGAGACT ATGCATGGAT CCGAATTCAT CATGTTCCTT     720

TATTTTTAAT TAATTTGAGG ATGAGGGCAG GCAAGATGGC TCAGTGGGTA CCACGATTGA     780

GAAGAAAATC TTGACAGCTC TGTCTCTGTC TTTCTGTCTT TCTGTCTTTC TGTCTCTCTG     840

TCTCTCTGTC TGTCTCTCTC TGTCTCTCTC TCTCTCTCTC TCTCTCACAC ACACACACAC     900

-continued

```
ACACACACAC ACACACACAC ACACCCTCTG AGCCCCAATA TTCTTCTCTG CCACCCCCAT      960

TCATGATGTC ATGGAAACTT CTTTGTGGCT CAGCTTCTAA ACACCACACC TGCTTTGGGC     1020

TGTGGTAAGG CAGCAAAATC CCGGAAGTTG TTATGATAGG GACTGGAACC AACAGGCAAT     1080

GAAGCAGAGT GGCTGGGCTG ACCCTGCCCA CGGAAACCCA CAGGGTTAGA AATGCCAAGG     1140

GGCCAGGATG GGAAGCTGTC CCTCGTACTG CCTGTCTGGG TCTGAGGAGA GGAAGCCAGA     1200

AGTGAGGGGC CACGGGTGGG CAGAACTCAG CCAAGCTAAG ACAACTCTCA ATCCATGCTT     1260

TGGAAAACAC AGGCGCGGAT CCTCACATCC CAATCCGCGG CCGCAATTCG TAATCATGGA     1320

ACAAACTTTC CTCATAGTCT CTGCTTTGTA TCAATCATCC CAAACTCTTT GCTTCAGAAA     1380

GAGCAGTTTG CACCTGTTTG TGTCTTACCC CACACCTAGC CCACTGTTGC TTTGACAGTC     1440

TTACACCATC AAAGGCAGAA GGTAGAGAGG CAGATTTCTT CTAGTTCCTC CCCCACTCTT     1500

CCTTTTTCTG AATACCCATG AGTCTGTTGG CGGAGGATAG TGCTAACCCT GGCTGATCAT     1560
```

(2) INFORMATION FOR SEQ ID NO:4:

(i) SEQUENCE CHARACTERISTICS:
        (A) LENGTH: 1534 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: mat_peptide
        (B) LOCATION: 104...442
        (D) OTHER INFORMATION:

(xi) SEQUENCE DESCRIPTION: SEQ ID NO:4:

```
CGCTCTTCCT TTGCTGAAGG CCAGCGCTGA AGACTTCAGA GTCATGAGAA GGATGCTTCT       60

GCACTTGAGT GTTCTGACTC TCAGCTGTGT CTGGGCCACT GCCATGGAGA TTCCCATGAG      120

CACAGTGGTG AAAGAGACCT TGACACAGCT GTCCGCTCAC CGAGCTCTGT TGACAAGCAA      180

TGAGACGATG AGGCTTCCTG TCCCTACTCA TAAAAATCAC CAGCTATGCA TTGGAGAAAT      240

CTTTCAGGGG CTAGACATAC TGAAGAATCA AACTGTCCGT GGGGGTACTG TGGAAATGCT      300

ATTCCAAAAC CTGTCATTAA TAAAGAAATA CATTGACCGC CAAAAAGAGA AGTGTGGCGA      360

GGAGAGACGG AGGACGAGGC AGTTCCTGGA TTACCTGCAA GAGTTCCTTG GTGTGATGAG      420

TACAGAGTGG GCAATGGAAG GCTGAGGCTG AGCTGCTCCA TGGTGACAGG ACTTCACAAT      480

TTAAGTTAAA TTGTCAACAG ATGCAAAAAC CCCACAAAAC TGTGCAAATG CAAGGGATAC      540

CATATGCTGT TTCCATTTAT ATTTATGTCC TGTAGTCAGT TAAACCTATC TATGTCCATA      600

TATGCAAAGT GTTTAACCTT TTTGTATACG CATAAAAGAA ATTCCTGTAG CGCAGGCTGG      660

CCTCAAACTG GTAATGTAGC CAAGGATAAC CTTGAATTTC TGATCCTCCT GCCTCCTCTT      720

CCTGAAGGCT GAGGTTACAG ACATGCACCA TTGCCACTAG TTCATGAAGT GCTGGAGATG      780

GAACCCAAGG CTTTGTGCAT GTTACCAACT GAGTTATACT CCCTCCCCCT CATCCTCTTC      840

GTTGCATCAG GGTCTCAAGT ATTCCAGGCT GACTTTGAAC TCAGTGTGTA GCCAAGGGTG      900

ACCCTGAACT CTTGGTCCAG ATGGACGCAG GAGGATCACA TACCCAACCT TAGCATCCTT      960

TCTCCTAGCC CCTTTAGATA GATGATACTT AATGACTCTC TTGCTGAGGG ATGCCACACC     1020

GGGGCTTCCT GCTCCTATCT AACTTCAATT TAATACCCAC TAGTCAATCT CTCCTCAACT     1080

CCCTGCTACT CTCCCCAAAC TCTAGTAAGC CCACTTCTAT TTCTTGGGGA GAGAGAAGGT     1140
```

-continued

```
TGACTTTTCT TATGTCCTAT GTATGAATCA GACTGTGCCA TGACTGTGCC TCTGTGCCTG      1200

GAGCAGCTGG ATTTTGGAAA AGAAAAGGGA CATCTCCTTG CAGTGTGAAT GAGAGCCAGC      1260

CACATGCTGG GCCTTACTTC TCCGTGTAAC TGAACTTAAG AAGCAAAGTA AATACCACAA      1320

CCTTACTACC CCATGCCAAC AGAAAGCATA AAATGGTTGG GATGTTATTC AGGTATCAGG      1380

GTCACTGGAG AAGCCTCCCC CAGTTTACTC CAGGAAAAAC AGATGTATGC TTTTATTTAA      1440

TTCTGTAAGA TGTTCATATT ATTTATGATG GATTCAGTAA GTTAATATTT ATTACAACGT      1500

ATATAATATT CTAATAAAGC AGAAGGGACA ACTC                                  1534

(2) INFORMATION FOR SEQ ID NO:5:

(i) SEQUENCE CHARACTERISTICS:
        (A) LENGTH: 6727 base pairs
        (B) TYPE: nucleic acid
        (C) STRANDEDNESS: single
        (D) TOPOLOGY: linear (ii) MOLECULE TYPE: Genomic DNA (ix) FEATURE:

(A) NAME/KEY: mat_peptide
        (B) LOCATION: 650...3771
        (D) OTHER INFORMATION: Join 650..730, 1560..1592, 3468..3596,
            3676..3771

(xi) SEQUENCE DESCRIPTION: SEQ ID NO:5:

TGTACCTCCC ACATCTGCTG GTGTGTACCA CCACACCTAG TAAGATATTC TCAACATTTA       660

TGTATTTTAG CCTAACCCTG TTGGAGGTAT ACATTTGAAT ACATTTTTTC TCACTTTATC       120

AGGAATTGAG TTTAACACAT ATTAAAGCAG GTGTGGGGCA GGGAGGGGGG GATAAAAAAG       180

AAGGTGCTCA AGAAAAGCCG ATCACGCTCC CAAGAGTGTG AGCATGGGCG TCTCTAGAGA       240

GATCCGCCAT ATATGCACAA CTTTTAAAGA GAAATTCAAT AACCAGAATG GAGTGTAAAT       300

GTGGATCAAA GTTGTAGAAA CATTCTTTTA TGTTATAGAA AATGCTTTTT AAGCAGGGGT       360

GGGGGTCAAG ATGTTAACTA TTATTAAAGA GCAAAAAAAA AAAATGCAT TTTGTTTGAA        420

GACCCAGGGC ACTGGAAACC CTGAGTTTCA GGACTCGCCT TTATTAGGTG TCCTCTATCT       480

GATTGTTAGC AATTATTCAT TTCCTCAGAG AGAGAATAAA TTGCTTGGGG ATTCGGCCCT       540

GCTCTGCGCT CTTCCTTTGC TGAAGGCCAG CGCTGAAGAC TTCAGAGTCA TGAGAAGGAT       600

GCTTCTGCAC TTGAGTGTTC TGACTCTCAG CTGTGTCTGG GCCACTGCCA TGGAGATTCC       660

CATGAGCACA GTGGTGAAAG AGACCTTGAC ACAGCTGTCC GCTCACCGAG CTCTGTTGAC       720

AAGCAATGAG GTAAAGTATA ACTTATTCCT TCAGCTTTGT TTTTAAGATC AGGACCTTGC       780

TATACCGCTC TGACTGGCCT CAAACTTGCT ATGTAGGGTA GGCTGTCCTA ACCCCTACCA       840

GATCTCCTTA CCTATGTCTC CCAAATACTA GGATTACAGA CACATTACCT TGCCTGACGC       900

TATGGTTCTT CAGAATGCAT AAATAGCTGC ATTTGGCCTT TAATCCCAGA ACTTGGGAGG       960

CAGGGTCAGG TGGATCTCTG TGAGTTCAAG GCCAGACTTG TCTACGTGGC CAGTTACAGG      1020

ACAGCCAGAG CTAAAGCAAG ACCCTGATTC AAAATAATTT TTTTTCAAAA CAAAAAAAAA      1080

AAACCCAAAC CATTTGTGGC AATTCATTTC TAAACATAAA GATCTGCTTT AAATAGTGCA      1140

ATTATGGCTT GTTCCCTTGC CTTCTTGCTC CCGTTCTGTC CTCTTGTCCC ACTCTCTCCC      1200

CATTCCACCC CCACCATGTG CTCATGGCCC GCATCTCTAC TTCTCTACTC TCTTTCTCTC      1260

CCTCTCCCCT CCTTCTTCCT TTCCCTCTCT CTCTCCCTCT TCTTCTCCTC CTCTCTTTCT      1320
```

```
CTCTCTCTCC CTCTCTCTCT CTCTTTCTCT CTCTCTCTGC TTTTTTCTAT CTCTACTACC    1380

CTCTCAACTC CCCTCTCCAT GCCCTGAATA AGCTCTATTC TATACTAAAA AAAAAAAGT    1440

GCAATTATGA ATGTGTTAGT GTTAATGCAC AGGTGATAAC CCTATCACCA GCAAGCATTG    1500

CATTAAAAAA GGCAACGGAC TCTCTTTAGG ATGACCCTAT GATGTTCTTT CCTTTGCAGA    1560

CGATGAGGCT TCCTGTCCCT ACTCATAAAA ATGTAAGTTA TTCTTTACTG CCGTGCTTGC    1620

ATGAGTAAGT CAGCTTCGCA TACTAAGCTA TAAGTCATCT GCATCTAGCT TTCTGGTGTT    1680

GTGTGTGTCT GGGATGGGGA CCTCTCTAGG TCTCAAGCTC CTGGGTTCAA GTGATTCTCT    1740

TGCCTTGATA GAGCAGCTGG GACACAGGCC TGTGCCACCA CACCCAGCAG AGCTTTTGAT    1800

TTCAGTTAAA CTGTTTGACT TTCTTGGAAA AGAAAATTTA TGTAGGTAGA TATGAAAGTT    1860

TGTGCTTATA AATAAAAAGA ATATGAGAGT GGCAAATTAT GTAATCCAG TACTTGGGAG    1920

CCAAAGGCAG GGGTAGTCTG AGTCTAGGGC CAGCTTAGAT ACATTGCCCT GTATGTATCA    1980

AAAGTAAATC CTATAAATAA ATAAACAAAA ACATTAGAGG GCTGGAGATA TAAGCTCTGT    2040

TGATAGATGG CCTAATATGC TGGGTTGACT CTTAGCACCC CATAAACTAA ACATGGAAGT    2100

ACCTGGCTGT AATCTCATGA TGGTGAAATG GAGGCGGGAA GATCATAGGT TCAAGGTCAT    2160

CCTCAGCTAC ATTTTTGAGC TAGAGGCCAG CCTGGGCTAT GAGACACGCA AAAACCACCA    2220

GCCAATTAAT ATTAGGAATG GCTTTGAGCT AGATCTGTTA TGTAAGTGGC CAGCTGGAGC    2280

TGTCAGTCAT ACATCTCACA GCCTCACAAG ATTCTTTGCA TGGCGAGAGG TCCTGCTGGG    2340

CTCCCTTTGG CTCTGTCCAT GGCTCTCTTC ATCCTAGTGC CTCTCTTTGT TTTCCTTGTC    2400

TTATTTCTTA CTGCTGAGGA TCAAGCCCAG GGCCTTCAGT GTGTGAAGTG AGCACTCTAC    2460

CACTGAATTC CAGAGCCCGC CCACTCTAAT GCCTTTCTGA AAGTATTAAG AGTTTAGGGT    2520

TATATATTCC TTTTGTTTAT TTTATGTGTA TGAGCATTTT GCCTGCATAT ATATATATAT    2580

ATATATATAT ATATATATAT GTGTGTGTGT GTGTGTGTGT GTGTGTATAT ATATATGTAT    2640

GTATGTATGT ATGTATGTAT GTATGTATAT GTGTGTGTGT GTGTGTGTGT GTGTGTGTGT    2700

GTTCCACGTA TGTGTCTATG TGTCTGGTGT TCCTGAAGGC TAAAAGAAGG GCATCAGATC    2760

ACCTGGGGCT GGATATGCAG ATGGTTGTGA GCCAACCATC TGGATGCTGG GAACTGCATC    2820

AAGTGTTCTT AACCACTGAG CCATCTCTCC CGCTCAGAGG GTTATATTCT TAGGTAATGA    2880

TAGAAAGACA TAAAAATATC ATGAATGCCT TTATTAATAA TTTCTAAACA GTTAATGAA    2940

TATGACTATG TAGTGATATT GTATACATTT CAATATTATC TTATTCTAGC GTAAAGTACA    3000

TTATTTAACT TTTTCTAAAT AGAAGAAAAT TCATCAGCCT AAATTTCAAA AGAAAATATT    3060

AATATGGGTG TGGTACCACT CACCTTTAAT CCAGATGGTT GTGAGCCACC ACAAGGGTGC    3120

TGGTAACTGA ACCCAGGTCC TCTGGAAGAG GACCCAGTGA TCTTAACCAC TGAGCCATCT    3180

CCCCAGCCCC AATCCTAACT TTGGGTTCAT TTTTTTGAAA TGATCTCATG TAGCACTAGC    3240

TGGCCTCAAA CTCTATGTAT CAGAGGCTGG CCTTCAACTC CTGATCCTCT TACCTCAACT    3300

TCCTGAATGC TGGCATTACA GATAAGCACC ATCACATCTT GTATTGTCTG GGGTTTTTA    3360

TTGATGCATT TAAATTGCAT GTATTTATTG CATATGGCAT GATATTTCAA AATATGTGTA    3420

CGTTGTGGGC AGTCTGATCT ATTTGCTTCT TGATAATCTT CTTTCAGCAC CAGCTATGCA    3480

TTGGAGAAAT CTTTCAGGGG CTAGACATAC TGAAGAATCA AACTGTCCGT GGGGTACTG    3540

TGGAAATGCT ATTCCAAAAC CTGTCATTAA TAAAGAAATA CATTGACCGC CAAAAAGTAA    3600

GTTCCCCAGG GACCCTGTGA ATCCGGCTGC AGCTGGTTCT CCAGGAGCCA ACCTGACAGT    3660

CTGTTCTTTT CACAGGAGAA GTGTGGCGAG GAGAGACGGA GGACGAGGCA GTTCCTGGAT    3720
```

```
TACCTGCAAG AGTTCCTTGG TGTGATGAGT ACAGAGTGGG CAATGGAAGG CTGAGGCTGA    3780

GCTGCTCCAT GGTGACAGGA CTTCACAATT TAAGTTAAAT TGTCAACAGA TGCAAAAACC    3840

CCACAAAACT GTGCAAATGC AAGGGATACC ATATGCTGTT TCCATTTATA TTTATGTCCT    3900

GTAGTCAGTT AAACCTATCT ATGTCCATAT ATGCAAAGTG TTTAACCTTT TTGTATACGC    3960

ATAAAAGAAA TTCCTGTAGC GCAGGCTGGC CTCAAACTGG TAATGTAGCC AAGGATAACC    4020

TTGAATTTCT GATCCTCCTG CCTCCTCTTC CTGAAGGCTG AGGTTACAGA CATGCACCAT    4080

TGCCACTAGT TCATGAAGTG CTGGAGATGG AACCCAAGGC TTTGTGCATG TTACCAACTG    4140

AGTTATACTC CCTCCCCCTC ATCCTCTTCG TTGCATCAGG GTCTCAAGTA TTCCAGGCTG    4200

ACTTTGAACT CAGTGTGTAG CCAAGGGTGA CCCTGAACTC TTGGTCCAGA TGGACGCAGG    4260

AGGATCACAT ACCCAACCTT AGCATCCTTT CTCCTAGCCC CTTTAGATAG ATGATACTTA    4320

ATGACTCTCT TGCTGAGGGA TGCCACACCG GGGCTTCCTG CTCCTATCTA ACTTCAATTT    4380

AATACCCACT AGTCAATCTC TCCTCAACTC CCTGCTACTC TCCCCAAACT CTAGTAAGCC    4440

CACTTCTATT TCTTGGGGAG AGAGAAGGTT GACTTTTCTT ATGTCCTATG TATGAATCAG    4500

ACTGTGCCAT GACTGTGCCT CTGTGCCTGG AGCAGCTGGA TTTTGGAAAA GAAAAGGGAC    4560

ATCTCCTTGC AGTGTGAATG AGAGCCAGCC ACATGCTGGG CCTTACTTCT CCGTGTAACT    4620

GAACTTAAGA AGCAAAGTAA ATACCACAAC CTTACTACCC CATGCCAACA GAAAGCATAA    4680

AATGGTTGGG ATGTTATTCA GGTATCAGGG TCACTGGAGA AGCCTCCCCC AGTTTACTCC    4740

AGGAAAAACA GATGTATGCT TTTATTTAAT TCTGTAAGAT GTTCATATTA TTTATGATGG    4800

ATTCAGTAAG TTAATATTTA TTACAACGTA TATAATATTC TAATAAAGCA GAAGGGACAA    4860

CTCAAATTCA GTTTGCTATT GGTCTTTTCT AACCCTGGGT GTGTGCAGGG ACCCAGAGGA    4920

GAGACTGAGT ATGTCCTGAC TAAGCACTTT CAGCTCCTTA GAGCTTCAGG GAGCACCAAG    4980

GGTGGACTTG GTAGTGGTAT CGGGAGCAAG AACAAGGGCT GGGACTGAGC CTGGATCTCC    5040

CTATGTAGGA GTATGTCCAG ATGGCTCAGG GTGAACAGGA GAGGAATGAA TGAGAGGATG    5100

AATGAATGAA TGAATAAATG AATGAATGGG AGATCGCTCC ATTAATAAAG TGCTTGCTGT    5160

ACAAGGATGA AGAGCTGAGT TCGAGCTCCA AAACCCATTT CAGAAAGCTG GCATGGTGG    5220

GGGCACACTT GTAGTCCTGA CACTGGGAGA CAGAAATAGC CAGATCCCTG GGGCTCTCTG    5280

TTCAGCCAAC CTAAATGAAT TGGTGAGTTC TGGACCAGTG AGAGATCTTC TCTCAAAAAG    5340

CAAGGTGGAA GCCGAGCGTG GTGACACACG CCTTTAATTC CAGCACTTGG GAGGCAGAGG    5400

CAGGCGGATT TCTGAGTTCG AGGCCAGCCT GGTCTACAAA GTGAGTTCCA GGACAGCCAG    5460

GGCTACACAG AGAAACCCTG TCTCAAAAAA CAAACAAACA AACAAACAAA CAAACCACCA    5520

TGAACTACCT GTGTATGCAT GTTGTGTGTG CTTGCATTGT GCAGGTCAAA TGAACACACT    5580

GGGACTCTTC CACTAACACT CTCTACCTCG TTCCCTAAGA GGGTCTCCTG CTGAACATGG    5640

AGTTTCCCAT TTCTTTTGGT TAGGCTGGCA GCCAGCCAGC AAGTCCCAGC GATCCTCCTG    5700

TCTCCTCTTC CTCCTGCTCA GCCCCAGGGG TGGAGTCTTA GGTATGCGTG GCCATGCCAG    5760

GCTTTTTCCA TGGGTGCTGG AGATCCAGAC GCAGCTTCTC ATGTTCGCGC AGTGGCACTC    5820

TTGCCCACTG AAGCATCTTC CATCTTGCCC ACTGAAGCAT CTCCCATCTT ACCCACTCAA    5880

GCATCTTCCA TCTTACCCAC TCAAGCATCT TCCATCTTAC CCACTCAAGC ATCTTCCATC    5940

TTACCCACTC AAGCATCTTC CAGCTCCTTA GTATGTTTTT TTTTAAACA TGTACTTGGC    6000

TTTTTAAAAT TGTAATAAAC TAAAGGTATA CAATATGTAT TGATTGATAT GCTTACTTAT    6060
```

-continued

| | | | | | | |
|---|---|---|---|---|---|---|
| GTATTTATCT | TTATTTTCTT | ATTTTTTTAA | AAAATTTATT | TTATTTATAT | GAATACACTG | 6120 |
| TAGCTGACTT | CAGACACACC | AGAACAGGGC | ATTGGATCCC | ATTACGGATG | GTTGTGAGCC | 6180 |
| ACCATGTGGT | TGCTGGGAAT | TGAACTCAGG | ACCTTTGGAA | GAACAGTCTC | TCTGGCTCTG | 6240 |
| TAGTTATCTT | TCAGTATACT | TTTCCTTGAA | AATTTTATAT | GTCTGTGCGA | TCTATTCTGG | 6300 |
| TCCTACCATT | CACTCTCACT | CTTCCTGGAC | TTCCCAGTAT | GGCCCCCTCC | CGATTTCAAA | 6360 |
| TCTTCTCACT | CTTATTTTTT | AGCCCACTGA | GTTCAGTTAG | TGTTGTCCCT | ATGAGCACGT | 6420 |
| GTGGACCATC | TACTTGAGCT | TAGGCAACCT | ACCAGTGGCC | ACATCCCTAC | AGGAAAGGTA | 6480 |
| CTCTTCCTCT | CTTGGTGGCC | ATAAACCCCC | AACGGGTCCT | CACATAGGGC | AGGAGCCTTA | 6540 |
| GGAGTTTCCC | TCCCCATTCA | TACTAAACTT | TGGTTGGCTT | GATGGTGTGA | AGATAACCAC | 6600 |
| AGCTGCTGTG | AGGTCCTGAG | TACAAGGGCC | AAGTCACGTC | CAGGAGGCAG | CATCTCACAG | 6660 |
| TACTTACCCC | CAGTCTCTGG | CTCGAACATC | CTTCCCACCA | TCCCCCTTCA | TCATGTTCCT | 6720 |
| TAAGCTT | | | | | | 6727 |

What is claimed is:

1. A transgenic mouse whose genome contains a chimeric DNA sequence, said chimeric DNA sequence comprising:
a basal keratinocyte specific transcription control sequence and a DNA segment which encodes interleukin-5, wherein the basal keratinocyte specific transcription control sequence and the DNA segment which encodes interleukin-5 are operatively linked to each other and are integrated into the genome of the mouse, wherein the DNA segment that encodes interleukin-5 lacks endogenous interleukin-5 control sequences which are 5' to the interleukin-5 coding sequence, and wherein the DNA segment is expressed so as to result in elevated levels of eosinophils in the blood and skin, increased thickening of the skin or an increased inflammatory response to oxazolone in the transgenic mouse relative to a corresponding nontransgenic mouse.

2. The transgenic mouse of claim 1 wherein the transcriptional control sequence comprises the K14 transcriptional control sequences.

3. An expression cassette comprising a DNA segment encoding interleukin-5 operably linked to a basal keratinocyte specific transcription control sequence, wherein the DNA segment that encodes interleukin-5 lacks endogenous interleukin-5 control sequences which are 5' to the interleukin-5 coding sequence.

4. The expression cassette of claim 3 wherein the basal keratinocyte specific transcription control sequence comprises the K14 transcriptional control sequences.

5. A method for tissue-specific expression for interleukin-5 in a transgenic mouse, comprising expressing a chimeric DNA sequence in the cells of a transgenic mouse, said chimeric DNA sequence comprising a basal keratinocyte specific transcription control sequence and a DNA segment which encodes interleukin-5, wherein the basal keratinocyte specific transcription control sequence and the DNA segment which encodes interleukin-5 are operatively linked to each other and are integrated into the genome of the mouse, wherein the DNA segment that encodes interleukin-5 lacks endogenous interleukin-5 control sequences which are 5' to the interleukin-5 coding sequence, and wherein the DNA segment is expressed so as to result in elevated levels of eosinophils in the blood and skin, increased thickening of the skin or an increased inflammatory response to oxazolone in the transgenic mouse relative to a corresponding nontransgenic mouse.

6. A method of using a transgenic mouse to screen for an agent that inhibits or reduces an interleukin-5 associated pathology, comprising:
(a) administering the agent to a transgenic mouse, wherein the transgenic mouse comprises a chimeric DNA sequence comprising a basal keratinocyte specific transcription control sequence operatively linked to a DNA segment which encodes interleukin-5, wherein the chimeric DNA sequence is integrated into the genome of the mouse, wherein the DNA segment that encodes interleukin-5 lacks endogenous interleukin-5 control sequences which are 5' to the interleukin-5 coding sequence; and
(b) determining whether said agent reduces or inhibits levels of eosinophils in the blood and skin, thickening of the skin or an inflammatory response to oxazolone in the transgenic mouse relative to a transgenic mouse of step (a) which has not been administered the agent.

7. The method of claim 5 or 6 wherein the basal keratinocyte specific transcription control sequence comprises the K14 transcription control sequence.

* * * * *

UNITED STATES PATENT AND TRADEMARK OFFICE
CERTIFICATE OF CORRECTION

PATENT NO. : 6,215,040 B1
DATED : April 10, 2001
INVENTOR(S) : James J. Lee and Nancy A. Lee It is certified that error appears in the above-identified patent and that said Letters Patent is hereby corrected as shown below:

Column 2,
Line 57, delete "interieukin-5" and insert -- interleukin-5 -- therefor.

Column 5,
Line 6, delete "pNNO$^3$" and insert -- pNNO3 -- therefor.
Line 53, delete "NJ. 1638" and insert -- NJ.1638 -- therefor.

Column 6,
Line 6, delete "¶The" and insert —† The -- therefor.

Line 33, delete "15 pg" and insert -- 15 μg -- therefor.
Line 44, delete "NJ. 1638" and insert -- NJ.1638 -- therefor.
Line 47, delete "Fully-body" and insert -- Full-body -- therefor.
Line 67, delete "(n 24)" and insert -- (n≥4) -- therefor.

Column 7,
Line 58, delete "25 Em" and insert -- 25 μm -- therefor.

Column 8,
Line 11, delete "50 Am" and insert -- 50 μm -- therefor.
Line 25, delete "50 Im" and insert -- 50 μm -- therefor.
Line 26, delete "25 Em" and insert -- 25 μm -- therefor.
Line 44, delete "(4 um)" and insert -- (4μm) -- therefor.
Line 52, delete "bars 50 Wm." and insert -- bars = 50 μm. -- therefor.

Column 10,
Line 29, delete "CD36 " and insert -- CD3δ -- therefor.

Column 12,
Line 55, delete "." after "radiolabeled,".
Line 61, delete "$^{32}$p" and insert -- $^{32}$P -- therefor.

Column 13,
Line 19, delete "albumin/0. 1%" and insert -- albumin/0.1% -- therefor.

Column 14,
Line 4, delete "72°C. +0 minute" and insert -- 72° C 10 minute -- therefor.
Line 67, delete "~000 rpm" and insert -- ~1000 rpm -- therefor.

Column 15,
Line 41, delete "CD3e" and insert -- CD3∈ -- therefor.

UNITED STATES PATENT AND TRADEMARK OFFICE
CERTIFICATE OF CORRECTION

PATENT NO. : 6,215,040 B1
DATED : April 10, 2001
INVENTOR(S) : James J. Lee and Nancy A. Lee It is certified that error appears in the above-identified patent and that said Letters Patent is hereby corrected as shown below:

Column 16,
Line 52, delete "NJ. 1638" and insert -- NJ.1638 -- therefor.

Column 18,
Table 1, last entry in column titled "lymphocyte" under "percentage of each cell type", delete "(1.46)" and insert -- (14.6) -- therefor.

Column 19,
Line 11, delete "NJ. 1638" and insert -- NJ.1638 -- therefor.
Line 52, delete "NJ. 1638" and insert -- NJ.1638 -- therefor.
Line 65, delete "NJ. 1638" and insert -- NJ.1638 -- therefor.

Columns 21-22,
Table 3, eighth entry in column titled "mononuclear", after "27.38" insert -- (10.78) --.
Table 3, eighth entry in column titled "eosinophil", delete "(10.78)" and insert -- (8.09) -- therefor.

Column 25,
Line 32, delete "NJ. 1638" and insert -- NJ.1638 -- therefor.

Column 27,
Lines 28-29, delete "24 15 months" and insert -- 24 months -- therefor.

Column 29,
Line 18, delete "CD3δdriven" and insert -- CD3δ driven -- therefor.

Column 30,
Line 23, delete "NJ. 1638" and insert -- NJ.1638 -- therefor.

UNITED STATES PATENT AND TRADEMARK OFFICE
CERTIFICATE OF CORRECTION

PATENT NO.    : 6,215,040 B1
DATED         : April 10, 2001
INVENTOR(S)   : James J. Lee and Nancy A. Lee It is certified that error appears in the above-identified patent and that said Letters Patent is hereby corrected as shown below:

<u>Columns 33-34,</u>
Table 6, second entry in column titled "Serum IL-5", delete "1696" and insert -- 1696 $(449)^{4-}$ -- therefor.
Table 6, second entry in first column titled "Total", delete "41.4 $(449)^4$" and insert -- 41.4 $(16.3)^4$ -- therefor.
Table 6, second entry in first column titled "lymphocyte", delete "18.8 $(16.3)^4$" and insert -- 18.8 (10.6) -- therefor.
Table 6, second entry in column titled "monocyte", delete "2.6 (10.6)" and insert -- 2.6 (1.0) -- therefor.
Table 6, second entry in first column titled "eosinophil", delete "17.3 (8.7) (1.0)" and insert -- 17.3 (8.7) -- therefor.
Table 6, second entry in second column titled "Total", delete "30.3" and insert -- 30.3 $(3.8)^4$ -- therefor.
Table 6, second entry in column titled "erythroblasts", delete "4.1 (1.6) $(3.8)^4$" and insert -- 4.1 (1.6) -- therefor.
Table 6, second entry in second column titled "lymphocyte", delete "3.8" and insert -- 3.8 (0.6) -- therefor.
Table 6, second entry in second column titled "eosinophil", delete "15.2 (0.6)" and insert -- 15.2 (1.8) -- therefor.
Table 6, second entry in second column titled "neutrophil", delete "7.3 (3.9) (1.8)" and insert -- 7.3 (3.9) -- therefor.

<u>Column 39,</u>
Line 20, delete "type 11" and insert -- type II -- therefor.

Signed and Sealed this

Nineteenth Day of August, 2003

JAMES E. ROGAN
*Director of the United States Patent and Trademark Office*